United States Patent
Keller et al.

(10) Patent No.: US 6,703,539 B1
(45) Date of Patent: Mar. 9, 2004

(54) METHOD AND COMPOSITIONS FOR MODIFYING LEVELS OF SECONDARY METABOLIC COMPOUNDS IN PLANTS

(75) Inventors: Wilfred A. Keller, Saskatoon (CA); Raju S. S. Datla, Saskatoon (CA); Jin-Zhuo Dong, Saskatoon (CA); Fawzy Georges, Saskatoon (CA); Atta A. K. Hussain, Saskatoon (CA); Gopalan Selvaraj, Saskatoon (CA)

(73) Assignee: National Research Council of Canada (CA)

( * ) Notice: Subject to any disclaimer, the term of this patent is extended or adjusted under 35 U.S.C. 154(b) by 0 days.

(21) Appl. No.: 09/235,153

(22) Filed: Jan. 22, 1999

Related U.S. Application Data

(63) Continuation-in-part of application No. 09/012,453, filed on Jan. 23, 1998, now abandoned.
(60) Provisional application No. 60/072,156, filed on Jan. 22, 1998.

(51) Int. Cl.$^7$ ................................................ C12N 15/82
(52) U.S. Cl. ........................ 800/278; 800/281; 800/287; 800/288; 800/298; 800/295
(58) Field of Search ................................. 800/278, 281, 800/287, 288, 289, 298, 295

(56) References Cited

U.S. PATENT DOCUMENTS

| | | | |
|---|---|---|---|
| 5,543,576 A | * 8/1996 | Van Ooijen et al. | ........ 800/250 |
| 5,662,958 A | * 9/1997 | Kennelly et al. | ........... 426/630 |
| 5,900,525 A | * 5/1999 | Austin-Phillips et al. | ... 800/205 |
| 5,948,667 A | * 9/1999 | Cheng et al. | ............... 435/200 |

FOREIGN PATENT DOCUMENTS

| | | | |
|---|---|---|---|
| EP | 818138 | | 1/1998 |
| JP | 8266179 | | 10/1996 |
| WO | WO9114782 | | 10/1991 |
| WO | WO-9201042 A1 | * | 1/1992 |
| WO | WO9219731 | | 11/1992 |
| WO | WO-9305160 | * | 3/1993 |
| WO | 96/00789 | * | 6/1995 |
| WO | WO9527068 | | 10/1995 |
| WO | WO9639859 | | 12/1996 |
| WO | WO9723599 | | 7/1997 |

OTHER PUBLICATIONS

Cruciferae—Garden Webs HortiPlex Plan Databas.*
Brassicaceae—Garden Webs HortiPlex Plan Database.*
Heterogeneous nuclear RNA (hnRNA).*
Chapple, Clint C.S., et al. "An Arabidopsis Mutant Defective in the General Phenylpropanoid Pathway" *The Plant Cell*, 4:1413–1424, Nov. 1992.
Wood Andrew J., et al. "Betaine Aldehyde Dehydrogenase in Sorghum" *Plant Physiol*, 110:1301–1308 (1996).
Burnet, Michael, et al. "Assay, Purification, and Partial Characterization of Choline Monooxygenase from Spinach" *Plant Physiol*, 108:581–588 (1995).
Bouchereau, Alain, et al. "Structural changes in sinapic acid conjugates during seedling development of rape", *Plant Physiol. Biochem.*, 30(4):467–475 (1992).
Vogt, Thomas, et al. "Purification and Characterization of Sinapine Synthase from Seeds of *Brassica napus*", *Archives of Biochemistry and Biophysics*, 300(2):622–628, Feb. 1, 1993.
Selvarajs Gopalan, et al. "Glycinebetaine in Oilseed Rape and Flax Leaves: Detection by Liquid Chromatography/Continuous Flow Secondary Ion–Mass Spectrometry", *Phytochemistry*, 38(5):1143–1146, 1995.
Chapple, et al. "Secondary Metabolite Profiles of Crucifer Seeds: Biogenesis, Role, and Prospects for Directed Modification", *Biosynthesis and Molecular Regulation of Amino Acids in Plants*, BK Singh, HE Flores, JC Shannon, eds, American Society of Plant Physiologists 239:248, Copyright 1992.
Holmström, Kjell–Ove, et al. "Production of the *Escherichia coli* betaine–aldehyde dehydrogenase, an enzyme required for the synthesis of the osmoprotectant glycine betaine, in transgenic plants", *The Plant Journal*, 6(5):749–758, (1994).
Chapple, Clint "Genetic Characterization of Secondary Metabolism in Arabidopsis" *Genetic Engineering of Plant Secondary Metabolism*, Plenum Press, New York, 251:274 (1994).
Goh, Y.K., et al. "Effect of Ammoniation of Rapeseed Meal on the Sinapine Content of the Meal" *British Poultry Science*, 23:121–128 (1982).
Kräling, K., et al. "Genetic Variation of the Content of Sinapoyl Esters on Seeds of Rape, B. napus" *Plant Breeding*, 106, 254–257 (1991).

(List continued on next page.)

Primary Examiner—Gary Benzion
Assistant Examiner—Juliet C. Switzer
(74) Attorney, Agent, or Firm—Lorusso, Loud & Kelly

(57) ABSTRACT

The present invention provides a method of making a genetically transformed plant which has an altered content of at least one product of a secondary metabolic pathway. The method consists of introducing into a plant cell capable of being transformed and regenerated to a whole plant a DNA expression cassette. The expression cassette includes DNA sequences required for transformation and selection in plant cells. It also includes a DNA sequence that, under the control of a promoter active in plant cells, encodes a protein capable of modifying the utilization of a substrate in the secondary metabolic pathway. The substrate is not a primary metabolite of the group selected from glucose, amino acids, common fatty acids and nucleotides. A plant or plant tissues including seeds can then be recovered having an altered content of at least one product of the secondary metabolic pathway. The invention also provides for feed products derived from the plants and seeds obtained according to the method.

12 Claims, 33 Drawing Sheets

OTHER PUBLICATIONS

Figure 1:
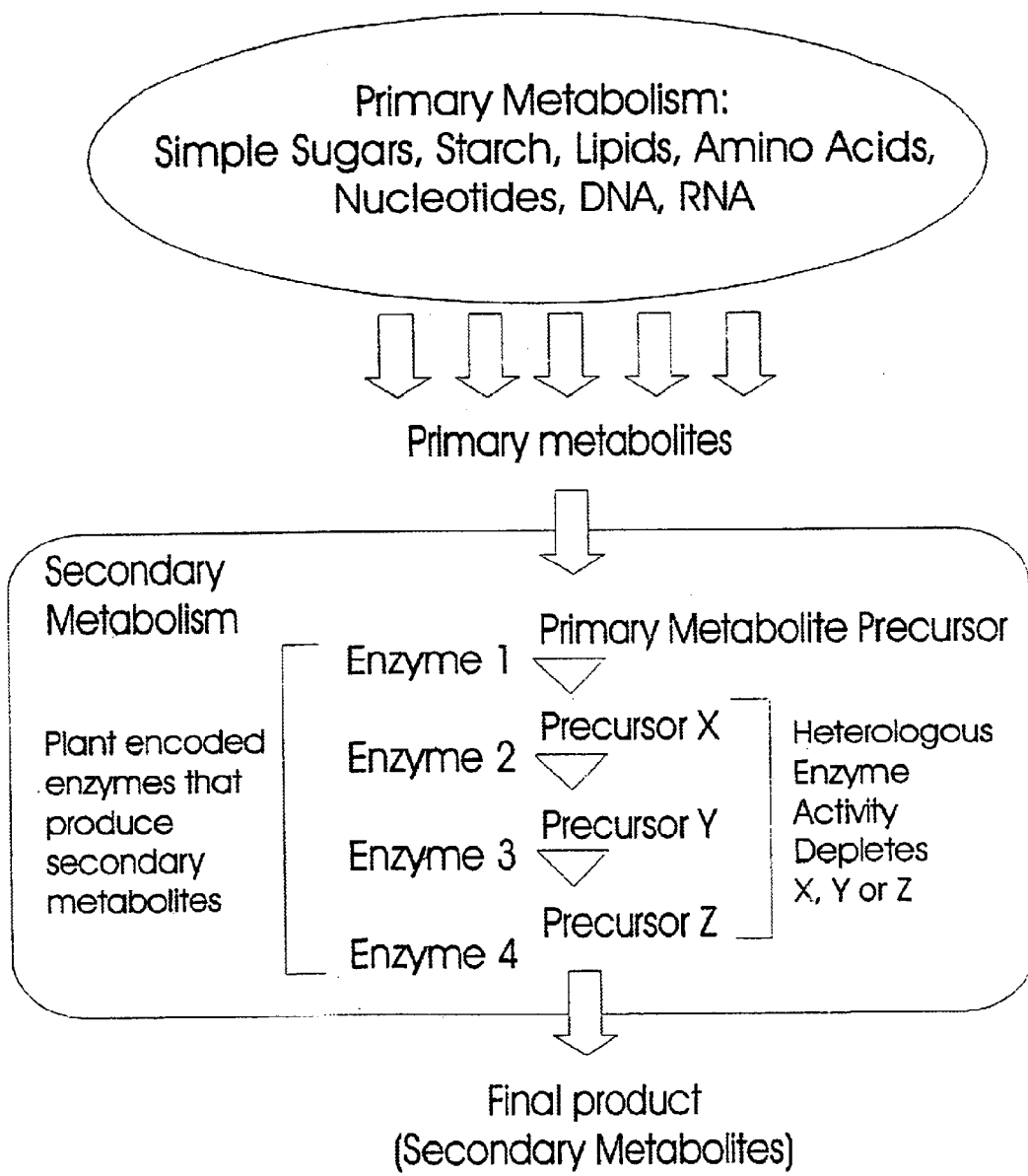

Lorenzen, Maike, et al. "Sinapic Acid Ester Metabolism in Wild Type and a Sinapoylglucose–Accumulating Mutant of Arabidopisis" *Plant Physiol.* 112:1625–1630 (1996).

Fenwick, G. Roger "A Micromethod for the Screening of Individual Seeds and Cotyledons of *Brassica napus* and *Brassica campestris* (Rapeseed) for Low Sinapine Content" *J. Sci. Food Agric.* 30:661–663 (1979).

Ismail, F. "Bitterness and Astringency of Sinapine and Its Components" *Journal of Food and Science* 46:1241–1244 (1981).

Regenbrecht, Josef "Distribution of 1–Sinapoylglucose: Choline Sinapoyltransferase Activity in the Brassicaceae" *Phytochemistry* 24:407–410 (1985).

Hayashi, Hidenori, et al. "Transformation of *Arabidopsis thaliana* with the codA gene for choline oxidase; accumulation of glycinebetaine and enhanced tolerance to salt and cold stress" *The Plant Journal* 12(1):133–142 (1997).

Deshnium, Patcharaporn, et al. "Transformation of Synechococcus with a gene for choline oxidase enhances tolerance to salt stress" *Plant Molecular Biology* 29:897–907 (1995).

Li, Jiayang, et al. "Arabidopsis Flavonoid Mutants Are Hypersensitive to UV–B Irradiation" *The Plant Cell* 5:171–179 (1993).

Elkind, et al. "Abnormal plant development and down–regulation of phenylpropanoid biosynthesis in transgenic tobacco containing a heterologous phenylalanine ammonia–lyase gene", *Proc. Natl. Acad. Sci.* 87:9057–9061 (1990).

Kutchan, T.M. "Alkaloid Biosynthesis–The basis for metabolic engineering of medicinal plants", *The Plant Cell*, 7:1059–1070 (1995).

Varin, L. "Flavonoid sulfation: Phytochemistry, enzymology and molecular biology", Phenolic Metabolism in Plants 233–254 (1990).

Lefebrves D. "Expression of mammalian me tallothionein suppresses glucosinolate synthesis in brassica campestris", Plant Physiol. 93:522–524. (1990).

Smart, et al. "Overexpression of D–myo–inositol–3–phosphate synthase leads to elevated levels of inositol in Arabidopsis", Plant Molecular Biology 33:811–820 (1997).

Boudet, et al. Transley review No. 80, "Biochemistry and molecular biology of lignification", *New Phytol.* 129:203–236 (1995).

Herbers, et al. "Manipulating metabolic partitioning in transgenic plants", *Trends in Biotechnology* Vol:14. (1996).

Lindsey, K., "Prospects for the genetic manipulation of complex metabolic pathways", *Manipulating secondary metabolism in culture*, R.J. Robins, MJC Rhodes, eds., AFRC Institute of Arable Crops Research, Norwich Laboratory, Norwich, UK, pp. 123–133 (1988.

Yeoman, et al. Transley review No. 90, "Manipulating secondary metabolism in cultured plant cells", *New Phytol* 134:553–569. (1996).

Songstad, D., "High levels of tryptamine accumulation in transgenic tobacco expressing tryptophan decarboxylase", *Plant Physiol.* 49:1410–1413 (1990).

Ibrahim, R.K., "Engineering altered glucosinolate biosynthesis by two alternative strategies", *Genetic Engineering of Plant Secondary Metabolism*, 125–152 (1994).

Van der Geest, et al "A 68 bp element of the β–phaseolin functions as a seed–specific enhancer", *Plant Molecular Biology* vol. 32:579–588 (1996).

Smith, et al. "Antisense RNA inhibition of polygalacturonase gene expression in transgenic tomatoes", *Nature* Vol 334:724–726 (1988).

* cited by examiner

Sinapine in *Brassica napus* Seeds
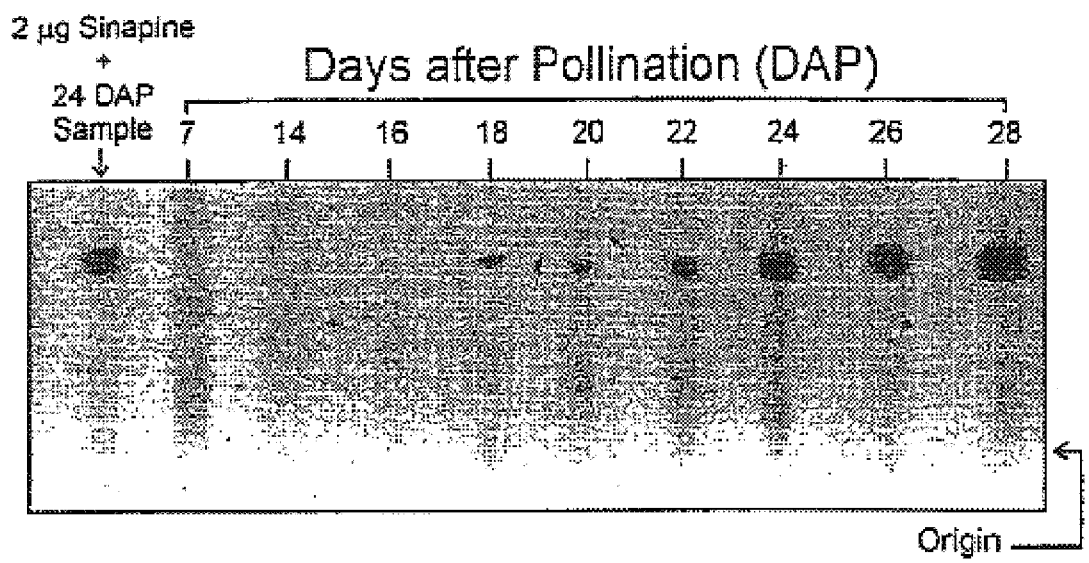
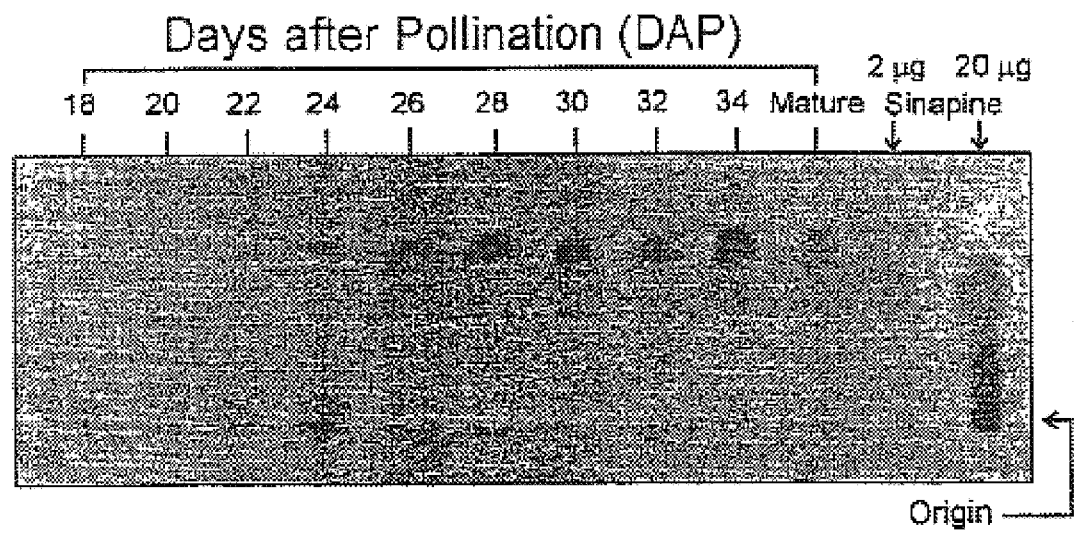
FIG. 3

```
   1  ATGCACATCG ACAACGTCGA AAACCTCAAC GACCGCGAGT TCGACTACAT
  51  CATCATCGGC GGCGGTTCCG CCGGAGCGGC AGTCGCCGCC CGCCTGAGCG
 101  AGGAGCCCAC CGTGTCCGTG GCGCTGGTGG AGGCCGGCCC GGACGACCGC
 151  GGCGTTCCCG AGGTACTGCA GCTCGACCGC TGGATGGAGC TGCTGGAATC
 201  CGGCTACGAC TGGGACTACC CGATCGAACC GCAGGAGAAC GGCAACTCCT
 251  TCATGCGCCA CGCCCGCGCG AAGATCATGG GTGGCTGCTC CAGCCACAAC
 301  TCCTGCATCG CCTTCTGGGC CCCGCGCGAA GACCTGGACG AGTGGGAGTC
 351  CAAGTACGGC GCCACCGGCT GGAACGCTGA GTCCGCCTGG CCGCTGTACC
 401  AGCGGCTGGA GACCAACGAG GACGCCGGCC CGGACGCGCC GCACCACGGC
 451  GACTCAGGCC CGGTGCACCT GATGAACGTG CCCCCGGCGG ACCCCGCCGG
 501  CGTCGCACTC CTGGACGCCT GCGAACAGGC AGGCATTCCG CGCGCGAAGT
 551  TCAACACCGG CACCACCGTG ATCAATGGCG CCAACTTTTT CCAGATCACA
 601  CGCCGCGCGG ACGGCACCCG TTCCTCCAGC TCGGTCTCCT ACATCCACCC
 651  GATCATCGAG CGCGGGAACT TCACCCTGCT GACCGGGTTG CGCGCCCGGC
 701  AACTGGTGTT CGACGCGGAC AAGCGCTGCA CCGGCGTCGA CGTTGTGGAC
 751  TCGGCGTTCG GCCGGACTCA CCGGCTCTCC GCGCGTTGCG AGGTCATCCT
 801  GTCCACCGGC GCCATTGACT CGCCTAAGCT GCTCATGCTC TCCGGCATCG
 851  GCCCCGCCGC GCACCTCGCC GAGCACGGCG TCGAGGTCCT GGTCGACTCC
 901  CCCGGTGTCG GCGAGCACCT GCAGGACCAC CCCGAAGGCG TCGTCCAGTT
 951  CGAGGCCAAG CAGCAGATGG TGCAGACTTC GACGCAGTGG TGGGAGATCG
1001  GCATCTTCAC CCCCACCGAG AACGGCCTGG ACCGCCCGGA CCTGATGATG
1051  CACTACGGCT CCGTCCCGTT CGACATGAAC ACCCTGCGGT ACGGCTACCC
1101  CACCACGGAG AACGGCTTCA GCCTCACGCC GAACGTCACG CACGCCCGCT
1151  CCCGCGGCAC CGTCCGGCTG CGCAGCCGCG ACTTCCGCGA CAAGCCCGCC
1201  GTCGACCCGC GGTACTTCAC TGATCCGGAG GGCCACGACA TGCGCGTCAT
1251  GGTGGCCGGC ATCCGCAAGG CCCGTGAAAT CGCCGCCCAG CCTGCCATGG
1301  CCGAATGGAC CGGCCGCGAG CTCTCGCCCG GCACCGAGGC GCAGACCGAC
```

FIG. 10A

```
1351  GAGGAACTGC AGGACTACAT CCGCAAGACG CACAACACCG TTTACCACCC
1401  CGTCGGCACC GTCCGCATGG GACCAGCCGA CGACGACATG TCGCCGCTCG
1451  ACCCCGAGCT GCGGGTGAAG GGCGTGACCG GCCTGCGCGT CGCCGATGCC
1501  TCTGTCATGC CTGAACACGT CACGGTCAAT CCCAACATCA CCGTCATGAT
1551  GATCGGCGAA CGCTGCGCCG ACCTCATCCG CGCCAGCCGG ACCGGCGAAA
1601  CAACGACGGC GGAGGCGGAG CTCAGCGCGT CCCTCGCCTG A
```

FIG. 10B

Predicted amino acid sequence of choline oxidase open frame.

```
  1  MHIDNVENLN DREFDYIIIG GGSAGAAVAA RLSEEPTVSV ALVEAGPDDR
 51  GVPEVLQLDR WMELLESGYD WDYPIEPQEN GNSFMRHARA KIMGGCSSHN
101  SCIAFWAPRE DLDEWESKYG ATGWNAESAW PLYQRLETNE DAGPDAPHHG
151  DSGPVHLMNV PPADPAGVAL LDACEQAGIP RAKFNTGTTV INGANFFQIT
201  RRADGTRSSS SVSYIHPIIE RGNFTLLTGL RARQLVFDAD KRCTGVDVVD
251  SAFGRTHRLS ARCEVILSTG AIDSPKLLML SGIGPAAHLA EHGVEVLVDS
301  PGVGEHLQDH PEGVVQFEAK QQMVQTSTQW WEIGIFTPTE NGLDRPDLMM
351  HYGSVPFDMN TLRYGYPTTE NGFSLTPNVT HARSRGTVRL RSRDFRDKPA
401  VDPRYFTDPE GHDMRVMVAG IRKAREIAAQ PAMAEWTGRE LSPGTEAQTD
451  EELQDYIRKT HNTVYHPVGT VRMGPADDDM SPLDPELRVK GVTGLRVADA
501  SVMPEHVTVN PNITVMMIGE RCADLIRASR TGETTTAEAE LSASLA*
```

FIG. 11

Reduction of Sinapine in Cox and Cox/BaDH lines

| Plant line | Number of plants analyzed | Plant Genotype | Sinapine Absorbance Units | Sinapine Levels (Control = 100%) |
|---|---|---|---|---|
| 2026 x 1534 | 15 | Cox + Badh | 13,878 | 13.6% |
| 2013 | 23 | Cox | 19,874 | 19.5% |
| 1994 | 26 | Cox | 23,344 | 22.9% |
| 2026 | 27 | control | 101,856 | 100% |

FIG. 15

Total Soluble Phenolic Content in Transgenic Lines

| Plant line | Number of plants analyzed | Plant Genotype | Soluble Phenolic Absorbance Units | Soluble Phenolic Levels (Control = 100%) |
|---|---|---|---|---|
| 2026 X 1534 | 15 | Cox + Badh | 103,828 | 69.0% |
| 2013 | 23 | Cox | 98,222 | 78.0% |
| 1994 | 26 | Cox | 97,370 | 77.3% |
| 2026 | 27 | control | 125,882 | 100% |

FIG. 16

```
  1  ATGGACCAAT TCGTGGGTCT CCACATGATC TACACATACG AGAACGGTTG
 51  GGAGTACGAA ATCTACATCA AGAACGACCA CACAATCGAC TACCGTATCC
101  ACAGTGGTAT GGTGGGTGGT AGGTGGGTGA GGGACCAAGA GGTGAACATC
151  GTGAAGCTCA CAAAGGGTGT GTACAAGGTG AGCTGGACAG AGCCAACAGG
201  TACAGACGTG AGCCTCAACT TCATGCCAGA GGAGAAGAGG ATGCACGGTG
251  TGATCTTCTT CCCAAAGTGG GTGCACGAGA GGCCAGACAT CACAGTGTGC
301  TACCAAAACG ACTACATCGA CCTCATGAAG GAGAGCAGGG AGAAGTACGA
351  GACATACCCA AGTACGTGG TGCCAGAGTT CGCTGACATC ACATACATCC
401  ACCACGCTGG AGTGAACGAC GAGACAATCA TCGCTGAgGC TCCATACGAg
451  GGTATGACAG ACGAgATCAG GGCTGGTAgG AAG
```

FIG. 17

```
1    MDQFVGLHMI YTYENGWEYE IYIKNDHTID YRIHSGMVGG RWVRDQEVNI
51   VKLTKGVYKV SWTEPTGTDV SLNFMPEEKR MHGVIFFPKW VHERPDITVC
101  YQNDYIDLMK ESREKYETYP KYVVPEFADI TYIHHAGVND ETIIAEAPYE
151  GMTDEIRAGR K
```

FIG. 18

```
cipimtla : AAAAAAAAAATTTTACTTCTCTGTTTTACCAAAAAGAGAAAAAAAAATGACTACTTACAC
   imtsp : ..........................................------------------ cipimtla : CAATGGCAACTACACACAACCAAAAACCCTAGACAAAGATGAACAATTAGCTGGTTTGGC
   imtsp : ------------------------------------------------------------ cipimtla : AGTGACATTAGCAAATGCAGCTGCTTTTCCAATGATCCTGAAATCAGCCTTTGAGCTAAA
   imtsp : ------------------------------------------------------------ cipimtla : AATCCTTGACATATTCTCAAAAGCAGGGGAAGGCGTGTTTGTATCGACTTCTGAGATCGC
   imtsp : ------------------------------------------------------------ cipimtla : TAGCCAAATCGGGGCAAAGAACCCTAATGCCCCGGTGTTGTTGGACCGGATGCTCCGGCT
   imtsp : ------------------------------------------------------------ cipimtla : CCTGGCTAGCCACTCTGTGTTAACATGCAAGCTCCAAAAGGGTGAGGGTGGTTCTCAAAG
   imtsp : ------------------------------------------------------------ cipimtla : GGTGTATGGTCCAGCTCCCCTTTGCAACTATCTTGCTAGTAATGATGGTCAAGGCTCTCT
   imtsp : ------------------------------------------------------------ cipimtla : TGGCCCTTTGCTTGTTTTGCATCATGACAAGGTCATGATGGAGAGTTGGTTTCACTTGAA
   imtsp : ------------------------------------------------------------ cipimtla : TGATTACATACTAGAAGGAGGTGTTCCATTCAAGCGCGCTCATGGGATGATCCAATTCGA
   imtsp : ------------------------------------------------------------ cipimtla : CTACACTGGGACTGATGAAAGGTTCAATCATGTGTTCAACCAAGGGATGGCACACCACAC
   imtsp : ------------------------------------------------------------ cipimtla : TATCCTGGTCATGAAGAAGCTCCTTGACAACTACAATGGGTTTAATGATGTCAAGGTCCT
   imtsp : ------------------------------------------------------------ cipimtla : AGTTGATGTGGGTGGTAACATTGGTGTCAATGTGAGCATGATCGTCGCTAAGCATACTCA
   imtsp : ------------------------------------------------------------ cipimtla : CATTAAGGGCATCAACTATGACTTGCCTCATGTCATTGCTGATGCTCCTTCTTACCCCGG
   imtsp : ------------------------------------------------------------ cipimtla : TGTGGAGCATGTTGGTGGTAACATGTTTGAGAGCATACCACAAGCAGATGCCATTTTCAT
   imtsp : ------------------------------------------------------------ cipimtla : GAAGTGGGTGTTGCATGATTGGAGCGACGAGCATTGCGTGAAGATACTCAACAAGTGCTA
   imtsp : ------------------------------------------------------------ cipimtla : TGAGAGCCTGGCAAAGGGAGGGAAGATCATCCTTGTGGAATCGCTTATACCAGTAATCCC
   imtsp : ------------------------------------------------------------ cipimtla : AGAAGACAACCTCGAATCACACATGGTGTTTAGCCTTGATTGCCACACTTTGGTGCACAA
   imtsp : ------------------------------------------------------------
```

FIG. 24

```
cipimt1a : CCAAGGTGGAAAAGAGAGATCAAAGGAGGATTTTGAAGCCTTAGCTTCCAAGACTGGCTT
   imtsp : ------------------------------------------------------------ cipimt1a : CTCTACAGTTGATGTCATTTGCTGTGCCTATGACACTTGGGTCATGGAGCTCTACAAGAA
   imtsp : ------------------------------------------------------------ cipimt1a : GTGATTCAAGCTCTAAATGCTGTGTTGTTGTCATTGTTGCTAGCCCAAGTAGCTAGCTAG
   imtsp : ------------------------------------------------------------ cipimt1a : CTGGTTAAAATTTCTCCTACCTAGCATTTGTTTTATGGCTAAGTGAGGAGATTCATGTA
   imtsp : ------------------------------------------------------------ cipimt1a : TTGTAAATGTTGTGTTTGGGTTTGGGTTTGTATTTGTATTTGTGTTTTGTTGTTGTGTCT
   imtsp : ------------------------------------------------------------ cipimt1a : TTGTAGCTAAGTTGATATCCTGCTCATCTAGGCTGGCTGCATTTTTTTTGTGGCTGCCTG
   imtsp : ------------------------------------------------------------ cipimt1a : ACAATGTAGCATTTGTGGTTTTCTTTCAATAAAGCATCTA.TTGTACCTCTGTTATCAGT
   imtsp : -G-------------------------------------t-------------------- cipimt1a : GTATGATTTGCCTTTATTTTTAATAACTTAATTTTTTTTTCTTGTTTATATCCA
   imtsp : --------------------------.....................
```

FIG. 24
(continued)

PCR analysis of transgenic plants containing the *IMT* gene

M=molecular marker ;1= control plant ;2-22=transgenic plants

Reduction of Phytic Acid in transgenic Plants

Percent Phytic Acid reduction in F1, F2 & F3 seeds from plants containing pSIMT

| Transgenic Plant Number | Copy number of inserted gene | Percent Phytic Acid Reduction in F1 seeds | Percent Phytic Acid Reduction in F2 seeds | Percent Phytic Acid Reduction in F3 seeds |
|---|---|---|---|---|
| 3 | 4 | -10.5 | -26 | -36 |
| 6 | 3 | -3.7 | -24 | -32 |
| 11 | 1 | -8.6 | -30 | -34 |
| 17 | 3 | -5.7 | -29 | -25 |

(a negative percent (-) means a reduction in phytic acid relative to non-transformed plants.)

FIG. 30

Reduction of Phytic Acid in transgenic Plants

Percent Phytic Acid reduction in F1 & F2 seeds from plants containing pNIMT

| Transgenic Plant Number | Copy number of inserted gene | Percent Phytic Acid Reduction in F1 seeds | Percent Phytic Acid Reduction in F2 seeds |
|---|---|---|---|
| 5 | 1 | +24.31 | -37 |
| 7 | n.d. | -6.99 | -44.81 |
| 12 | 2 | -1.2 | -39 |
| 15 | 1 | -5.36 | -24 |
| 17 | 2 | -1.5 | -38 |
| 19 | 3 | -7.38 | -43 |
| 21 | 1 | -7.78 | -37 |
| N | 1 | +17.76 | -31.54 |

(a negative percent (-) means a reduction in phytic acid relative to non-transformed plants.)

FIG. 31

METHOD AND COMPOSITIONS FOR MODIFYING LEVELS OF SECONDARY METABOLIC COMPOUNDS IN PLANTS

This application is a continuation-in-part of U.S. application Ser. No. 09/012,453, filed on Jan. 23, 1998, now abandoned and claims priority from provisional application No. 60/072,156 filed on Jan. 22, 1998.

FIELD OF INVENTION

The present invention provides methods and compositions for the alteration of compounds produced by secondary metabolic pathways in plants. The invention also provides plant cells modified in content of secondary metabolites and plant seed with altered secondary metabolite content. In one embodiment, the content of anti-nutritional secondary metabolic products is altered in plants, plant cells and plant seeds according to the invention. In another embodiment, products found within the phenylpropanoid and sugar alcohol secondary metabolic pathways are altered in plants, plant cells and plant seeds according to the invention. The invention further provides genetic constructs and vectors useful for modifying the secondary metabolite content of plant cells and seeds. The invention further relates to modified seed meal, and to animal feed containing modified seed meal, particularly seed meal in which the secondary metabolite content is reduced or altered.

BACKGROUND OF THE INVENTION

Plants produce a variety of compounds by way of secondary metabolism. While not considered essential to plant metabolism, secondary metabolic pathways often produce unique biochemicals, some of which are considered anti-nutritional or even toxic. The secondary metabolic pathways and the compounds produced by these pathways are be specific to an individual species or genus. Thus manipulation of secondary metabolic pathways can produce novel compositions of biochemicals or produce plant tissue with altered secondary metabolic content. In particular, the manipulation of secondary metabolism for the purpose of alteration of secondary metabolic compounds that are anti-nutritional or toxic in nature can provide unique applications in the food and feed area.

It is desirable to manipulate secondary metabolism without disturbing the biochemical processes considered essential for plant cell growth and survival. The collection of biochemical processes and the compounds involved which are essential for the growth and survival of the plant, are considered primary metabolic pathways and their products. Primary metabolism is generally considered to encompass those biochemical processes that lead to the formation of primary sugars, (such as glucose), amino acids, common fatty acids, nucleotides and the polymers derived from them (polysaccharides such as starch, proteins, lipids, RNA and DNA etc.) Yeoman and Yeoman, Tansley Review No. 90, *Manipulating Secondary Metabolism in Cultured Plant Cells*, New Phytologist, 134:553–569, 1996.

Thus the art recognizes that primary metabolism can be defined as those metabolic processes essential to the survival and growth of all plant cells whereas secondary metabolism can be defined as those biochemical processes that are not essential to all plant cells. For example, secondary metabolic. pathways determine such plant features as colour, taste, morphology, etc. Secondarymetabolism also produces various compounds that are recognized by insects or are involved in pathogen response. Some of these compounds may provide a benefit to some plant species under wild conditions, but under cultivation these compounds may be detrimental to the quality of the harvested product or may restrict the utility of the crop for certain applications. Some of the secondary metabolites are unique compounds that have evolved within a species as a result of specialized biochemical pathways. Secondary metabolism is not characterized by the redundancy in biochemical mechanisms which is typical of primary metabolism, thus, characteristically, the products of secondary metabolism are not produced by multiple pathways in the plant. Secondary metabolites are typically more plant-specific than the ubiquitous biochemicals which are involved in the primary pathways.

Numerous attempts to manipulate primary metabolic pathways have resulted in plant cells with altered starch or oil (lipid) content. However, gross manipulation of primary metabolism can be expected to lead to deleterious effects. For example, the composition of lipids can be changed, but elimination of lipids would obviously be deleterious to cell survival. Manipulation of primary metabolism is not always completely successful because redundant biochemical mechanisms can overcome some attempts at manipulation. Thus primary metabolic pathways in plants are often difficult to manipulate in a fashion that is predictable and provides useful and tangible results under cultivation conditions.

In some instances, primary metabolism has been altered successfully to produce a novel phenotype which represents a compositional change rather than a reduction or elimination of a specific substance. Typically, these manipulations have been accomplished by ectopic expression of a plant gene, such as over-expressing a gene in certain tissues or in a constitutive fashion rather than a regulated fashion, or by inhibition of a specific gene activity by antisense RNA, ribozymes or co-suppression. However, it has been difficult to predict a priori the results of such manipulations.

The expression of a plant enzyme can be modified at many levels. This includes control at the gene expression level, translation, protein processing and allosteric control of protein function. Thus ectopic expression of a plant gene involved in primary metabolism may not overcome the complex biochemical controls on regulation of primary metabolism. Furthermore, redundancy in primary metabolism also poses a difficult hurdle to overcome in these manipulations since primary metabolic pathways are essential to plant growth and survival. Accordingly attempts to alter primary metabolism often fail to provide the intended phenotype. Moreover, the evaluation of these modified plants at the field level, or under a variety of environmental extremes has often led to the discovery that the predicted-effect is not observed or plant performance is compromised. Thus, modification of primary metabolism requires careful consideration ofthe primary metabolic pathway or the discreet step in a pathway in order to achieve a specific phenotype.

The manipulation of secondary metabolic pathways has been complicated by a poor understanding of the biochemistry involved, little information on the genes expressed in secondary metabolic pathways and the complex inter-relationships between biochemical pathways in general.

However, methods to alter secondary metabolism can provide a valuable means to produce novel phenotypes, including those with altered levels of secondary metabolic compounds, for example those considered anti-nutritional in nature. Thus secondary metabolic pathways represent an important target for the genetic manipulation of plants.

Two biochemical pathways in plants that are considered secondary metabolic pathways have been the subject of studies aimed at alteration of the levels of the final products. The methods used to manipulate these pathways have not produced the desired results. For example, the phenylpropanoid pathway is involved in the formation of lignin and is considered a secondary metabolic pathway. The biosynthesis of lignin is part of the general phenylpropanoid biosynthetic pathway which produces at least three primary phenolic precursors, coumaric, ferulic and sinapic acids, products of which are polymerized into lignin and other phenolic compounds (see FIG. 2).

In attempts to alter the secondary metabolic phenylpropanoid pathway, the genes for many of the enzymes involved in the formation of the lignin monomers are currently identified as targets for lignin reduction via anti-sense or co-suppression technologies (e.g. U.S. Pat. Nos. 5,451,514, 5,633,439, WO 93/05160, WO 94/08036). These target genes include those encoding cinnamyl alcohol dehydrogenase, caffeic acid O-methyl-transferase and phenylalanine ammonia lyase. These techniques are directed to reduction of lignin content as this is assumed to have an overall beneficial effect on processing or digestibility of plants.

However, reduction of lignin by antisense or co-suppression technologies by targeting one of the genes in the phenylpropanoid pathway may have a number of undesirable effects. These may include increased disease susceptibility, altered growth rates or reduction of the physical strength of the plant fibre and hence a reduction in agronomic performance. It was shown that inhibition of the enzyme phenylalanine ammonia lyase leads to numerous deleterious phenotypes (Elkind et al., Abnormal Plant Development and Down-Regulation of Phenylpropanoid Biosynthesis in Transgenic Tobacco Containing a Heterologous Phenylalanine Ammonia Lyase Gene, Proc. Natl. Acad. Sci. USA 87: 9057–9061, 1990). The enzyme phenylalanine ammonia lyase acts on the primary metabolite, phenylalanine, an amino acid. The results from these experiments demonstrate that the alteration of secondary metabolism through modification of one of the primary metabolites involved in a particular secondary metabolic pathway may produce unexpected and deleterious phenotypes. Accordingly, the choice of the biochemical step(s) within a secondary metabolic pathway is crucial to producing plants which are phenotypically normal but which show a reduction of a specific secondary metabolite. Furthermore, the use of antisense RNA or co-suppression strategies may not provide the level or specificity of secondary metabolite reduction that is commercially acceptable. Additionally, inhibition of the genes encoding key enzyme activities may affect the expression of related genes. Thus little progress has been made with reduction of phenolic compounds considered anti-nutritional, or reduction of lignin content by antisense RNA or co-suppression without accompanying deleterious side effects.

A second example of efforts to alter a metabolic pathway that failed to produce the desired results is modification of glucosinolate biosynthesis in canola. Attempts to modify glucosinolate content of canola meal by manipulation of the glucosinolate pathway have been reported. One method that has been proposed to alter the biosynthesis of glucosinolates was to create a new pathway that competes for the sulfur used in the formation of glucosinolates, or reduce levels of tryptophan used in the formation of glucosinolates by conversion of tryptophan to tryptamine ("Engineering Altered Glucosinolate Biosynthesis by Two Alternative Strategies", by Ibrahim, Chavadej & De Luca, published in: *Genetic engineering of plant secondary metabolism* 1994, Plenum Publishing Corporation; New York; USA).

However, the method was not successful in reducing glucosinolate content of canola seed meal. The method failed to reduce the anti-nutritional content of glucosinolates in canola meal. Glucosinolates are made in the leaves of the plant and then transported to the seed. Thus the method was based on the belief that the simple alteration of the availability of one of the primary metabolites (sulphur, the amino acid tryptophan) used in the formation of glucosinolates would reduce the production of glucosinolates. However, the primary glucosinolates in seed are aliphatic glucosinolates that do not utilize the amino acid tryptophan for the production of side chains. Moreover, the results from these experiments (e.g., Chavadej et al., Proc. Natl. Acad. Sci USA, 91: 2166–2170, 1994) demonstrated that transgenic plants that carried an enzyme capable of altering the primary amino acid tryptophan did not contain reduced glucosinolates in the seed, the aliphatic glucosinolate content in the seed was equal to or possibly even greater than non-tranagenic plants. Thus the production of total glucosinolates in seed was not reduced even though a minor component (indole glucosinolates) appeared to be reduced. It is clear from genetic studies that low glucosinolate plants can be obtained by conventional breeding and there are a number of loci controlling low glucosinolates in crucifers. There are numerous biochemical transformations that take place within glucosinolate biosynthesis and those steps in common with all or most of the synthesis of glucosinolates are the steps which need to be targetted if a method of reducing total glucosinolates in needed. Thus, a general method to alter glucosinolate production in crucifers must take into account the different enzymes and substrates used in glucosinolate biosynthesis if a method of general utility is to be devised.

However, it appears that the enzymes used to obtain this modification also acted upon primary metabolites (the animo acid tryptophan and the mineral sulfur) thus any significant alteration of these compounds in the plant cell would be expected to have a deleterious effect. Accordingly the proposed method failed to specifically target the secondary metabolic pathway. Indeed the alteration of tryptophan can be expected to lead to many deleterious effects. Thus, alteration of the levels of a primary metabolite did not produce the intended effect of low glucosinolate canola meal, underscoring the difficulty of modifying primary metabolism.

Accordingly, a general method to alter secondary metabolism will be valuable for altering the biochemical composition of plant tissues. This can include, for example, reduction of anti-nutritional compounds, alteration of secondary metabolic profiles, providing plant tissue with altered processing characteristics, alteration of the levels of compounds of industrial utility or pharmaceutical interest, production of plants with modified taste, texture or appearance, production of plants with altered secondary metabolites involved in insect attraction, disease tolerance or other biological processes that are influenced by secondary metabolites, or plants with growth characteristics positively modified by alteration of secondary metabolites.

BRIEF SUMMARY OF THE INVENTION

The present invention provides a method to target the formation of a secondary metabolite. The method comprises altering the availability of a substrate that is specific to the secondary metabolic pathway and essential to the formation of the final secondary metabolic product, particularly those compounds within one to five biochemical steps of final product formation. Targeting substrates at steps near the final product formation avoids the problems associated with alterations of metabolites also involved in primary pathways, since it occurs after the entry point of a substrate into the primary metabolic pathway. Thus the method provides a novel means of specifically targeting the reduction or alteration of secondary metabolites by identifying precursors used within a secondary metabolic pathway that do not comprise substrates for primary metabolic pathways.

The method can also comprise altering the availability of a substrate in a tissue specific manner such that only certain tissues, e.g. seed tissues, are altered.

Thus the method provides a novel means of specifically targeting the reduction or alteration of secondary metabolites by identifying precursors used within a secondary metabolic pathway that do not comprise primary metabolic compounds.

In one embodiment, the present invention provides a method of making a genetically transformed plant comprising:

A) introducing into a plant cell capable of being transformed and regenerated to a whole plant a DNA expression cassette comprising, in addition to DNA sequences required for transformation and selection in plant cells, a DNA sequence that, under the control of a promoter active in plant cells, encodes a protein capable of modifying the utilization of a substrate in a secondary metabolic pathway, with the proviso that the substrate is not a primary metabolite of the group selected from glucose, amino acids, common fatty acids and nucleotides, and B) recovering a plant which has an altered content of at least one product of the secondary metabolic pathway.

In another embodiment, the present invention provides a method for making a genetically transformed seed comprising growing the plant obtained according to steps A and B of the method described above under conditions which permit the formation of seed.

The recombinant DNA is chromosomally integrated into the genome of a fertile plant mush that it is passed to subsequent generations.

In further embodiments, the present invention provides vectors for transforming plants, plants and seeds transformed according to the method described above, and feed products containing the seeds or meal derived therefrom.

BRIEF DESCRIPTIONS OF THE DRAWINGS

FIG. 1: A schematic representation of general scheme of the method to alter any secondary metabolic pathway.

Figure 2:
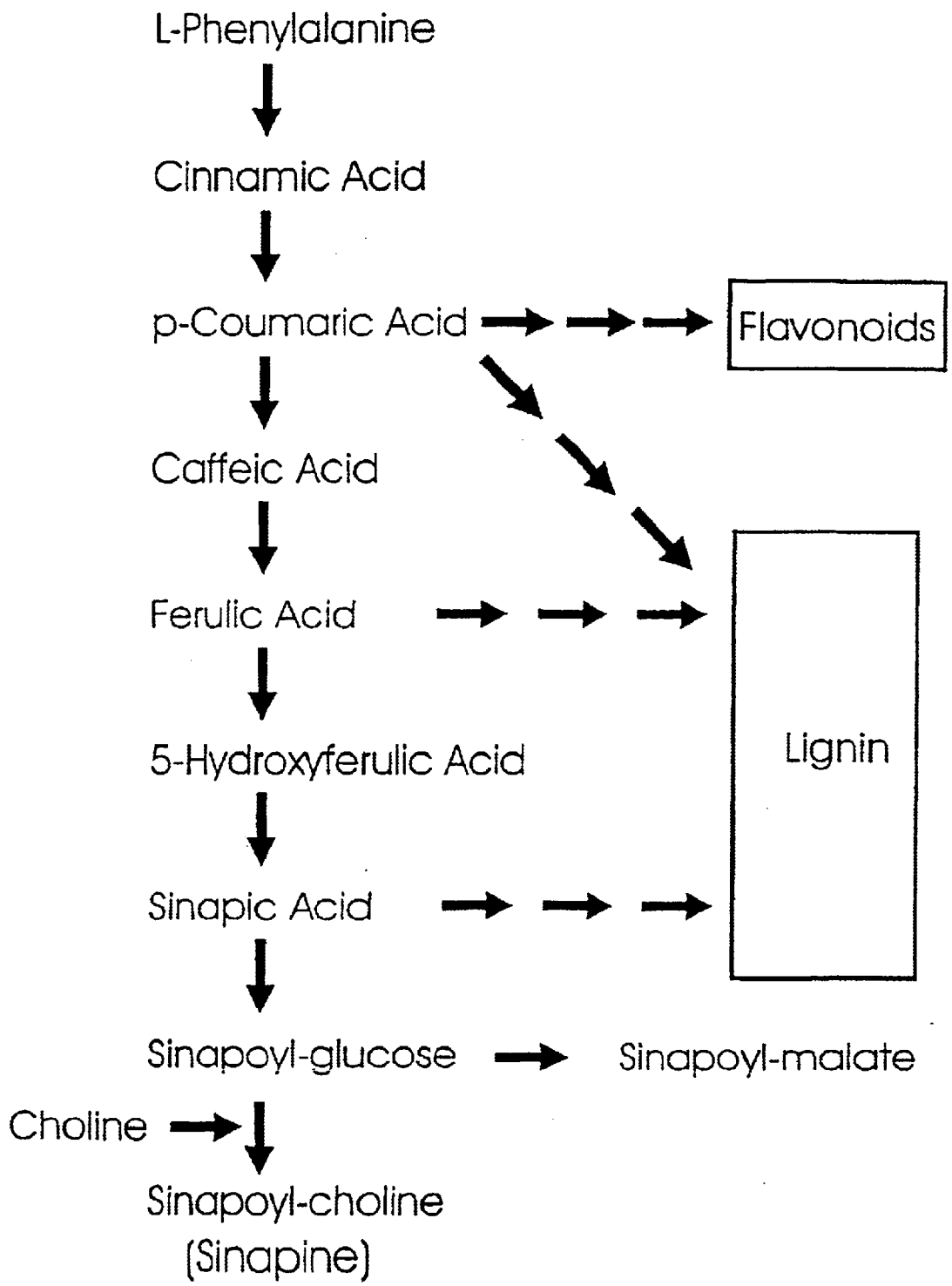

FIG. 2: A schematic representation of general phenylpropanoid metabolism and the production of sinapine.

FIG. 3: The onset and progression of sinapine synthesis in developing seeds. Thin layer chromatography analysis of *Brassica napus* cv Westar seeds.

Figure 4:
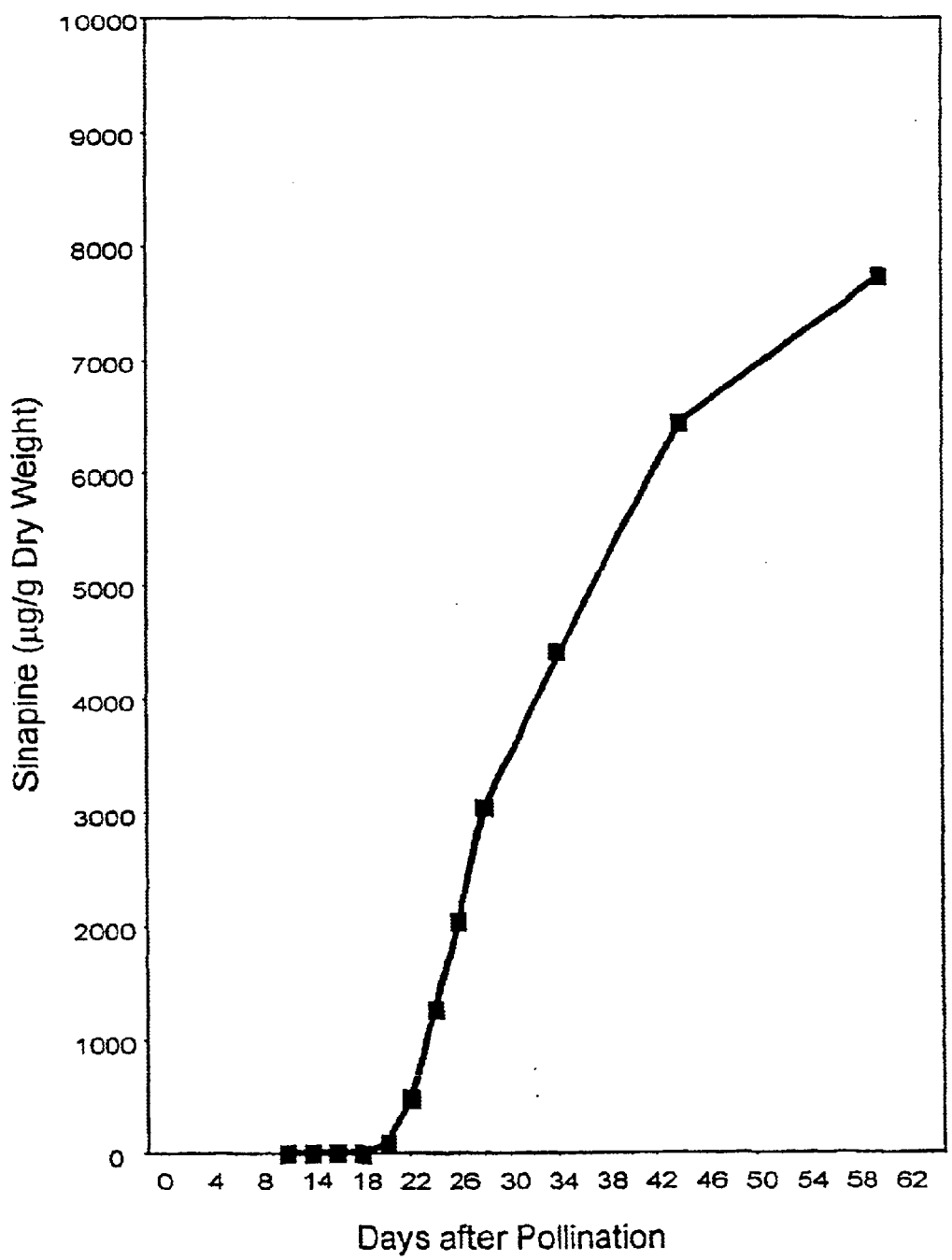

FIG. 4: Quantitative analysis of the accumulation of sinapine in developing seeds by HPLC analysis.

Figure 5:
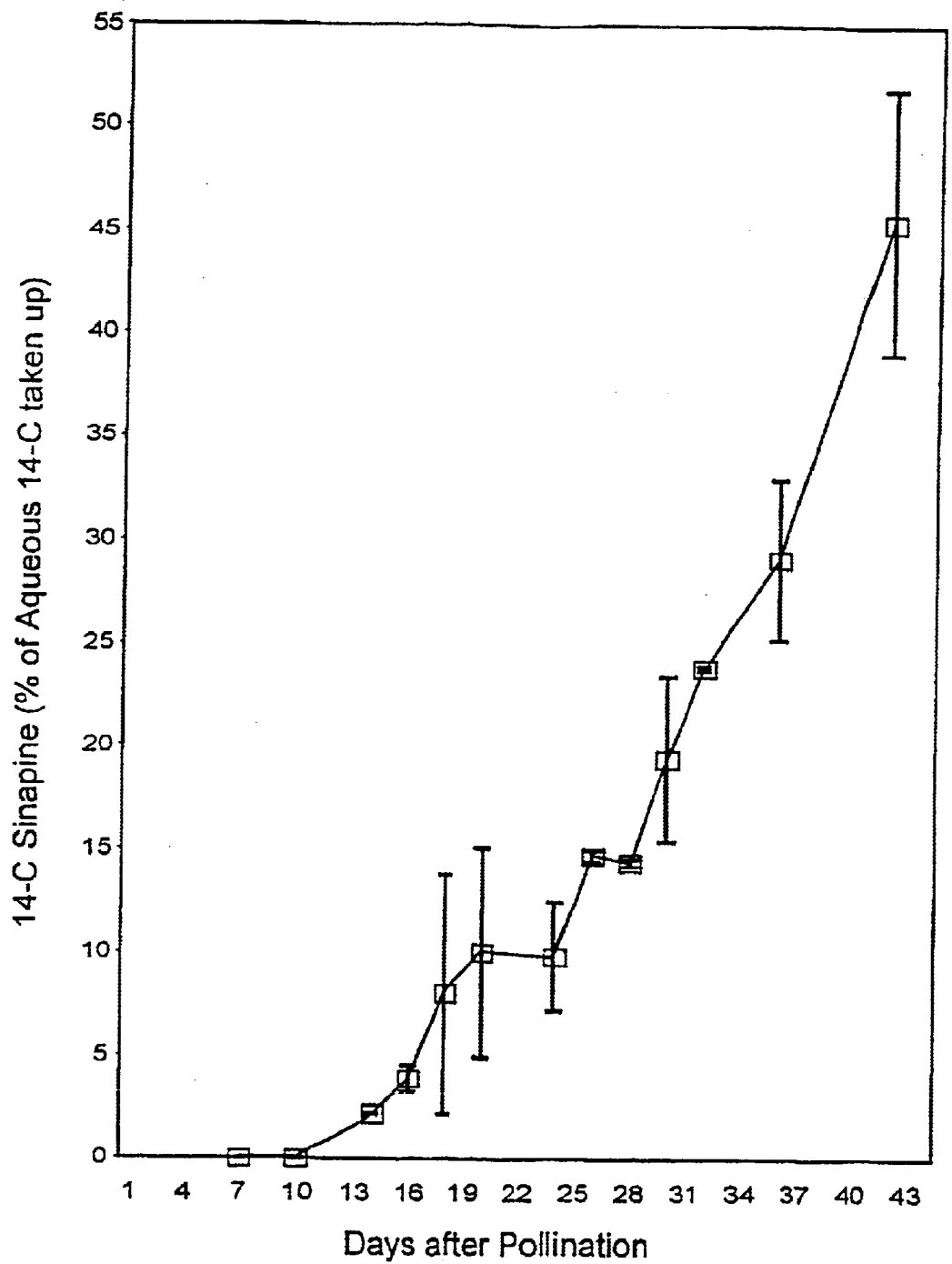

FIG. 5: Determination of the competence of developing seeds to synthesize sinapine by feeding radioactive choline via pedicel of excised siliques, incorporation of label into sinapine from 7 to 43 days after pollination.

Figure 6:
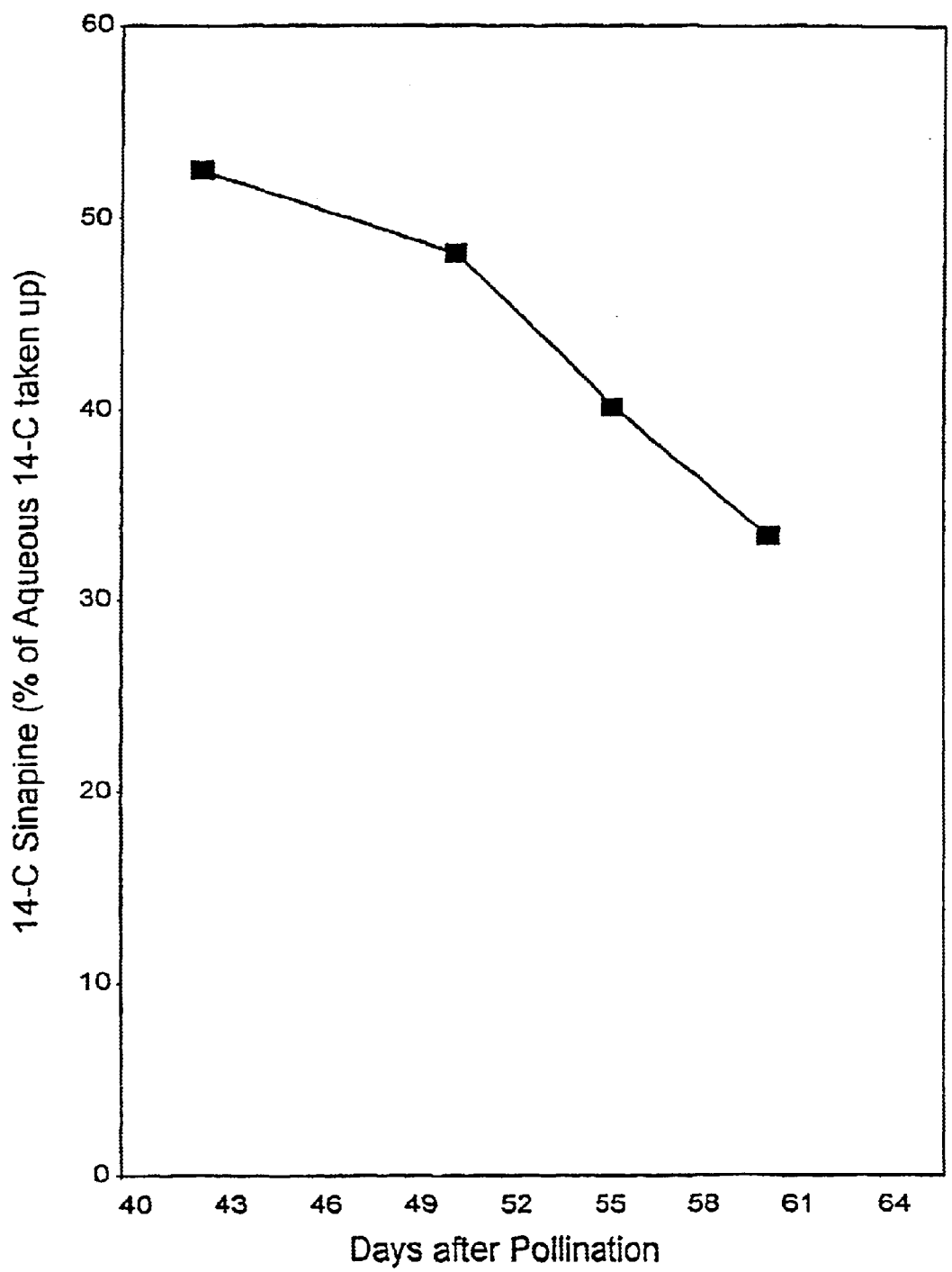

FIG. 6: Determination of the competence of developing seeds to synthesize sinapine by, and infiltrating isolated seeds with, a radioactive choline-containing solution, incorporation of label into sinapine from 43 to 64 days after pollination.

Figure 7:
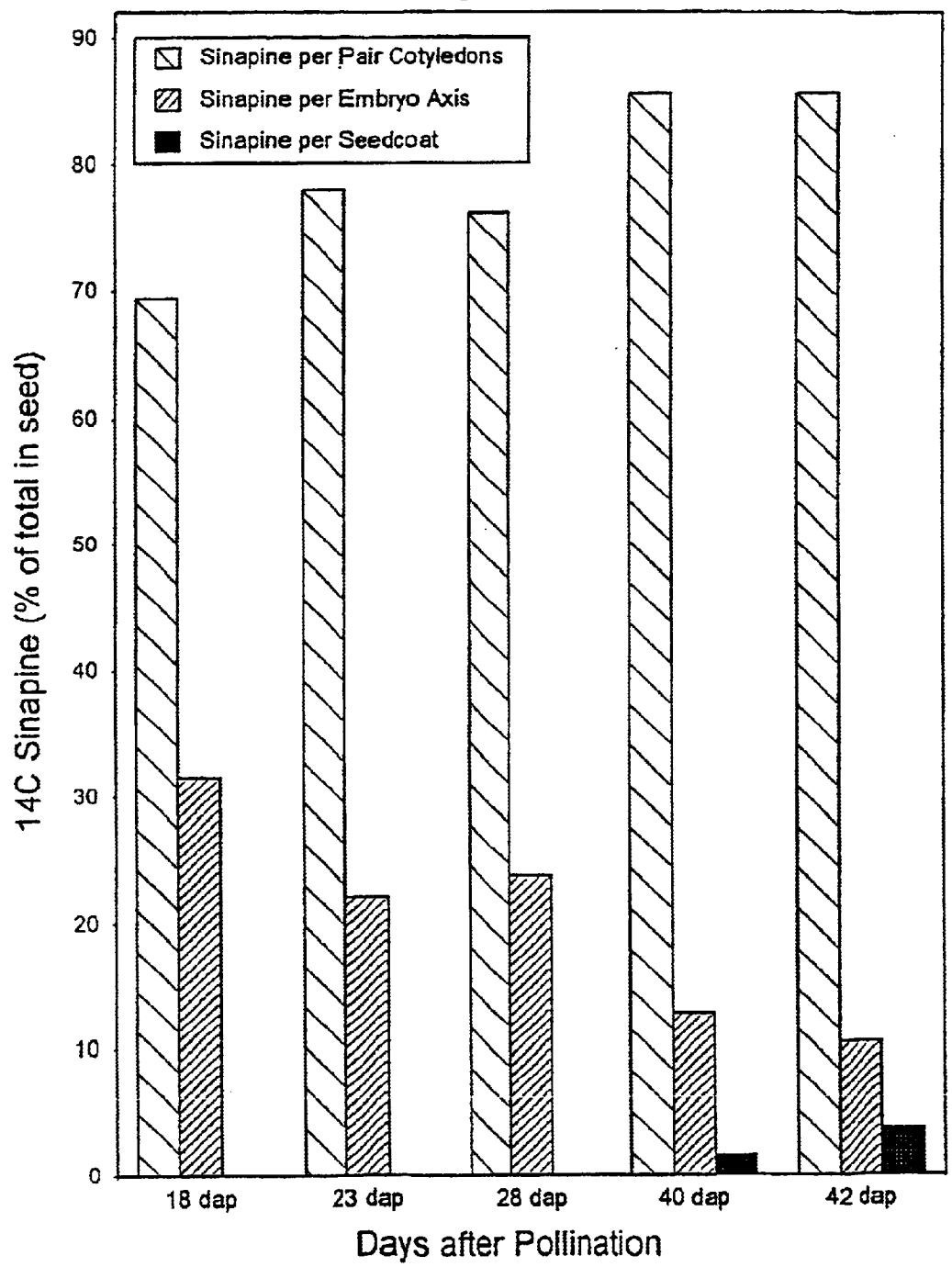

FIG. 7: Accumulation of newly synthesized sinapine in the cotyledon, embryo axes and seedcoat fraction of developing seeds as a fraction of total labelled sinapine in a seed.

Figure 8:
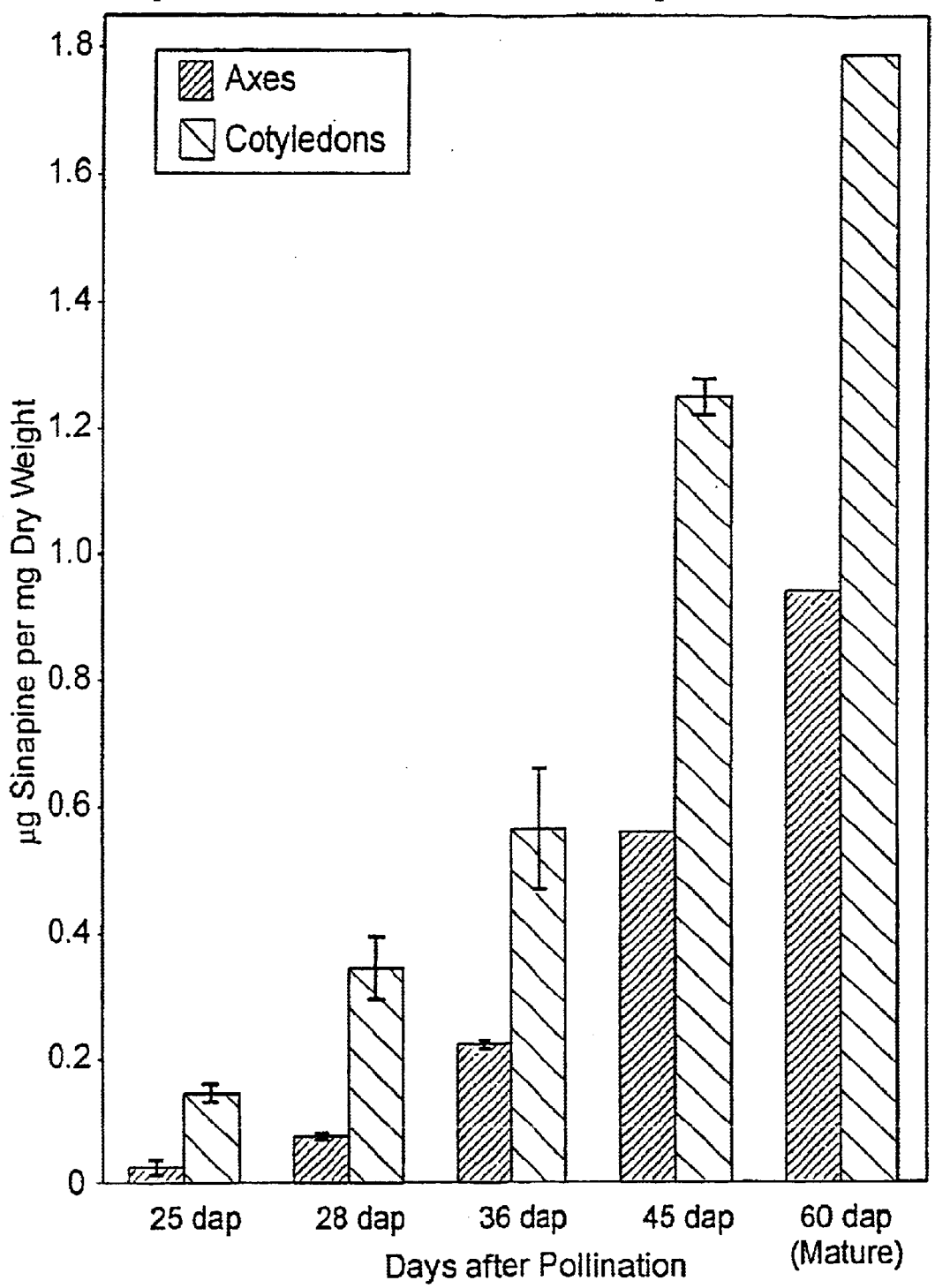

FIG. 8: Sinapine content of the cotyledon and embryo axes components of developing seeds per unit mass of the tissue sample.

Figure 9:
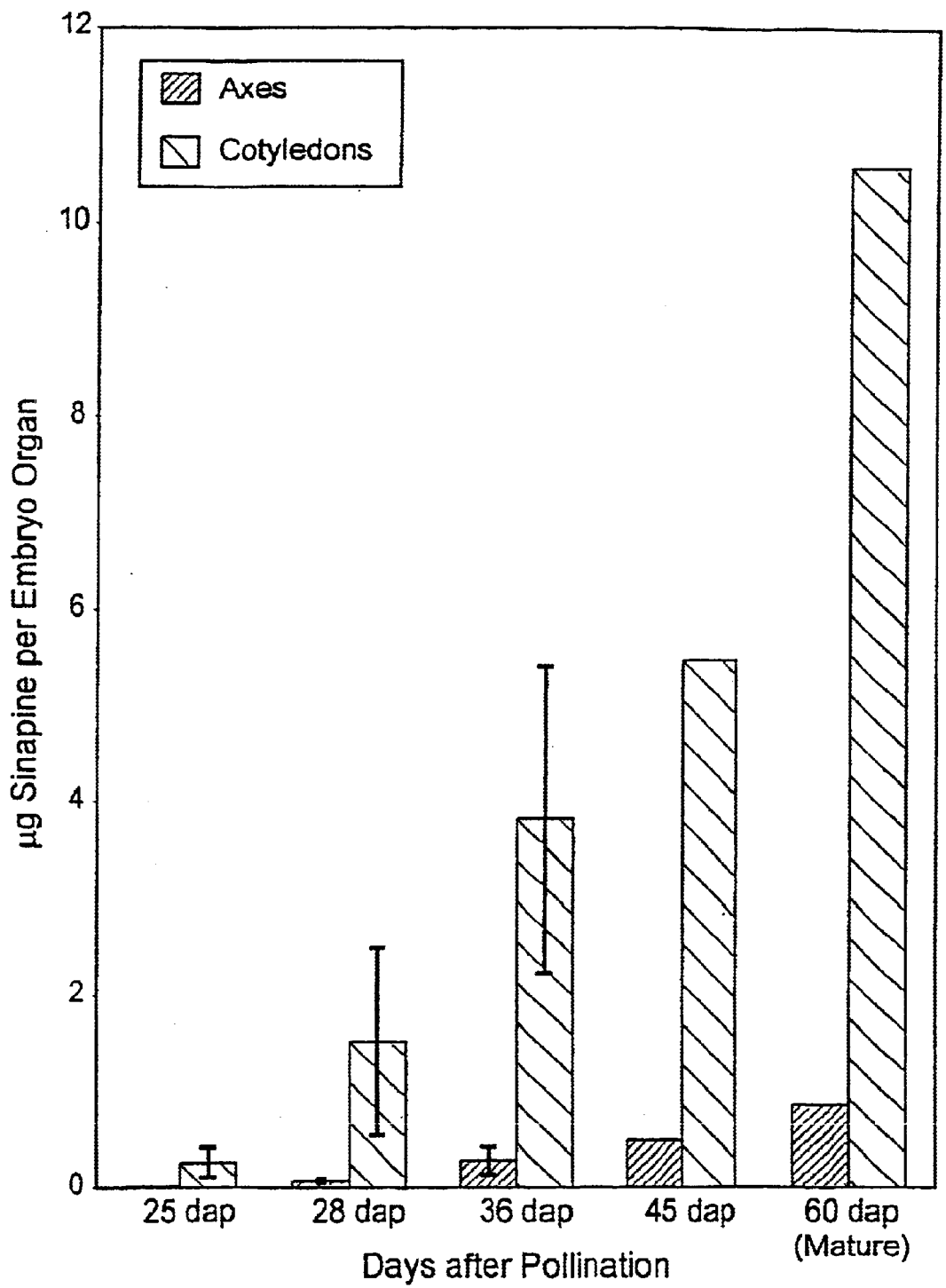

FIG. 9: Determination of the sinapine content of the cotyledon and embryo axis components of developing seeds on a per-seed basis, i.e., the axis or a pair of cotyledons.

FIGS. 10A and 10B: Nucleotide sequence of the choline oxidase open reading frame (SEQ. ID NO: 3).

FIG. 11: Deduced amino acid Sequence of the choline oxidase open reading frame (SEQ ID NO: 4).

Figure 12:
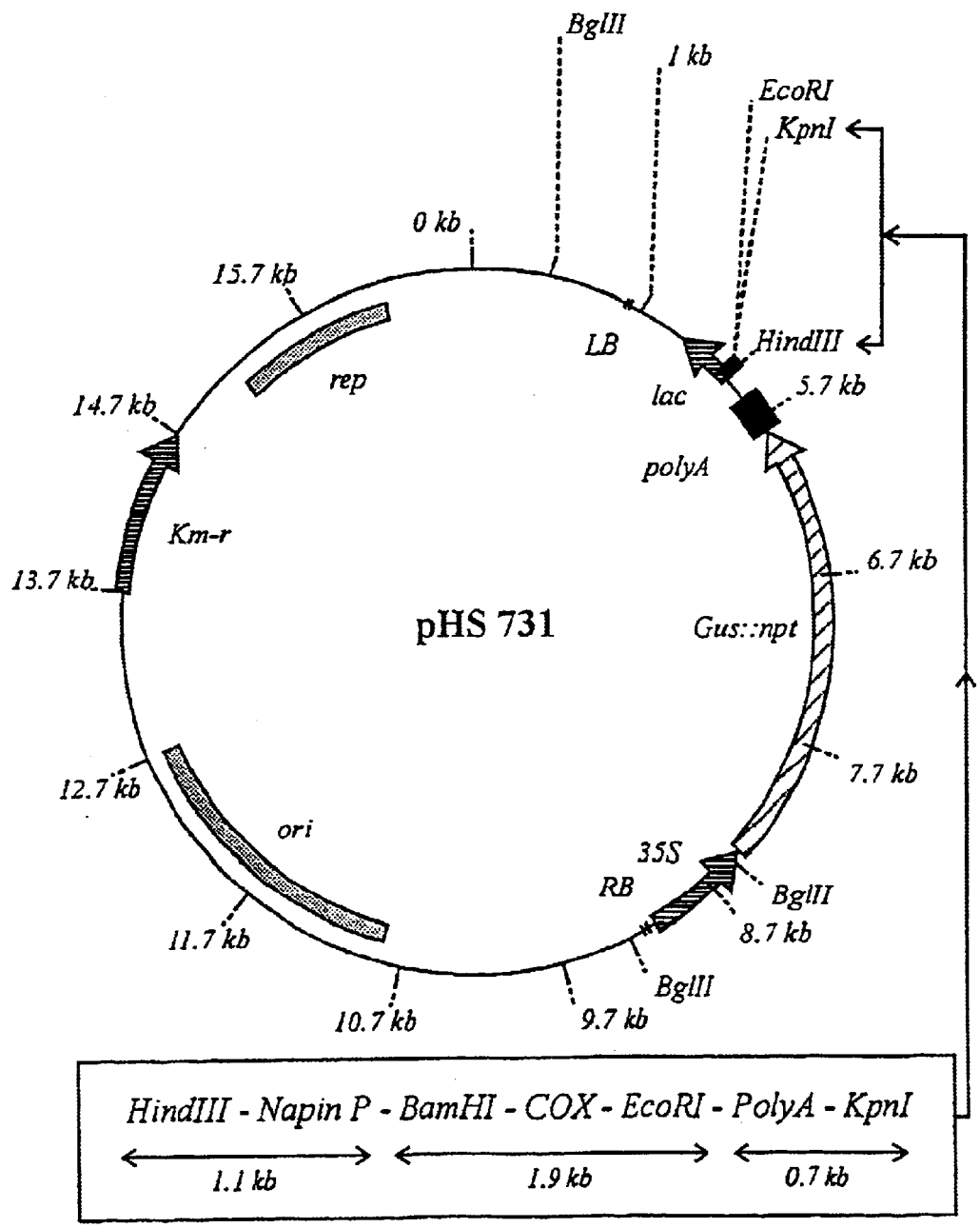

FIG. 12: Diagram of the plant transformation vector pHS 731 containing the COX gene under the control of a tissue selective promoter.

Figure 13:
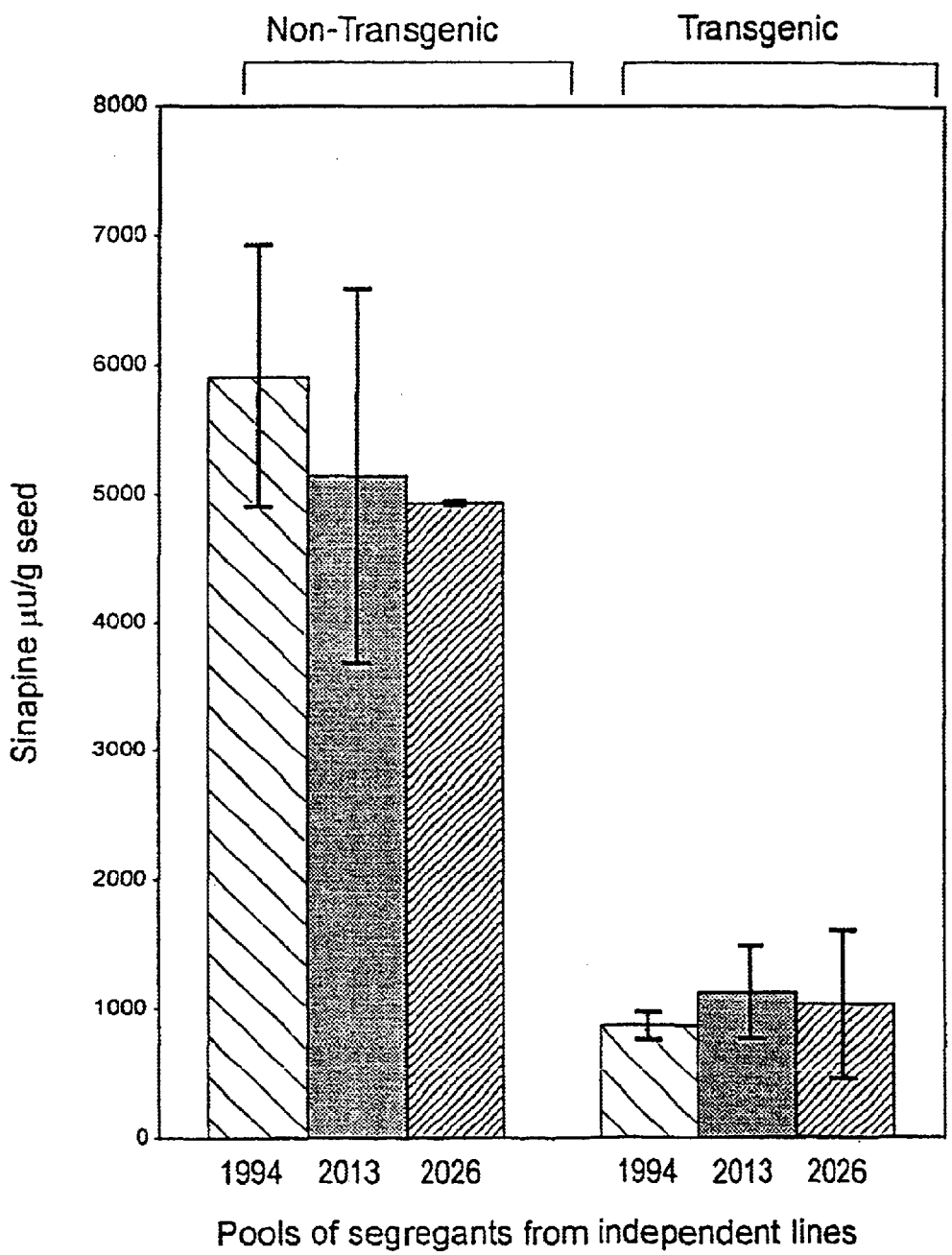

FIG. 13: Reduction of the sinapine content of the seeds in Brassica sp. by expression of the Cox gene.

Figure 14:
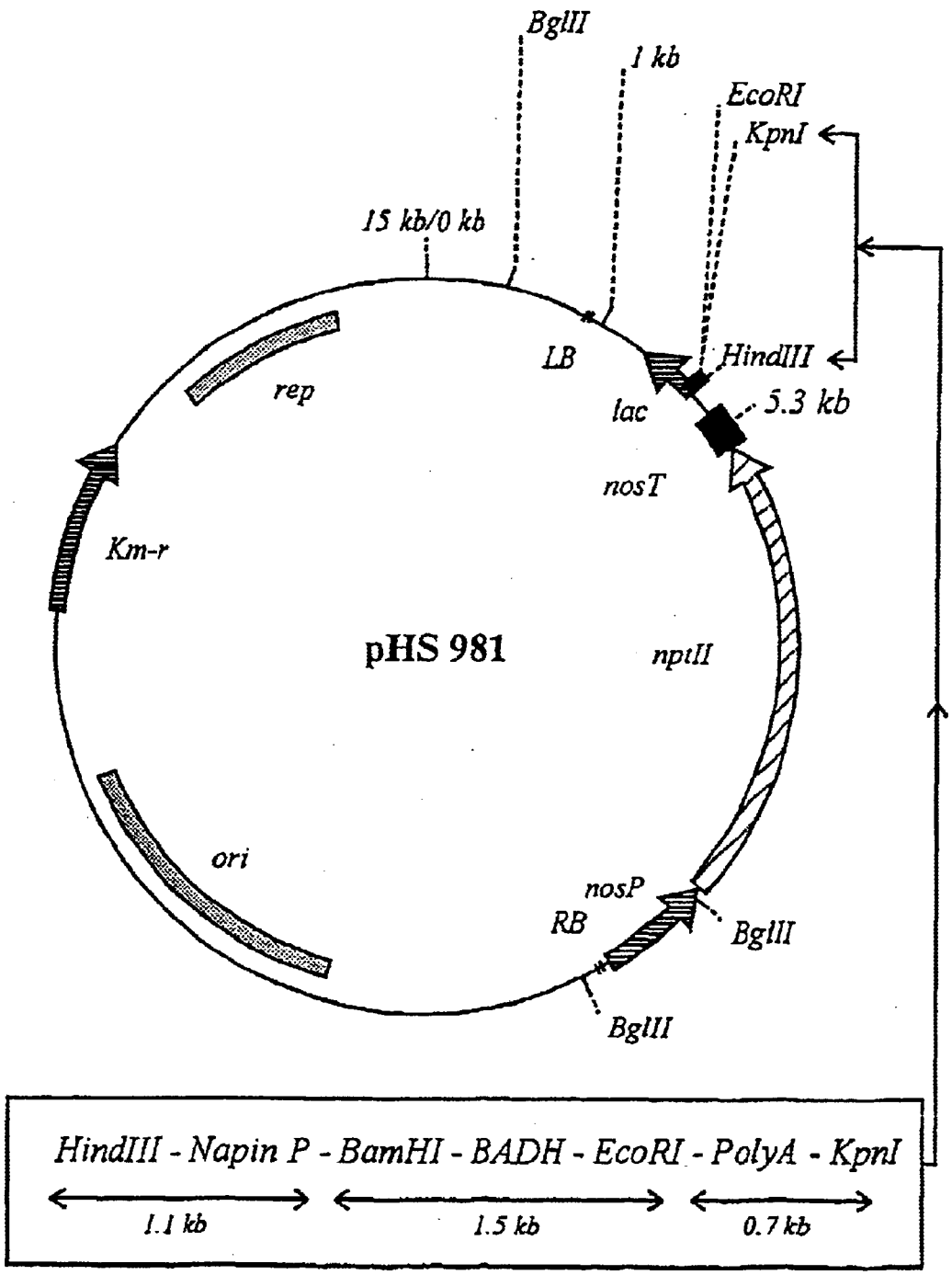

FIG. 14: Diagram of the plant transforation vector pHS 981 containing the BADH gene under the control of a tissue selective promoter.

FIG. 15: Reduction of the sinapine content of the seeds in Brassica op. by expression of the COX and BADH gene.

FIG. 16: Alteration of phenolic content of the seeds in Brassica gp. by expression of the COX and BADH gene.

FIG. 17: Nucleotide sequence of a Synthetic *B. pumulis* ferulic acid decarboxylase gene optimized for epression in plant cells (SEQ ID NO: 1).

FIG. 18: Deduced amino aicid sequence of the protein encoded by the synthetic *B. pumulis* ferulic acid decarbolylase open reading frame (SEQ ID NO: 2).

Figure 19:
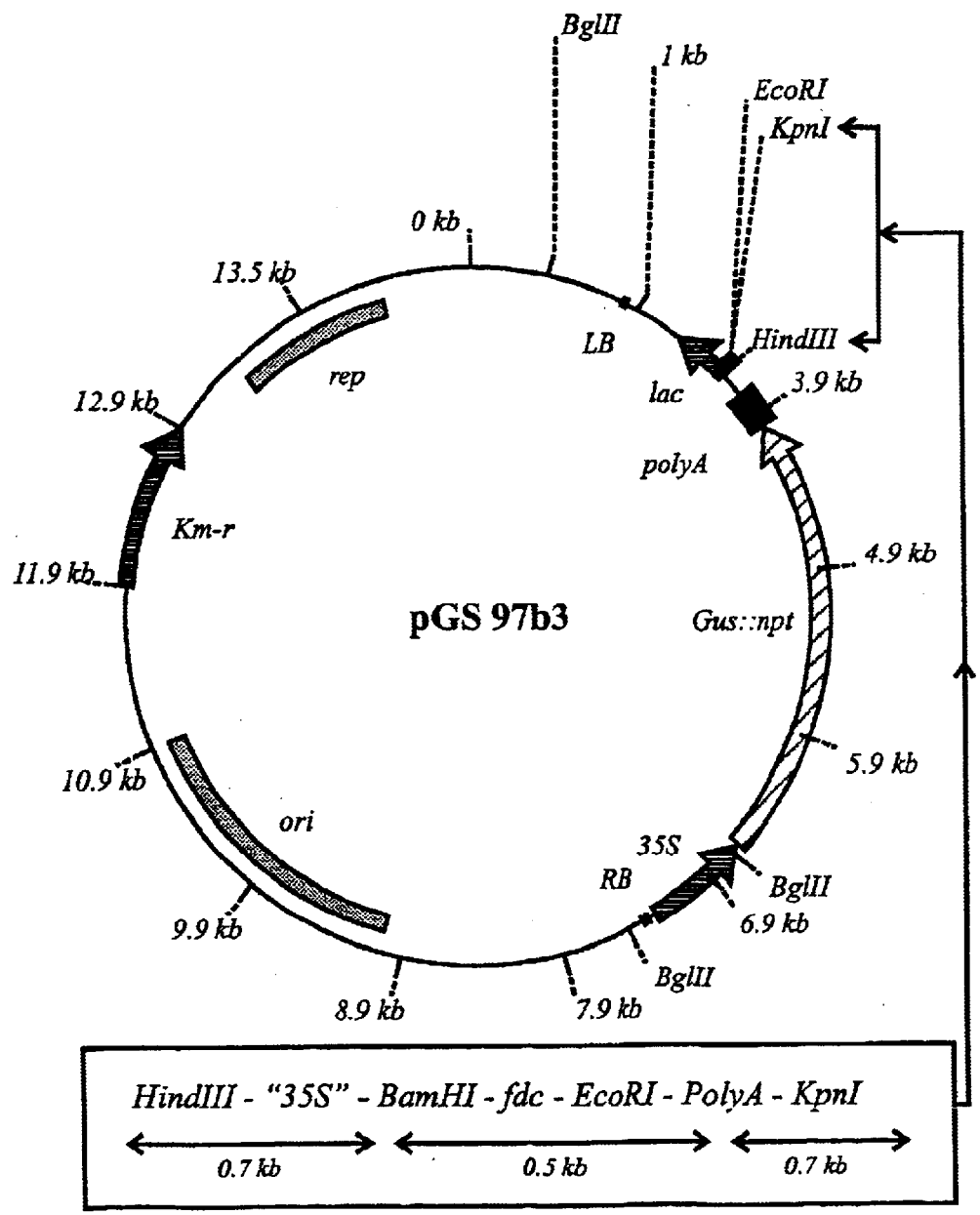

FIG. 19: Restriction tap of a plant transformation vector comprising the ferulic acid decarboxylase gene under the control of the constitutive 35S promoter.

Figure 20:
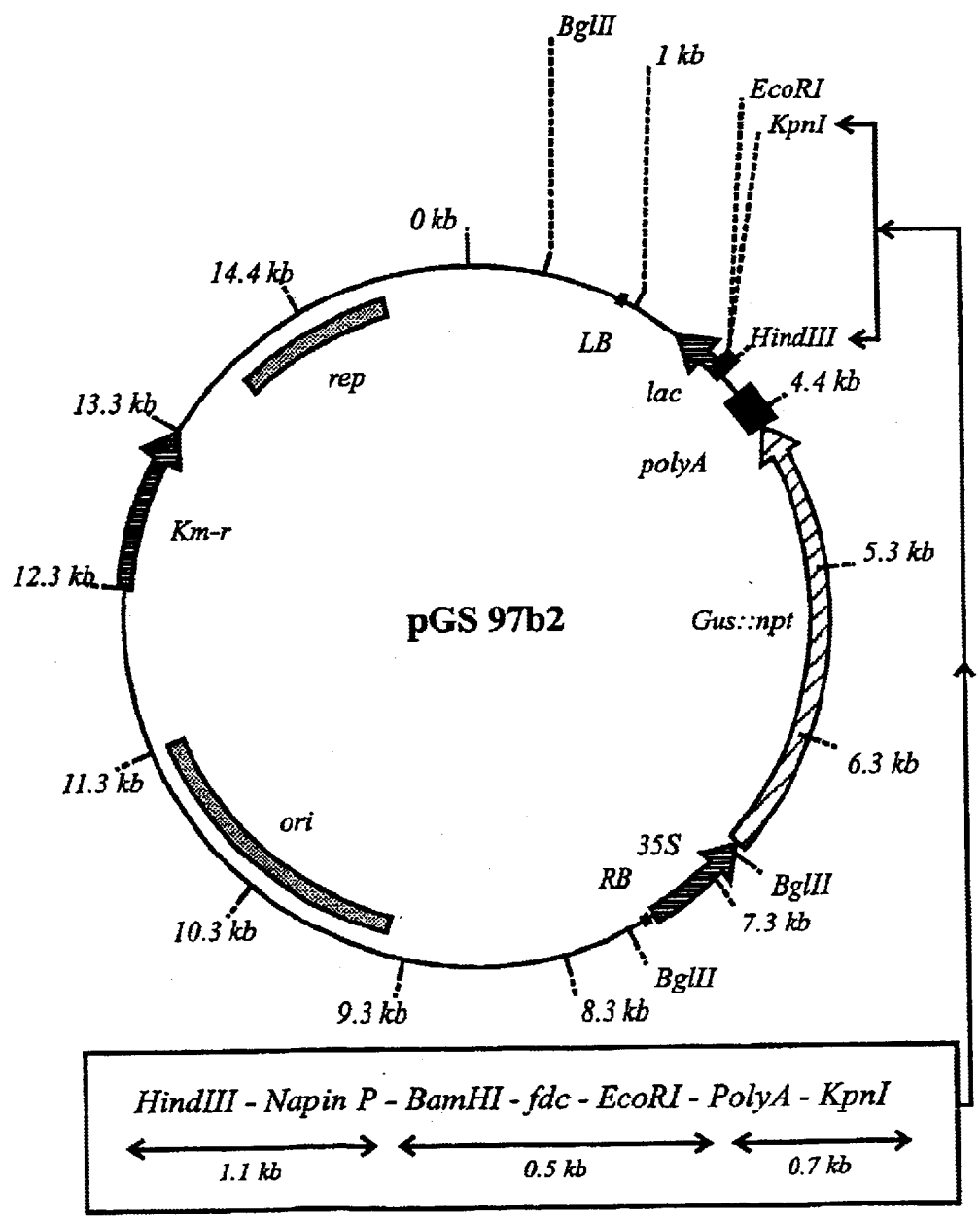

FIG. 20: Restriction map of a plant transformation vector comprising the ferulic acid decarboxylase gene under the control of the seed selective napin promoter.

Figure 21:
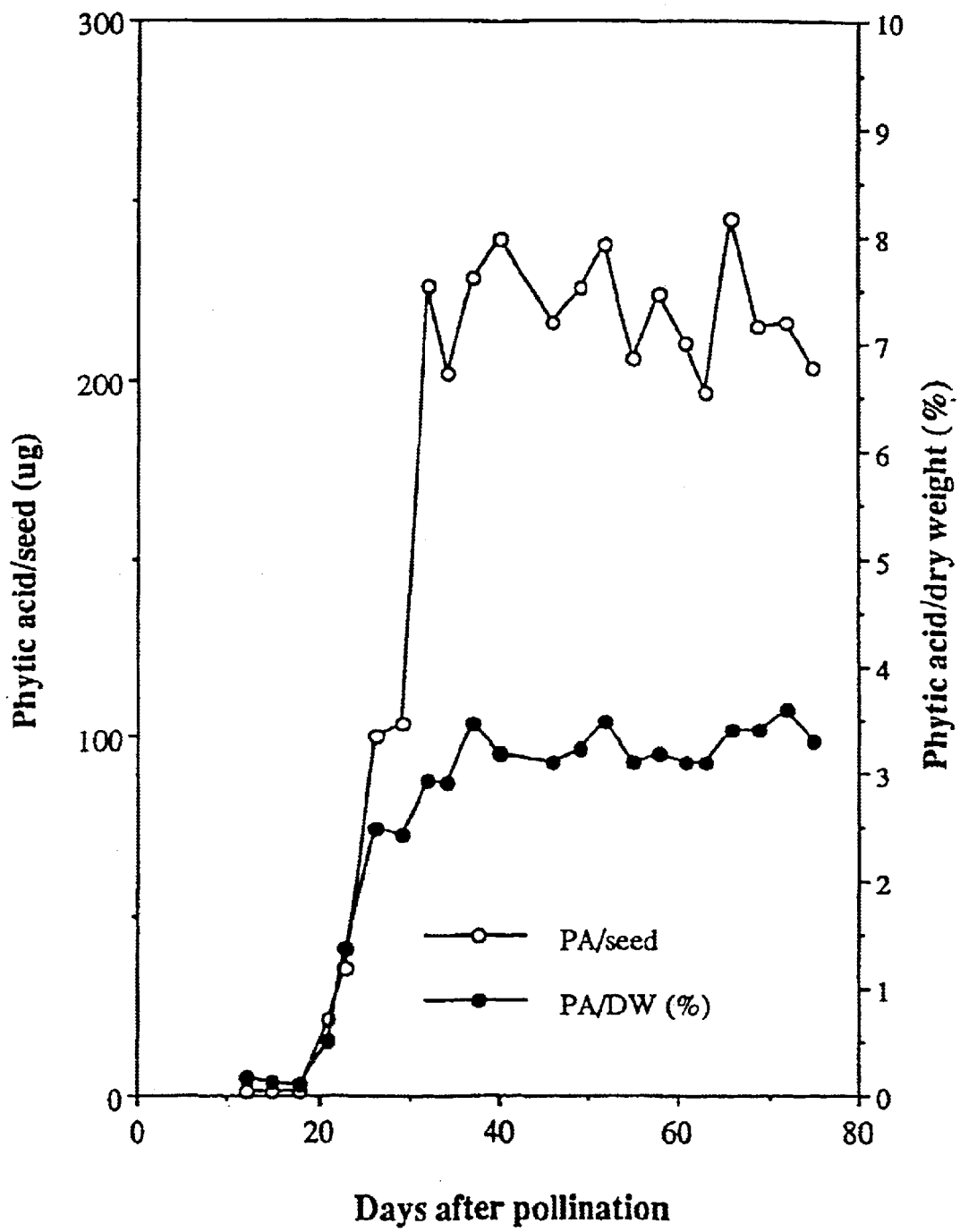

FIG. 21: Phytic acid accumulation during seed development.

Figure 22:
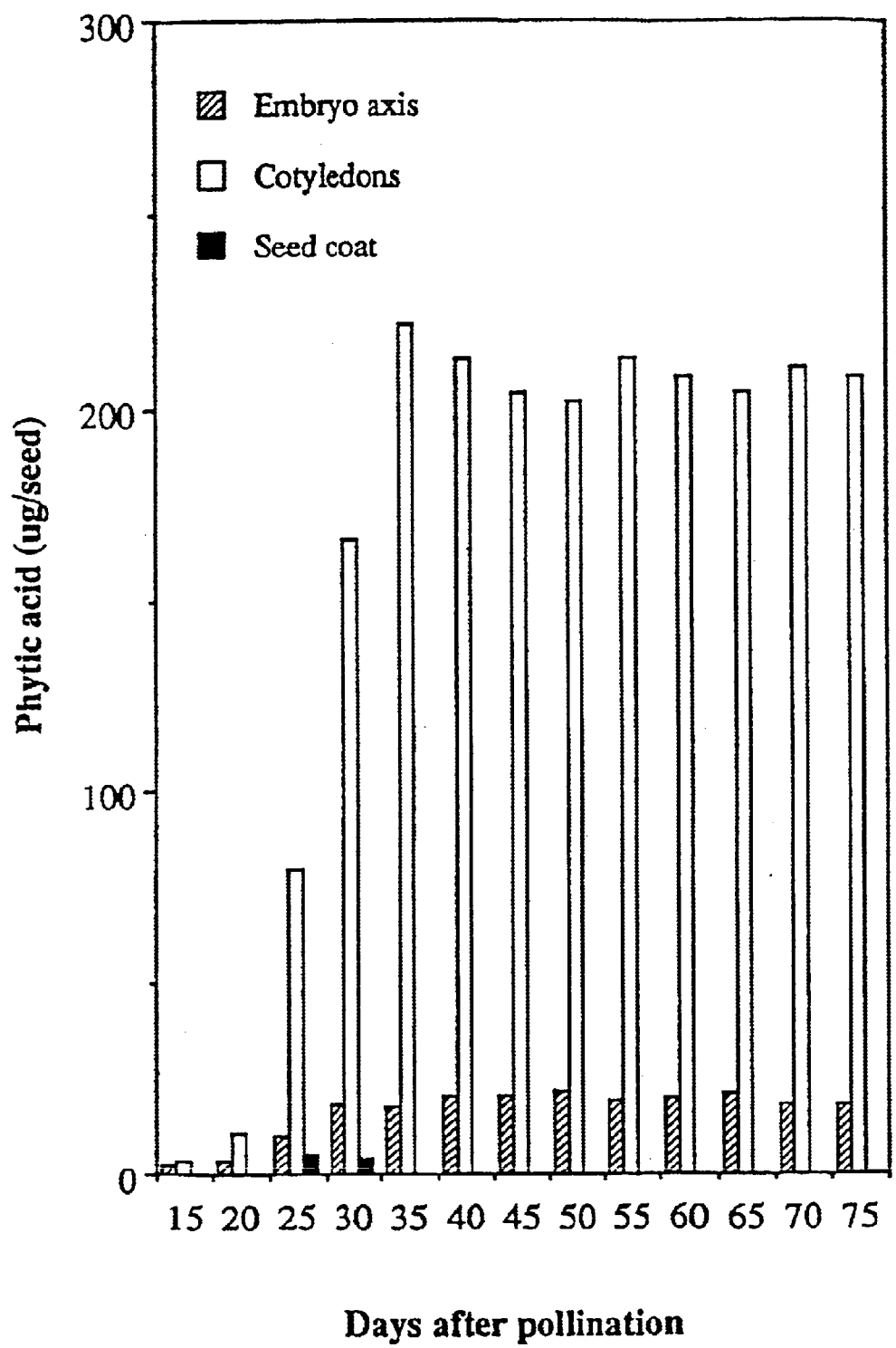

FIG. 22: Tissue specificity of phytic acid deposition in the developing seed.

Figure 23:
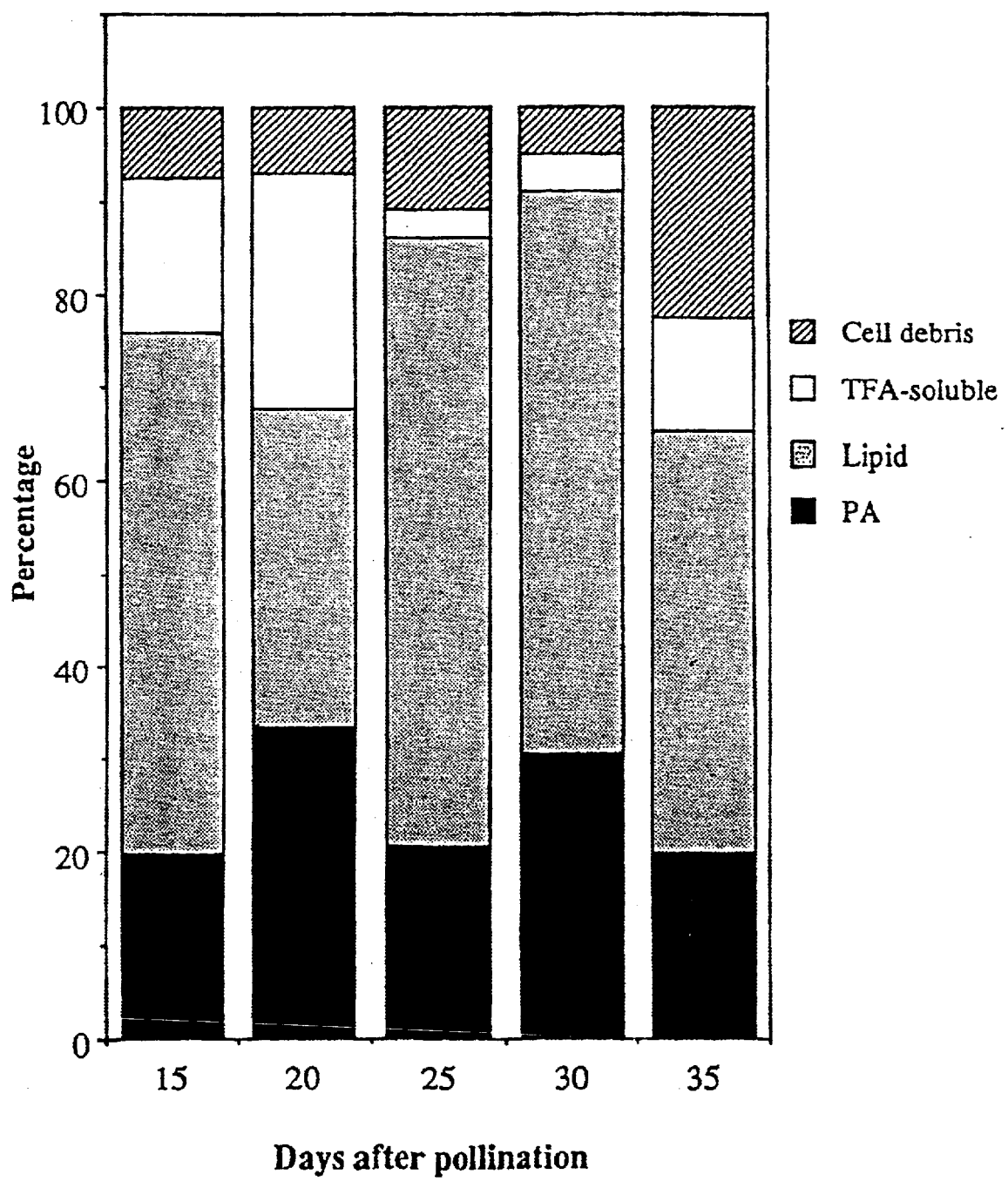

FIG. 23: The percentage of metabolized labelled myoinositol found in phytic acid, lipid, TFA-soluble cell wall and cell debris fractions.

FIG. 24: The sequence of the amplified DNA fragment of the myo-inositol O-methyl transferase gene (SEQ ID NO: 5).

Figure 25:
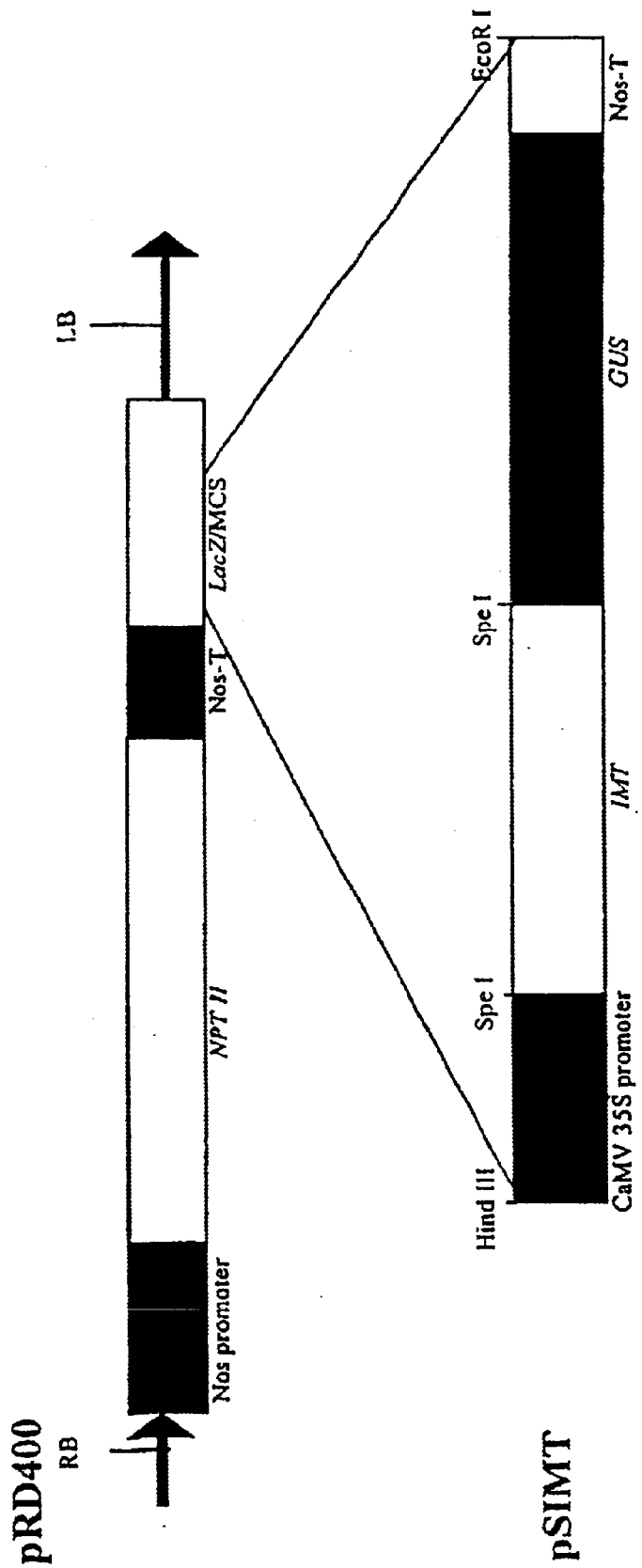

FIG. 25: The restriction map of the vector pSIMT comprising the 35S promoter-IMT-GUS-Nos terminator cassette in pRD400 5.

Figure 26:
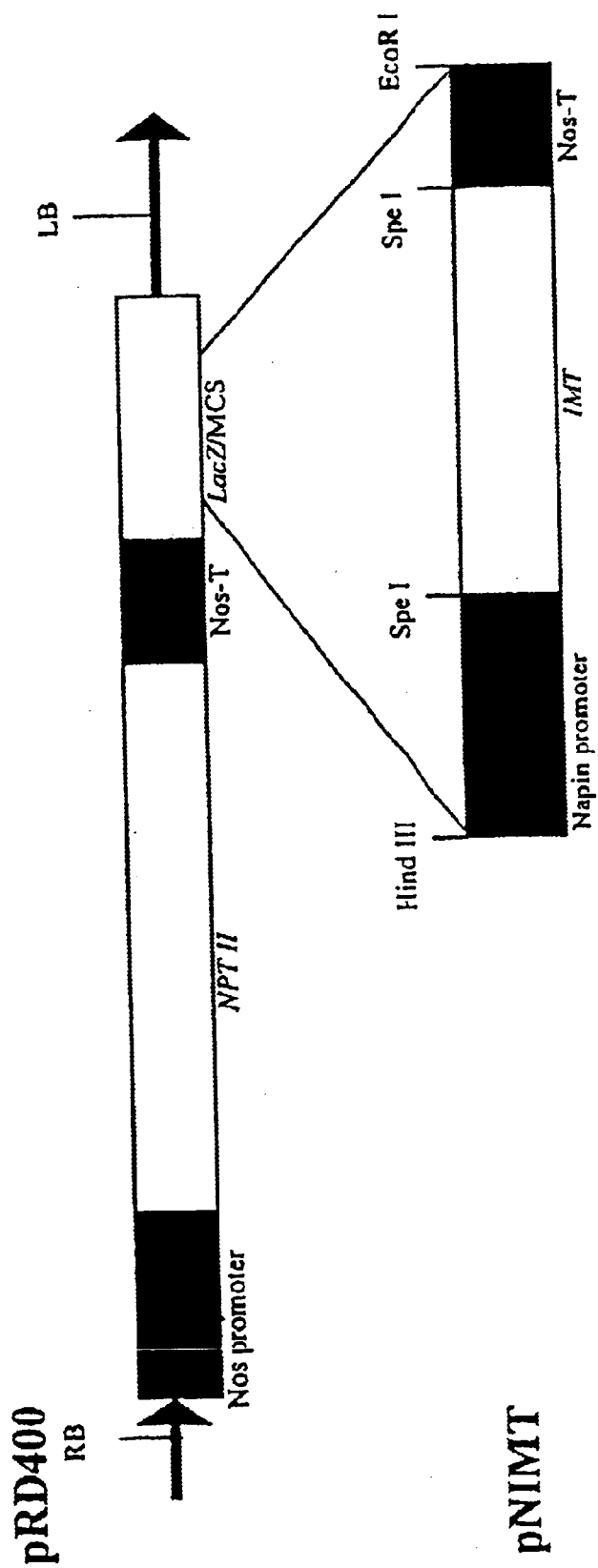

FIG. 26: The restriction map for the vector pNIMT comprising a seed-selective promoter-IMT-GUS-Nosterminator in pRD400.

Figure 27:
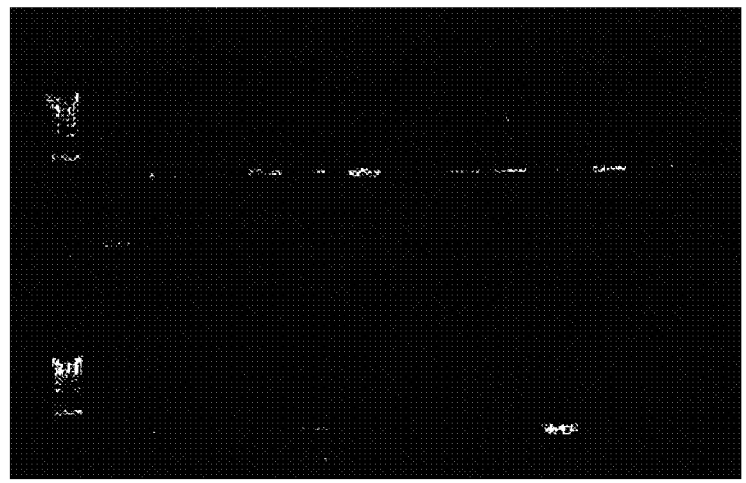

FIG. 27: PCR analysis of transgenic plants containing the IMT gene.

Figure 28:
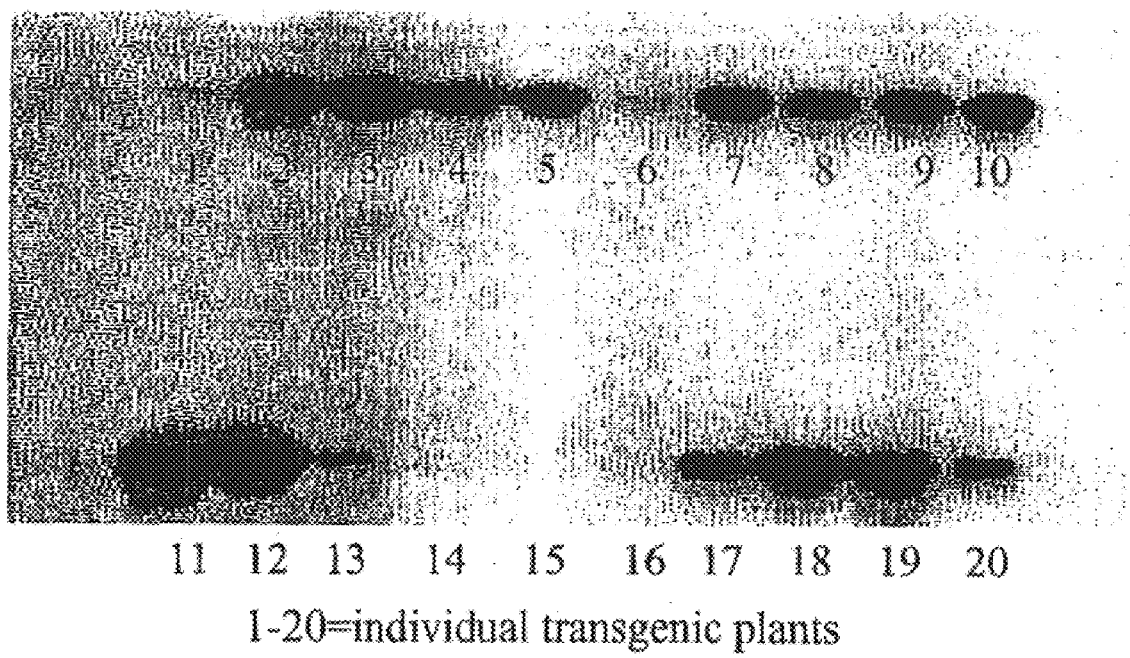

FIG. 28: Northern blot analysis of plants expressing the IMT gene.

Figure 29:
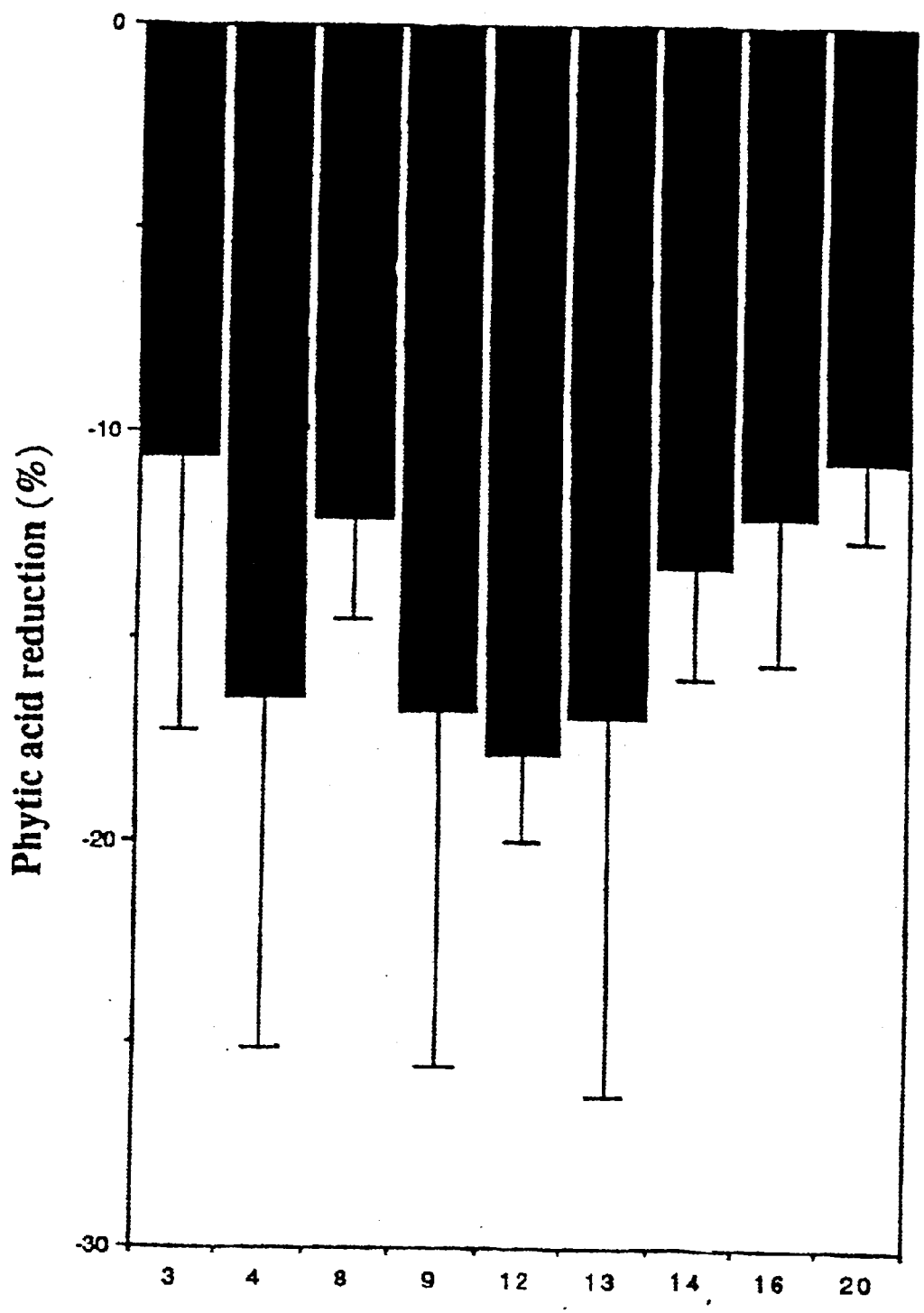

FIG. 29: A bar graph which illustrates the reduction of phytic acid observed in transgenic plants.

FIG. 30: A table that illustrates reduction of phytic acid in F1, F2 and F3 field grown plants containing the vector pSIMT.

FIG. 31: A table that illustrates reduction of phytic acid in F1 and F2 field grown plants containing the vector pNIMT.

DETAILED DESCRIPTION OF THE INVENTION

The present invention relies on the specific reduction or alteration of precursors to products of secondary metabolism that are distinct from primary metabolites. In this fashion the potential deleterious effects of altering primary metabolic pathways to achieve a similar result are avoided. Thus the present invention avoids the manipulation of compounds that could be considered as primary metabolites.

In an preferred application, the availability of substrate is altered by employing an enzyme, for example one which is heterologous to said plant cell, capable of acting upon said substrate, and which removes the substrate from or modifies the availability of the substrate in the available pool of substrates. A generalized overview of the method and the relationship of primary and secondary metabolism is shown in FIG. 1. The use of a heterologous enzyme activity to alters the flow of products in the secondary metabolic pathway leads to a modification of a desired target secondary metabolite. This alters the flow of products in the secondary metabolic pathway, leading to a modification of a desired target secondary metabolite. By doing so, the level of end-product of certain enzymatic steps within the secondary metabolic pathway are lowered, whereas, in contrast, for other steps in the pathway, product accumulates to high levels, inhibiting the enzymes responsible for producing said product. This feedback inhibition in turn influences the production of the final end-product from the entire secondary metabolic pathway. Thus changes in the levels of products of a specific secondary metabolic pathway and associated pathways are achieved by introducing novel enzymatic activities which alter the flow of biochemicals (e.g. substrates and products thereof) through the pathway. Heterologous enzymes have been expressed in plant tissue, causing the metabolic diversion of precursors within these pathways into substances that accumulate without detrimental effects in the plant cell.

In some embodiments, valuable products or products with beneficial effects to the plant cell are formed as a result of this method.

In one embodiment, the targeted precursor is then modified by the addition of a novel enzyme activity. One preferred aspect of the invention contemplates the selection of an enzyme having activity heterologous: to the plant cell in which it is expressed. For example, the enzyme is one which is not normally associated with the secondary metabolic pathway at issue in the plant cell. The enzyme used can be of plant, animal or microbial origin and it can be modified for proper expression in plant cells. The selected heterologous enzyme is capable of modifying the precursor to alter its availability for the formation of the secondary metabolite. By using an enzyme activity heterologous to the cell in which it is expressed, the normal biochemical control mechanisms are bypassed and secondary metabolism is altered in a predictable fashion. Of particular interest within the scope of the present invention is modification of the products of the secondary metabolic pathway related to sugar alcohols and the phenylpropanoid secondary metabolic pathway.

Additional examples of the utility of the present method are found in the alteration of levels of modified sugar compounds such as galactose and anti-nutritional sucrosyl glycosides such as stachyose and raffinose. Galactose is converted to galactinol that is one of the precursors for the formation of these anti-nutritional sucrosyl glycosides. The precursor form of galactose is the conjugated form referred to as UDP-galactose. As a method contemplated within the present invention, the formation and accumulation of UDP-galactose (and subsequent conversion to galactinol) is prevented by utilizing an enzyme activity heterologous to plant cells, said enzyme capable of altering the levels of UDP-galactose. The enzyme UDP-galactose 4-epimerase (galE) is involved in one of the major steps of galactose metabolism in living systems. It catalyzes the conversion of UDP-galactose into UDP-glucose. The gene for the enzyme is available from human, yeastand bacteria. In the present invention, use of a bacterially encoded enzyme is contemplated.

As a consequence of the expression of this heterologous enzyme in a plant cell, the availability of UDP-galactose would be reduced and a beneficial compound, UDP-glucose would be produced. It is fully believed that expression of the enzyme UDP-galactose 4-epimerase would lead to reduced biosynthesis of galactinol, which is one of the precursors of the anti-nutritional sucrose glycosides. In addition to reducing the accumulation rate of the undesirable sucrose glycosides the activity of the newly introduced enzyme would lead to enhanced availability of UDP-glucose and subsequently the formation of sucrose. The latter will be expected to participate in, and enhance the activity of other metabolic pathways where sucrose is needed either for acarbon source for enhanced plant productivity (e.g. proteins, lipids, overall yield, etc.) or directly as accumulated sucrose.

Still other applications of the method can be contemplated within the scope of the present invention. It is possible to alter the levels of various sugar derivatives such as glucose-1-phosphate and glucose-6-phosphate by using the enzyme phosphoglucomutase (pgm). This enzyme catalyzes the interconversion of glucose-1- and glucose-6-phosphate (G-1-P, G-6-P) in the synthesis and consumption of sucrose. The enzyme plays a pivotal role in the synthesis and utilization of sucrose, starch and glycogen, and is present in all organisms. The gene for this enzyme is available from a variety of eukaryotic as well as bacterial sources,(e.g. Agrobacterium).

G-6-P is a major starting material for a number of sugar interconversions, one of which is the synthesis of myo-inositol-1-P. The latter is a major substrate and co-factor-in the synthesis of phytic acid and the anti-nutritional sucrosyl glycosides respectively. Expression of the enzyme could be expected to lower the level of G-6-P that would translate into lower levels of the anti-nutritional factors mentioned above. Thus various metabolic alterations can be contemplated within the scope of the present invention.

The method is not restricted to any particular secondary metabolic pathway. Nor is the method restricted to any particular plant species. Rather, the method can be applied to alter secondary metabolic pathways common to many commercially valuable crop species, including monocots and dicots, or to target a secondary metabolite having unique significance to a specific crop.

The biochemical basis for the method of the present invention is founded on the concept of the regulation of enzyme activity by the availability of substrates. In general, enzymatic rates are influenced by the availability of substrates. In other words, an enzyme will produce product at a rate proportional to the amount of available substrate. The reduction of substrate concentration leads to lower levels of product. Furthermore, many enzymes are subject to end-product inhibition, meaning the enzymatic rate is reduced in the presence of a large excess of the final product. Hence, by altering the levels of available substrates or enzymatic products, the overall production of compounds produced by a biochemical pathway can be changed.

Examples of secondary metabolic pathways that may be altered by the present invention include isoprenoid biosynthesis, alkaloid biosynthesis, terpenoid biosynthesis, phenolic biosynthesis, sugar alcohol biosynthesis, or any other secondary metabolic pathway that produces compounds of anti-nutritional or commercially valuable nature. Specific secondary metabolites that may be modulated by the present invention include anti-nutritional phenolic compounds such as sinapine or glucosinolates in crucifers, sugar alcohol products such as phytic acid or stachyose and raffinose, gossypol in cotton, nicotine, chlorogenic acid, condensed tannins or any other anti-nutritional secondary metabolite. The compound chlorogenic acid is common in soybean, cotton, sunflower and is derived from caffeic acid, a compound produced within the phenylpropanoid pathway. Still other anti-nutritional compounds include saponins, anti-nutritional compounds found in many plants, including alfalfa. Saponins are high-molecular-weight glycosides, consisting of a sugar moeity linked to a triterpene or steroid aglycone. There are at least three classes of saponins known, triterpene glycosides, steroid glycosides and steroid alkaloid glycosides. The biosynthesis of saponins in plants involves the starting material squalene. Other important classes of secondary metabolites such as phytosterols, cardenolides, cucurbitacins, quassinoids and limonides are also derived from squalene. Excess saponins in animal diets are associated with the condition known as bloat.

The present invention in exemplified by demonstration of the utility of the method in a number of unrelated secondary metabolic pathways. However, the utility of the method for modifying any plant secondary metabolic pathway will be evident to the skilled worker and a general method to carry out the invention is provided.

In one embodiment, the present invention provides methods and DNA compositions for the alteration of sinapine content and related phenolic compounds in plants. In another embodiment, the invention provides plant cells modified in phenolic content and plant seed with reduced phenolic content, particularly cruciferous plants with reduced sinapine content. In another embodiment, the present invention provides methods and DNA compositions for the alteration of phytic acid content in plant cells, a product of the sugar alcohol secondary metabolic pathway. In another embodiment, the invention provides plant cells modified in phytic acid content and plant seed with reduced phytic acid. In another embodiment, the invention provides plant seeds with reduced phytic acid content suitable for feed applications, plant seed with reduced phytic acid content suitable for preparation of modified meal and plant cells with a modified sugar alcohol (inositol) metabolism.

Each secondary metabolic pathway in plants has associated with it a limited number of enzymes and substrates for these enzymes that are unique or used in a unique fashion. The secondary metabolic pathway may produce various compounds that are used or present throughout the plant. Thus as a means to alter secondary metabolism, unique enzyme activities are used to specifically alter the flow of compounds through the specific pathway. In order to provide an illustration of the utility of the method, two distinct secondary metabolic pathways were modified according to the method of the present invention. Information on these pathways that helps provide a full understanding of the nature of the method is provided below.

(A) Secondary Metabolic Pathway for Phenylpropanoid Metabolism

Plants produce a variety of phenolic compounds by way of the phenylpropanoid pathway, a secondary metabolic pathway. Phenylpropanoid metabolism has been implicated amongst many physiological processes in plants including disease resistance, UV light protection and plant growth regulation. The products of this pathway are required for suberin and lignin biosynthesis, which are components of plant tissues and are involved in the formation of plant fibre, a general term that relates to under-metabolized carbohydrate in the seed or seed meal. Lignin is believed to be involved in the formation of insoluble fibre and hence high levels of lignin in seed or meal is correlated with inefficient utilization of meal or seed, particularly in monogastric animals. Hence plant phenols, particularly the phenolic precursors of lignin, can be considered as anti-nutritional factors for animal feed, and reduction or appropriate alteration of plant phenols, particularly phenols used in lignin formation, can provide a meal that is superior.

Plant phenols also are involved in the formation of various other compounds, some of which are also antinutritional in nature.

The present invention provides a means to reduce specific phenolic compounds that are considered anti-nutritional in plant cells, seed or meal used for feed. In particular, the present invention contemplates the reduction of the bitter flavoured anti-nutritional compound sinapine (or sinapoyl choline) in plant cells that produce it. Sinapine is also oil thought to complex with proteins in meal, reducing the availability of protein for digestion and utilization by the animal. The bitter taste may also affect feeding levels. Additionally, when fed to some strains of hens laying brown-shelled eggs, sinapine causes an unacceptable fishy odour in the eggs. The ratio of sinapine-containing meal in these cases needs to be held below ca. 10%, and this limits the use of meal containing sinapine in these feed formulations. Hence reduction of sinapine in seed or seed meal from crucifers is an important commercial objective.

The production of sinapine occurs as an extension of the phenylpropanoid pathway. The pathway defined within the scope of the present invention includes the biochemical steps that lead to the formation of sinapic acid as well as the biochemical pathways that branch from various steps such as the branch pathways leading to the formation of lignin monomers and other biochemicals derived from products of the phenylpropanoid pathway.

In the phenylpropanoid pathway, L-phenylalanine, an aromatic amino acid, is a substrate for the enzyme phenalanine ammonia lyase (PAL). The enzymatic activity of PAL leads to the formation of cinnamic acid which is a substrate for cinnamate-4-hydroxylase (C4H). The product of C4H is p-coumaric acid which is a precursor for many flavanoid compounds, some of which may also be formed from L-tyrogine by the action of the enzyme tyrosine ammonia lyase (TAL). Coumaric acid may also serve as a precursor for lignin biosynthesis. The enzyme p-coumarate-3-hydroxylase (C3H) acts on p-coumaric acid to form caffeic acid. Caffeic acid is metabolized by caffeate/5-hydroxyferulate-O-methyltransferase (OMT) to form ferulic acid. Ferulic acid is one of three known primary phenolic monomers used for lignin biosynthesis. Ferulic acid can also be a substrate for the enzyme ferulate-5-hydroxylase (F5H) forming 5-hydroxyferulic acid, which can be further modified by the enzyme OMT to form sinapic acid. Sinapic acid is the other major phenolic lignin monomer. Sinapic acid can also be conjugated to form sinapoyl glucose by the action of the enzyme UDP-glucose sinapoyltransferase (SGT). Sinapoyl glucose serves as the substrate for sinapoyl glucose:choline sinapoyl transferase (SCT), leading to the formation of sinapoyl choline or sinapine. These latter two steps are prevalent in crucifers and in Brassicas the accumulation of sinapine in the seed represents the major non-polymeric phenolic compound found in mature seed. A generalized pathway for phenylpropanoid metabolism is shown in FIG. 2. It should be noted that additional enzymatic activities may be part of the phenylpropanoid pathway in certain plant species.

Sinapine or sinapoyl choline is the most abundant phenolic compound in crucifer seeds, and in *B. napus* it can contribute to as much as 4% of the meal (Blair and Reichert, 1984., J. Sci. Food Agric. 35: 29.). Sinapine synthesis occurs in immature seeds that are still light green in appearance, and there appears to be no net degradation as the seeds mature (Vogt et al., 1993., Arch. Biochem. Biophys. 300: 622.). Developing seedlings (i.e. germinating seeds) degrade sinapine by an esterase reaction that yields sinapic acid and choline. It has been postulated, but not proven, that sinapine degradation might provide the choline supply for phospholipid synthesis during seed germination (Strack et al., 1981., Z. Naturforsch. 36c: 215). However, since most non-crucifers do not have sinapine in their seeds, it is unlikely that sinapine is an essential compound for seed development or germination in general.

Mutants defective in the general phenylpropanoid pathway have been isolated in *Arabidopsis thaliana* (Chapple et al., 1992., The Plant Cell 4: 1413–1424). While these mutants provide an excellent framework for physiological, biochemical and genetic studies, they are of no agronomic value due to the negative consequences of the mutation which includes hypersensitivity to UV light due to the manifestation of the mutant phenotype throughout the plant, particularly in the leaves. These mutants, designated SIN1 (SINapoyl malate biosynthesis mutants), block the synthesis of sinapic acid esters, reducing sinapine (a sinapoyl-choline ester) content and further altering the monomer composition of the lignin of the plant. The alteration of the lignin content can lead to plants with lignin of unique composition and hence altered plant fibre.

Chapple et al further discuss the possibility of using mutants such as SIN1 to reduced lignin content or alter lignin content in important crucifer seeds such as canola seed, but there is no direction as to how this may be accomplished. It is further contemplated that the reduction of sinapine in canola seeds is an important objective, however no direction is provided as to how this may be accomplished using the SIN1 mutation. Given the apparent UV sensitivity of the SIN1 mutant, the mutation has little value for use under agricultural conditions. Although methods to reduce sinapine content in seeds have not been described in the art, the SIN1 mutation provides important scientific proof that sinapine is not an essential component of plant growth and development and that seed with reduced sinapine is capable of growth and development. The SIN1 mutation, however, does not provide a method to reduce sinapine content in commercially produced crucifer seeds without the associated deleterious UV sensitivity.

In addition to anti-nutritional phenolic compounds such as sinapine, many products of the phenylpropanoid pathway are involved in the formation of lignin. The biosynthesis of lignin is part of the general phenylpropanoid biosynthetic pathway which produces at least three primary phenolic precursors, coumaric, ferulic and sinapic acids, products of which are polymerized into lignin and other phenolic compounds.

The biochemistry of the formation of lignins from these precursors is complex and there are a number of other enzymes involved such as caffeic acid/5-hydroxyferulic acid-O-methyltransferase (COMT), caffeoyl-CoA-reductase (CCoAOMT), cinnamyl alcohol dehydrogenase (CAD), cinnamoyl-CoA-reductase (CCR), peroxidaese, 4-coumarate:CoA ligase (4CL) and coniferin-specific beta-glucuronidase (CBG). Other enzymes may be involved and the complete biochemistry of lignin formation is not yet fully understood.

Lignin is a complex polymer mainly composed of interconnected units of these monomeric phenolics in various proportions and with different types of linkages in distinct cells types and in diverse species. Lignins are essential components of plant cell walls where tissues require mechanical strength or are involved in water conduction. Additionally lignins are believed to be involved in mechanisms of resistance to pathogens. Common in dicots is guaiacyl-syringyl lignin, comprised of both ferulic acid-derived guaiacyl units and sinapic acid-derived syringyl residues. Accordingly both sinapic and ferulic acid is required for formation of wild-type lignin. The degradability or processability of wood, for example during pulping, is thought to be highly dependent on the monomer composition of the lignin which is primarily based on the availability of specific lignin monomers. It is believed that the presence of the 5-O-methyl groups in the sinapoyl-derived syringyl lignins reduces cross-linking hence making the lignin composed primarily of syringyl units easier to process than lignin composed primarily of guaiacyl units derived from ferulic acid. Accordingly methods to increase the syringyl lignin content may lead to meal that is more digestible due to reduced cross-linking of the lignin.

The digestibility of fodder crops is influenced by the amount of fibre because cross linked lignins are resistant to degradation and act to physically bind the components of the cell wall together.

It is evident from the foregoing that any attempts to improve seed meal by lowering or eliminating sinapine and altering the general phenolic content should be targeted to the developing seeds. In order for the biochemical pathway for sinapine synthesis to be altered specifically in the seeds, a molecular genetic approach is most appropriate, in view of the lack of germplasm that naturally provides for a low sinapine trait.

In one embodiment, the present invention recites a method that alters the level of phenolic compounds in seeds and furthermore alters the level of sinapic acid and related phenolic compounds. The method relies on the introduction of novel enzymatic activities that affect the availability of compounds used as precursors and substrates for enzymes in the phenylpropanoid pathway. Depletion or a change in the abundance of these compounds leads to a biochemical shift in the normal pathway and the production of altered levels of various phenylpropanoid products.

As one example of the method, a novel enzyme activity, choline oxidase (COX) is employed to reduce choline pools in a plant cell, particularly in the plant seed. Choline is used, amongst other things, for the production of sinapine from sinapoyl glucose. Reduction of the choline pool causes the alteration of the pool levels of the sinapine precursors (choline and sinapoyl-glucose) and hence changes the composition of the precursors formed in earlier enzymatic steps of the phenylpropanoid pathway, including sinapic acid. The result is seed with greatly reduced sinapine content and altered phenolic content. It is known that oxidation of choline by choline oxidase produces hydrogen peroxide.

Hydrogen peroxide production in plant cells is considered beneficial and thus there exists an additional benefit to expressing choline oxidase in plants. As an illustration of an additional aspect of the method a second enzyme activity, betaine aldehyde dehydrogenase (BADH), is employed to enhance the conversion of the product of choline oxidase, betaine aldehyde, into glycinebetaine, which functions as a stress protectant. The compound betaine is a valuable compound for various applications in the food industry and as an additive to enhance plant growth.

Accordingly a beneficial effect of altering phenolic content in plant cells and specific reduction of sinapine is shown by the reduction of a single precursor in the phenylpropanoid pathway. It is clear to one skilled in the art that other enzymes can be employed within the scope of the method to alter various other end products in the phenylpropanoid pathway.

Another example within the scope of the present invention is the use of novel enzyme activities to degrade ferulic acid, also formed in the phenylpropanoid pathway. Of the three major lignin monomers, ferulic acid is believed to endow structural rigidity and strength to cell wall architecture by cross-linking pentose chains, arabinoxylans and hemicelluloses, making cell walls more rigid and less susceptible to enzymatic degradation. Thus, as a component of lignin, ferulic acid plays an important role in mechanical strength of plant tissues. Alteration of the level of ferulic acid in a specific manner can lead to many beneficial effects.

Ferulic acid is synthesized within the general phenylpropanoid pathway as described above, and it serves as a precursor for various products of the pathway (reviewed in JPN Rosazza et al., Journal of Industrial Microbiology 15: 457–471, 1995; R Whetten and R Sederoff, Plant Cell 7: 1001–1013, 1995; R A Dixon and N L Paiva, 1995, Plant Cell 7: 1085–1097, 1995).

The present method provides a means to modulate the levels of ferulic acid thereby altering the production of various other compounds in the phenylpropanoid pathway, in particular, sinapine. One aspect of the present invention recites a method that alters the level of ferulic acid in plant cells. The method relies on the introduction of heterologous enzymatic activities that metabolize ferulic acid. Some of the enzymes can also produce compounds of commercial utility. For example, the enzyme ferulic acid decarboxylase is used, producing the compound vinylguaiacol, a compound that may be use as an industrial feedstock and can accumulate in plant cells without a deleterious effect. Depletion or a change in the abundance of ferulic acid leads to a biochemical shift in the normal phenylpropanoid pathway and the production of altered levels of various phenylpropanoid products.

The method according to the invention is not limited to the phenylpropanoid pathway. As an example of the utility of the present invention, modification of the secondary metabolic pathway that produces sugar alcohols is exemplified.

(B) Secondary Metabolic Pathway for Sugar Alcohol Metabolism

The present invention also provides methods and DNA compositions for the alteration of sugar alcohol content in plant cells. As a result ofthe application of the method of the present invention, plant cells modified in compounds derived from sugar alcohols, such as phytic acid, stachyose, raffinose, sucrosyl glycosides, uronides and pentoses, phosphoinositides and glycophosphoceramides are provided. As a result, in some embodiments of the invention, plant seeds with reduced phytic acid are obtained. The invention also provides plant seeds with reduced phytic acid content suitable for feed applications, plant seed with reduced phytic acid content suitable for preparation of modified meal and plant cells with modified inositol metabolism. Other compounds derived from sugar alcohol metabolism are also altered by the present invention, including anti-nutritional sugar alcohol derived compounds such as stachyose and raffinose. Of particular relevance for feed applications is plant seed modified in phytate content.

Phytate is a significanti component of many seeds typically representing 2–4% of the seed mass, but may reach levels of 10% in some species. The presence of high levels of phytate in feed rations has been linked to loss of appetite, reduced litter size and other negative performance factors. These effects are likely due to the Zinc binding ability of phytate. Complexes of phytic acid with other seed components are generally referred to as phytin. High levels of phytin are similarly associated with negative effects.

In addition to the disruptive effects on feed performance, the presence of phytic acid in feed formulations also leads to a number of undesirable environmental consequences. In monogastric animals, the phosphorous associated with phytic acid is generally unavailable, thus phosphorous must be added to the diet as which represents an added cost. The phosphorous associated with phytic acid is excreted by monogastric animals and subsequently the breakdown of the feces by microbes leads to the release into the environment of the phosphorous contained within phytic acid. The high levels of phytic acid in many seed meals results in a significant amount of excreted phosphorous. Continually increasing livestock production has often led to eutrophication of water supplies and other environmental problems related to phosphorous pollution. These problems are expected to increase and may become a major limitation for livestock production in the future. Thus methods to reduce the level of excreted phytic acid will be a significant benefit for ameliorating these environmental problems.

Although the actual costs associated with adding phosphorous to aformulation are not a significant fraction of the feed costs, the environmental consequences of excreted phosphorous generate significant associated costs that could be avoided through the production of low phytate meals.

In ruminant animals the presence of a microbial fauna in the rumen can cause the liberation of the phosphorous contained within phytic acid and hence the phosphorus becomes more available. As a result the amount of added phosphorus in rumen rations is greatly reduced inr comparison with monogastric animals. However, the amount of phytic acid in most plant seeds exceeds that which is actually required, thus even in ruminants phosphorous pollution is a major concern.

To date the predominant methods that have been contemplated for reduction of phytate have been largely directed to degradation of phytate by the action of phytase enzymes contained within the meal. Although this method results in greater phosphorous availability, it does not allow for the production of seed or meal with reduced phytic acid content, only meal where the phosphorous contained within phytic acid is generally more available. Thus the use of the phytase enzyme finds utility only in making the phosphorous in phytic acid more available.

Phytase activity is commonly encountered in microorganisms such molds (Aspergillis), bacteria (Bacillus, Pseudomonas) and yeast (Saccharomyces). The removal of phytate by treating plant materials with enzymes mixtures containing microbial phytase is described for example in U.S. Pat. No. 5,554,399. Most microbes synthesize a number of phytase activities, which may include the phytase activity itself in addition to various phosphatases that further degrade phytic acid. The complete liberation of the available phosphorous from phytic acid may be dependent on a number of distinct enzyme activities.

The alternative approach of transforming plants to produce microbial phytase has also been described. U.S. Pat. No. 5,593,963 describes the expression of phytase in transgenic plants under the control of regulatory sequences that include those capable of directing expression either constitutively or in a stage or tissue specific manner. Plant cells or more specifically plant seed cells can be produced which contain a phytase activity that can release a portion of the phosphorous contained within phytic acid.

However, the simple liberation of phosphorous from phytic acid does not fully address the problem of reducing phosphorous waste and the potential anti-nutritional effects of phytic acid. More importantly the presence of complexed phytic acid or phytate is not reduced. The published art provides means to liberate phosphorous from phytic acid, but does not provide a means to control the levels of phytic acid produced.

Any means by which phytic acid levels could be conveniently manipulated would find great utility in feed applications. For instance, plant seed with reduced phytic acid levels would provide a meal with greater mineral availability. Plant seed with reduced phytic acid would also provide a seed meal with reduced phytin and may therefore be more nutritious and digestible due to the reduction of phytic acid complexes.

In addition to nutritionally improved meals, reduced phytic acid meals would result in lower phosphorous release into the environment and less pollution. Although means to liberate phosphorous from phytic acid can reduce the level of added and excreted phosphorous, the actual levels of phytic acid and hence potentially available phosphorous are in excess of the requirements forphosphorous nutrition in most animals.

Accordingly methods to manipulate phytic acid levels will find utility in all feed applications and furthermore provide meal and feed compositions that are novel and valuable.

In view of these concerns, it is evident that a means by which the production of phytate during seed development could be regulated would be useful and provide a solution to the problems associated with phosphorous pollution and anti-nutritional effects of phytic acid. Additionally a genetic mechanism that would find utility across a wide range of plant species would be particularly valuable. The present invention provides such solutions.

Appreciation of the biochemical mechanism responsible for the formation of phytic acid is required to understand the scope of the present invention. Although the biosynthesis of phytic acid is not completely understood, there are a number of key steps that are known. Phytic acid is the hexaphosphate derivative of myo-inositol; the biochemical pathway that synthesizes phytic acid utilizes myo-inositol, a sugar alcohol, exclusively as the initial substrate. This compound (myo-inositol, also commonly referred to as inositol) is also central to production of other myo-inositol derivatives and epimers. Some of these derivatives, such as sucrosyl glycosides, are also anti-nutritional compounds and hence reduction of these compounds is also desirable.

Myo-inositol is a sugar alcohol that is ubiquitous in plant cells. However, the simple protection of any one of the myo-inositol hydroxyl groups renders it unsuitable for the biosynthesis of phytic acid and other pathways. Protection of myo-inositol can be accomplished in vivo by methylation at specific sites by various methyl transferases. For example, myo-inositol is converted to ononitol through monomethylation at position 6. Methylation at position 5 produces sequoyitol, which is epimerized to pinitol. Pinitol can not be used for phytic acid biosynthesis. Methylated derivatives of myo-inositol are known to confer beneficial properties to the plant such as stress tolerance and they are involved in solute transport and stabilizing membrane proteins. Thus modification of inositol by use of heterologous enzyme activities not normally associated with sugar alcohol metabolism is contemplated within the scope of the present invention.

The biochemistry of phytate formation is not well understood, however, at least two potential pathways for formation are known and there appears to be a number of different enzyme activities involved in phytic acid biosynthesis. Phytate is found in most plant tissues, however it is particularly prevalent in seed and pollen which supports a predicted role in phosphorous storage. Thus it has proven difficult to devise a means to modify phytate biosynthesis by conventional means, particularly since the biochemistry of its formation is not well understood.

In order to minimize the production of phytic acid, the present invention describes methods and DNA compositions that encode an enzyme(s) that modifies myo-inositol, preventing the utilization of myo-inositol in phytic acid biosynthesis. The present invention contemplates the use of a heterologous methyl transferase gene to specifically methylate myo-inositol in seed, particularly the tissues in the seed responsible for phytic acid biosynthesis. (By heterologous it is meant an enzyme not normally associated with phytate biosynthesis in said plant cell.) The invention utilizes a heterologous enzyme activity obtained from a halophytic plant, an enzyme activity not found in conventional crop plants such as corn, soybean, cotton, alfalfa, wheat, barley, rye, sorghum, sunflower, Brassica oilseeds, and other conventionally farmed crops.

The production of methyl inositol from myo-inositol also provides the added benefit of producing an innocuous compound with no detrimental effect to the plant cell. Thus, by reduction of the pool of available myo-inositol, phytic acid production is reduced.

Phytate is one of the major anti-nutritional factors in seed meal. The anti-nutritional effects of phytic acid include mineral binding, formation of complexes with protein and other negative effects, particularly those related to the excretion of excess phosphorous in the form of phytic acid which is metabolized in the environment creating phosphorous pollution. Accordingly methods to reduce phytic acid in plant cells have utility in feed applications. In aquaculture, high phytic acid levels are also a major problem for the use of plant derived protein as a substitute fortherring meal. Thus methods to reduce phytic acid content of plant cells, in particular cells of plant tissue used for animal feed, are valuable and have great utility. Methods to reduce phytic acid content of plant seed across a wide range of plant species used for animal feed is particularly valuable for the feed industry.

The plant gene encoding myo-inositol-O-methyl transferase (IMT) has been isolated from *Mesembryanthemum crystallinum* (ice plant) and this enzyme has been shown to convert myo-inositol to pinitol in heterologous transgenic plants (U.S. Pat. No. 5,563,324). This plant gene has been placed under the control of a constitutive promoter with the goal of increasing stress tolerance in plants by overproduction of the methylated derivative of myo-inositol, ononitol, which may be subsequently epimerized to pinitol. In the present invention, the plant gene is placed under the control of a seed selective promoter to alter inositol metabolism in the seed.

The production of pinitol described in U.S. Pat. No. 5,563,324 was shown to confer tolerance to salt when constitutively expressed in throughout tranagenic tobacco plants. Similarly, the expression of a bacterial mannitol 1-P dehydrogenase, when expressed constitutively in a plant cell catalyzes the production of mannitol, a sugar alcohol or polyol and causes the plant cell to become tolerant to salt stress. Hence U.S. Pat. No. 5,563,324 describes the production of sugar alcohols by the use of an enzyme capable of producing a sugar alcohol from sugars native to plant cells as a means to confer salt tolerance on plant cells.

However, U.S. Pat. No. 5,563,324 does not provide any direction for the use of a gene capable of modifying myo-inositol to prevent the use of myo-inositol as a precursor to other compounds which comprise native derivatives. U.S. Pat. No. 5,563,324 provides clear evidence, however, that the modification of myo-inositol does not lead to any negative effects on the plant and hence manipulations of myo-inositol levels would not be expected to lead to detrimental effects.

Accordingly the possibility of the modification of myo-inositol by a methyl transferase gene is not anticipated to be detrimental to plant cells and the methylated product of this enzymatic reaction is known to be innocuous to plant cells.

However, myo-inositol is fundamental to many different aspects of plant growth and development. In addition to its role as the precursor for phytic acid biosynthesis, myo-inositol is also used for uronide and pentose biosynthesis, it is also present in phosphoinositides of plant cell membranes, as well as other complex plant lipids including glycophosphoceramides. Furthermore, it is also a precursor of other naturally occurring inositol isomers, and many of these as well as myo-inositol are distributed as methyl ethers in a species specific pattern throughout the plant kingdom.

The role of myo-inositol in general plant metabolism is large and modification of the myo-inositol pool could have unforeseen consequences, especially under agronomic growth conditions. Although U.S. Pat. No. 5,563,324 describes the constitutive expression of the methyl transferase gene, it does not provide any evidence that the resultant plants have utility. It is stated in U.S. Pat. No. 5,563,324 that: "Even if newly inserted genes do not make a plant perform better in agricultural conditions, transgenic plants carrying such genes are useful for research purposes for investigating how changes in plant internal processes (e.g. osmotic regulation) affect the field performance of the plants." (Column 2, lines 60–65). Hence U.S. Pat. No. 5,563,324 does not anticipate the manipulation of myo inositol levels for the reduction of phytic acid or fully expect that plants with useful agronomic characteristics, and hence utility, will result from the teachings contained therein. Accordingly U.S. Pat. No. 5,563,324 describes the expression of a myo-inositol-modifying gene in whole plants for the purposes of stress tolerance or further scientific study.

Accordingly it is fully believed that a novel approach to the reduction of phytic acid is taught by the present invention. The use of the methyl-transferase gene is specific to the reduction of phytic acid. The present invention does not rely on methods already in the art, such as expression of phytase enzymes that do not address the problem of excess phytic acid in seed and or seed meals. In the course of the work carried out herein, it was found that the levels of phytic acid can be controlled by altering the levels of myo-inositol available for phytic acid biosynthesis. It was discovered that expression of a methyl transferase gene in seed tissue leads to the reduction of phytic acid in the seed with out any demonstrable changes in other characteristics of the plant. It is evident that limitation of the expression of the methyl transferase gene to the tissues of the seed responsible for the biosynthesis of phytate significantly reduced phytic acid in mature seeds without any additional effects on the plant, even grown under the environmental extremes of field conditions. The use of a tissue-selective promoter offers many advantages over the art including the restriction of the enzyme activity to seed tissue while leaving myo-inositol metabolism intact in other tissues.

The objective of the present invention is to divert the utilization of myo-inositol as a starting material for phytic acid biosynthesis, by diversion into a metabolic pool where it is converted to compounds that are innocuous to the plant. The method relies on the introduction of novel enzymatic activities comprising, in one embodiment a methyl-transferase gene that depletes or alters the pool of myo-inositol used to produce phytic acid. Depletion or alteration of the levels of this precursor leads to abiochemical shift in the normal pathway for phytic acid biosynthesis and causes the reduction in the level of phytic acid produced.

The biochemical basis for this invention is based on the concept of the regulation of enzyme activity by the availability of substrates. In general, enzymatic rates are controlled by the availability of substrate. An enzyme will produce a product at a rate that is generally proportional to the amount of substrate available. The reduction of substrate concentrations leads to lower levels of final end products.

Accordingly the present invention takes advantage of this approach by using a novel enzyme activity, a methyl transferase that depletes the availability of the inositol substrate used for the formation of phytic acid. Any number of enzymes capable of acting upon the pool of myo-inositol in the plant seed could be used within the scope of the present invention. The method relies on an introduced enzymatic activity that in any number of different fashions, alters the pool of myo-inositol used for phytic acid biosynthesis.

In contrast to U.S. Pat. No. 5,563,324, the present invention seeks to modify phytate production in a seed-selective manner by expression of a gene capable of modifying myo-inositol rendering it unavailable for phytic acid production. Surprisingly, even constitutive expression of a myo-inositol modifying gene leads to reduced phytate levels in the seed. However, in a most preferred embodiment of the present invention a seed-selective promoter is utilized to ensure the agronomic performance of the plant is not compromised and the resultant plant is normal in every fashion with the exception of reduced phytate levels in the seed. Therefore, in contrast to U.S. Pat. No. 5,563,324, the present invention does not anticipate the production of stress tolerant plants nor does it read on plants useful for research purposes.

The described method offers many advantages over the art related to reduction of phytic acid by the expression of phytase enzymes. These include plants altered phytic acid levels in specific tissues, plant with seed with reduced phytic acid levels and seed meal with reduced phytic acid. The benefits of such plants, seeds and meals include better feed utilization and meal performance, meal and feed preparations with reduced levels of phosphorous and hence better environmental attributes and ability to use said meals for applications in the feed industry previously restricted by the amount of the anti-nutritional phytic acid in the meal or feed.

The described method finds utility in many plant species. These plant species include monocot and dicot plants, as well as grains and oilseed crops. The method finds particular utility in oilseeds and cruciferous plants.

The results of this genetic modification are plant cells with modified sugar alcohol metabolism, particularly inositol metabolism, and plant cells with reduced phytic acid content, in particular plant seed with reduced phytate content. Thus the method of the present invention provides a valuable means to alter secondary metabolism related to sugar alcohols.

Although the embodiment of this invention involving alteration of sugar alcohol metabolism, for example plant cells with reduced phytic acid content, has been demonstrated in canola plant cells, corn plants also have a high phytic acid concentration and a reduction of phytic acid content in corn cells is similarly achievable.

The present invention provides methods, genetic constructs and vectors useful for modifying the phytate content of plant cells and seeds, in particular for the reduction of phytate levels in plant cells. The invention further provides methods and DNA compositions useful for reduction of phytate in plant seeds. The invention further relates to modified seed meal and animal feed containing modified seed meal, particularly seed meal with reduced phytate content.

The reduction of phytic acid is accomplished using newly described methods and DNA compositions. The method comprises the development of a "metabolic shunt" or a new biochemical pathway, capable of diverting, a precursor in the phytic acid biosynthetic pathway to a new and novel introduced "dead end pathway" which reduces the production of phytic acid. As a result of one specific embodiment of this method, the product(s) of the "dead end pathway" are compounds that are known to be innocuous to said plant cell. Accordingly, it is fully believed that the shunting of the precursor myo-inositol compounds into these compounds will not compromise plant performance in any way.

In accordance with another aspect of the invention, vectors and recombinant DNA constructs are provided for the production of plant seed with altered phytic acid content, particularly plant seed with reduced phytic acid content. In addition another aspect of the invention provides plant seeds useful for the production of seed meal with reduced phytate content. Said meal has reduced phytate levels and hence is useful for animal feed, especially for those applications where phytic acid is associated with environmental pollution or has been identified as an anti-nutritional factor. The invention also provides modified meal derived from genetically altered seed that can be used in various animal diets including those for poultry, swine, cattle and fish.

The method comprises the addition of a novel enzymatic activity that can alter the content of myo-inositol in seed and can be directly applied in all species and varieties of plants. The same gene can be used across any plant species, since the alteration of myo-inositol will occur in the same fashion in any plant species. The method does not rely on the use of gene suppression technologies that are DNA sequence dependent and hence would require specific genes tailor-made for each specific gene or crop species. Thus the utility of the present invention for all crops is evident. Numerous suitable enzymes from microbial, plant or animal sources can be employed within the scope of the method. The same genetic constructs can be used in a variety of different plant species.

Thus in accordance with a broad aspect of the present invention, there is provided a method of reducing phytate content in plant seeds comprirsing the construction of a plant transformation vector containing, in addition to a selectable marker that permits the identification of plant cells transformed with said vector, an enzyme capable of metabolizing myo-inositol, rendering myo-inositol unsuitable for the production of phytic acid.

In context of the present invention, metabolization of inositol includes hydroxlation, isomerization, methylation, cleavage, or any other biochemical modification that renders myo-inositol unable to be acted upon by the corresponding enzymatic activity that normally acts upon myo-inositol to produce phytic acid. Hence metabolization includes any modification that effectively reduces the availability of myo-inositol from the pool of available substrates for phytic acid biosynthesis.

As an example of the present invention, a gene encoding a myo-inositol methyl-transferase is used to illustrate one aspect of the invention. Said enzyme, under the control of a promoter selective for expression in plant seed cells, is capable of depleting the pool of myo-inositol available for production of phytate in said plant seed. In accordance with another aspect of the present invention said methyl transferase is capable of converting myo-inositol into an innocuous substance.

Plant cells produced by the method according to the present invention have unaltered primary metabolism and have phenotypes that are indistinguishable from unmodified plants with the exception of the alteration of the product or products with a specific secondary metabolic pathway.

In order to ensure that primary metabolism is unaffected, the present invention describes a method to target, in a tissue specific manner, the formation of a secondary metabolite by altering the availability of a substrate that is specific to the secondary metabolic pathway, and essential to the formation of the final product of that pathway, particularly those substrates within from one to five biochemical steps of final product formation. In this fashion, a reduction of specific products of the secondary metabolic pathway is achieved.

In the context of the present invention, compounds used as precursors to products of the phenylpropanoid secondary metabolic pathway include but are not limited to: cinnamic acid, p-coumaric acid, caffeic acid, ferulic acid, 5-hydroxyferulic acid, siinapic acid, choline, various sinapoyl compounds which include but are not limited to sinapoyl-glucose and sinapoyl-malate and sinapoyl choline. Within the context of the present invention, products of the phenylpropanoid pathway include but are not limited to: flavonoids, lignins, various monomeric and polymerized phenolic compounds and sinapine. By selection of a specific enzyme, any number of alterations to the levels of products within the phenylpropanoid pathway can be achieved. The enzymes used to modify or target the compounds used as precursors can be of microbial, animal or plant origin. The enzymes can be naturally occurring or be derived by mutation of a known enzyme to alter its substrate specificity hence producing a novel enzyme activity.

The enzymes used within the scope of thepresent invention can be those capable of modifying the compounds used as precursors to products found within the phenylpropanoid pathway by isomerization, conjugation, phosphorylation, hydroxylation, oxidation, dehydrogenation, methylation or any other similar biochemical activity (including binding or sequestration) or may comprise enzymes capable of destroying the compounds used as precursors within the phenylpropanoid pathway such as hydrolases, decarboxylases, oxidases, esterases or any other enzyme capable of degrading L-phenylalanine, cinnamic acid, p-coumaric acid, caffeic acid, ferulic acid, 5-hydroxyferulic acid, sinapic acid, sinapoyl-glucose, sinapoyl-malate or choline (used to produce sinapine from sinapoyl-glucose). In one aspect of the method, enzymes are used which produce stress protectant substances from compounds used as precursors of products formed normally within the phenylpropanoid pathway. Similarly, the use of an enzymatic activity for the specific reduction of an additional substrate, not produced as part of the phenylpropanoid pathway but required for the formation of a product of the phenylpropanoid pathway, can be used to reduce the level of said product. Accordingly both compounds used as precursors in the phenylpropanoid pathway and any other compound required by the phenylpropanoid pathway to produce products can be targeted within the scope of the present method.

In the context of the present invention, compounds used as precursors to products of the sugar alcohol secondary metabolic pathway include but are not limited to: myo-inositol, galactinol and UDP-derivatives of sugars. Products of sugar alcohol metabolism include, but are not limited to: phytic acid, stachyose, raffinose, sucrosyl glycosides, uronides and pentoses, phosphoinositides and glycophosphoceramides. In context of the present invention, the enzymatic activity used to alter the compounds of sugar alcohol metabolism include those capable of hydroxlation, isomerization, methylation, cleavage, or any other biochemical modification (such as binding or sequestration) that renders a sugar alcohol unable to be acted upon by the corresponding enzymatic activity that normally acts upon said sugar alcohol. In the illustration of the present invention within the sugar alcohol secondary metabolic pathway, methylation of inositol which is the precursor to phytic acid is shown to reduce the availability of inositol for phytic acid biosynthesis.

Accordingly, it is clear to those skilled in the art that the precursors to a final product within a secondary metabolic pathway are those biochemicals which are used directly for the formation of a secondary metabolite, or those biochemicals which are used in a biochemical reaction leading to the formation of a specific secondary metabolite, said biochemicals not being a primary metabolite.

The enzymes used to act upon or target the compounds which function as precursors of products within a secondary metabolic pathway preferably produce from said compounds substances that are harmless to the plant cell and hence can accumulate to high levels without altering the properties of the plant cell. The enzymes can also produce substances that provide a beneficial effect to the plant cell such as the production of stress protectants from said compounds used as precursors of products of the secondary metabolic pathway. The enzymes used can also produce substances of utility such as industrial chemicals, pharmaceutical or nutraceutical substances. One or more enzymes may be employed within the scope of the present invention, and more than one distinct activity may be employed to reduce the level of specific compounds used as a precursor to a product within a secondary metabolic pathway.

The enzymes used in the context of the present invention may be derived from a number of sources or by a variety of methods. For example, the skilled artisan can identify a compound used as a precursor within a secondary metabolic pathway to be targeted within the scope of the present method. The chemical structure of these compounds are well-known, or can be identified, hence the enzyme literature can be analysed to identify an enzyme with known activity on chemically similar substrates. Accordingly a suitable enzyme can be identified, and the gene isolated and used within the context of the present invention. Additionally, combinatorial chemistry or similar schemes that search artificially produced proteins for desirable activity may also be used as the basis to obtain a synthetic gene. The enzymes used within the scope of the present invention can be modified using methods commonly known in the art.

As one example of an enzyme modification, the gene encoding an enzyme capable of acting upon chemically related compounds used as precursors, in a secondary metabolic pathway can be modified and/or selected for increased activity by using such techniques as site-specific modification, mutation and selection of altered specificities in heterologous systems such as bacterial or fungal cells. This may include expression of the gene encoding said altered enzyme in bacterial cells unable to metabolize said compounds, selecting bacteria that express the enzyme and are able to grow on said compounds as the only nutrient or carbon source and recovering an enzymatic activity capable of acting upon a specific compound used as a precursor in a secondary metabolic pathway. In this fashion, it is possible to produce an enzyme with specificity for a specific compound used as a precursor within a specific secondary metabolic pathway. Alternatively, bacteria can be selected for growth on various compounds used as precursors within a secondary metabolic pathway. The skilled artisan can readily appreciate the selection of mutated bacteria or other cells on specific compounds used as precursors within a secondary metabolic pathway can provide a means to identify specific enzyme activities capable of converting said compounds into innocuous substances. This approach may include direct selection of specific enzymatic activities or stepwise modification and selection of desired enzymatic activities.

Similarly, the use of known enzymatic activities currently used commercially, such as enzyme preparations using Trichoderma fungal extracts capable of degrading lignin in pulping operations, may provide a source of suitable enzyme activity, for example to isolate enzymes involved in degradation of phenolic compounds. It is apparent to those skilled in the art that genes encoding enzymes used in the pulp industries for processing of lignin can be employed within the scope of the method, either directly or upon modification, to specifically act on one of the compounds used as a precursor in the phenylpropanoid pathway. Accordingly, it is contemplated that a number of different enzymatic activities can be employed within the scope of the present method. The method is not limited therefore by the source or specificity of the enzyme used.

For example, in one aspect of the method, an enzyme which is expressed in a plant cell acts upon a compound used as a precursor or substrate to a product within the phenylpropanoid pathway to produce a substance that is no longer acted upon by the enzyme that would normally utilize said compound as a precursor within the phenylpropanoid pathway. Accordingly, the levels of the specific product of the phenylpropanoid pathway are reduced through reduction of the precursors required for the formation of said product. The resultant plant cell can be used directly or the cell can be induced to regenerate a whole plant with altered levels of products of the phenylpropanoid pathway which has utility in any number of industrial processes not limited to feed applications, pulping applications or production of plants with novel phenolic compound compositions, including overproduction of certain products within the phenylpropanoid pathway. Trees with altered levels of phenylpropanoid products will have utility in the pulp and paper industry. Plants with altered levels of phenylpropanoid products will have utility in the feed industry.

The method also relies on the recovery and use of the plant cells or tissue with the altered properties, particularly plant tissue used for feed applications or other industrial processes. It is possible that the alterations to the phenylpropanoid pathway contemplated within the scope of the present invention may also lead to positive changes in agronomic performance of plants derived from said methods, particularly those aspects of the invention where the production of a stress protectant results from the added enzymatic activity. Other beneficial effects may be anticipated which may include enhanced disease and UV resistance, mechanical strength and so forth.

In a further embodiment of the invention, the method includes the step of growing said plant cell and recovering a plant wherein the products of the phenylpropanoid pathway have been altered.

In yet a further embodiment, the invention includes using said plant for an industrial process such as production of useful compounds, animal feed preparation or pulping.

The genes encoding the enzymes capable of acting on compounds used as precursors of products of the phenylpropanoid pathway can be natural, synthetic or a combination thereof. The skilled practitioner will readily appreciate that the coding sequence of the gene may be modified to allow for high levels of expression in plant cells. This can be accomplished by altering the sequences of the codons to more correctly resemble the codon usage normally found in the plant cell where the gene will be expressed. Furthermore, it is obvious that specific restriction sites may be engineered to allow for convenient manipulation of the coding sequence. It is also contemplated that addition of various sequences such as translational enhancers, introns, etc. may be used to ensure adequate expression of the coding sequence. Enzymes may also be modified by alteration of substrate binding sites or other modification to the primary amino acid sequence that enhances the enzymatic activity. All of these manipulations are common in the art and will be readily appreciated by the skilled worker.

In another aspect of the present invention, the enzyme is under control of a tissue selective promoter, more particularly a seed-selective promoter. A seed-selective promoter is a promoter which functions exclusively or preferentially to cause expression of sequences under its control to be limited to tissue within a plant seed. Accordingly levels of the specific product of the phenylpropanoid pathway are altered in a tissue selective manner, leaving the other tissues of the plant with normal levels of phenylpropanoid pathway products. The tissue wherein the enzyme is selectively expressed is used in preparation of a feed or any other industrial process.

It is obvious to the skilled practitioner that any number of tissue-selective promoters may be employed within the scope of the present invention. In particular, a seed-selective promoter is used to alter the products of the phenylpropanoid pathway in crops where seed or seed meal is used for feed. In other crops, various tissue-selective promoters may be used dependent upon the portion of the plant where alteration of phenolic content is desired. For instance a root or tuber-selective promoter may be employed to alter phenolic or lignin content of root or tuber crops such as potato, turnip, cassava, etc. In those instances where leaves or stems are used as feed, a leaf or stem-selective promoter may be employed to limit the expression of enzymes capable of acting on compounds used as precursors within the phenylpropanoid pathway. Other tissue-selective promoters may be used in plants such as trees that are harvested for pulping. Hence a promoter that restricts the activity of the enzyme to the wood of the tree finds utility within the scope of the present method.

In one specific aspect of the present invention, the expression of a coding sequence of a choline-metabolizing enzyme in plant cells is contemplated. Expression of said choline metabolizing enzyme depletes the pool of available choline used to form sinapine from sinapoyl-glucose. Some plant species, notably those of the Cruciferae family produce an anti-nutritional compound called sinapine. Sinapine is believed to be synthesized by exchanging the glucose moiety of sinapoyl glucose (sin-glu) with choline. Reduction of the anti-nutritional compound sinapine enhances the value of the seed and resultant meal derived therefrom. The use of a choline modifying enzyme such as choline oxidase has utility in the present invention.

It is known that choline is oxidized to betaine in food plants such as wheat, spinach, sugarbeet and barley (Rhodes and Hanson, 1993, Annual Review of Plant Physiology and Plant Molecular Biology, 44: 357–384). This oxidative pathway is catalysed by two enzymes (known as "choline oxidation system" in generic terms) and the products of this pathway are shown below:

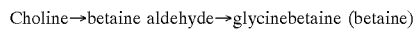
Choline→betaine aldehyde→glycinebetaine (betaine)

The first step is catalysed by a choline dehydrogenase (CDH) or choline oxidase (COX) in bacteria and animals (Rozwadowski, Khachatourians and Selvaraj, 1991, Journal of Bacteriology, 173: 472–478) and by a choline monooxygenase (CMO) in plants (Rhodes and Hanson, 1993). The second step is catalysed by a betaine aldehyde dehydrogenase (BADH) (Rhodes and Hanson, 1993). Accordingly, the use of a choline metabolizing enzyme can deplete the pool of available choline in a general or specific manner by the use of constitutive, inducible or tissue-specific promoters. Reduction of choline availability reduces the production of sinapine. Additionally the reduction in sinapine can cause changes in the levels of other products of the phenylpropanoid pathway leading to a plant tissue with altered phenolic content.

In another specific embodiment of the present invention a microbial choline oxidase (COX) gene (Rozwadowski, Khachatourians and Selvaraj, 1991, Journal of Bacteriology, 173: 472–478) is placed under the control of a seed selective promoter. The expression of choline oxidase in seeds diverts choline, one of the precursors of sinapine biosynthesis in canola seeds, to an innocuous substance, betaine, through the formation of betaine aldehyde which is slowly converted to betaine by the activity of the COX enzyme. The seed comprising the recombinant DNA have reduced sinapine levels and altered levels of other products of the phenylpropanoid pathway. Meal derived from said seed is useful for feed applications.

In another specific embodiment of the present invention the COX gene is used under the control of a seed selective promoter and a second enzyme, BADH, is used to enhance the formation of betaine from betaine aldehyde. In this embodiment, BADH (Boyd, L. A., L. Adam, L. E. Pelcher, A. McHughen, R. Hirji, and G. Selvaraj, 1990, Gene 103: 45–52.) is expressed under the control of a seed-selective promoter. Betaine is a compound found in the edible parts of many food and feed plants, and it is also used as a food and feed additive in some instances. Betaine also provides a stress protectant function.

In another specific embodiment of the present invention the COX gene is used in a cruciferous plant cell (Brassica sp.) under the control of a seed selective promoter, and a second enzyme BADH, also expressed under the control of a seed-selective promoter, is used to ensure the formation of betaine from betaine aldehyde.

The alteration of choline in cruciferous seed provides for a reduction in sinapine content and further an alteration in various products of the phenylpropanoid pathway. It is fully believed that the alteration of choline levels in the seed leads to higher levels of sinapoyl glucose or other sinapoyl compounds such as sinapoyl malate which in turn alters the levels of sinapic acid, a precursor to lignin. Hence the biochemical regulatory mechanism commonly referred to as end-product inhibition is invoked, leading to the alteration of the level of various products within the phenylpropanoid pathway. Accordingly, prevention of the formation of sinapine results in changes to the levels of a number of products formed by steps in the phenylpropanoid pathway prior to the terminal step of sinapine formation.

The secondary metabolic phenylpropanoid pathway can also be targeted through the enzyme, expressed in plant cells, which acts upon ferulic acid. Ferulic acid is another precursor in the phenylpropanoid pathway. Accordingly, the levels of ferulic acid are reduced. Reduction of the availability of ferulic acid leads to alterations in the levels of phenolic compounds, including the reduction of sinapine in cruciferous plants.

The genes encoding the enzymes capable of acting on ferulic acid can be natural, synthetic or a combination thereof. The skilled practitioner will readily appreciate that the coding sequence of the gene may be modified to allow for high levels of expression in plant cells.

In accordance with another aspect of the invention, the gene encoding the enzyme capable of acting on ferulic acid is placed under the control of a tissue selective promoter. Accordingly levels of ferulic acid are altered in a tissue selective manner, leaving the other tissues of the plant with normal levels of ferulic acid. The tissue wherein the enzyme is selectively expressed is used in preparation of a feed, food preparation or any other industrial process.

The enzymes contemplated for use in these embodiments of the present invention include those capable of modifying ferulic acid and in particular those enzymes known to produce valuable compounds from ferulic acid. It is clear, to a man skilled in the art, that other enzymes can be employed within the scope of the method to metabolize ferulic acid. Known sources of ferulic acid metabolizing activity are found in the following microorganisms: Aerobacter sp, *Bacillus megaterium, B. subtilis, Corynebacterium glutamicum,* Enterobacter sp., Psuedomonas sp., Streptomyces sp., Aspergillis sp., Candida sp., Fusarium sp., Hansenula sp., Penicillum sp., Rhodotorula sp., Saccharomyces sp. This listing is not exhaustive, but serves to illustrate the many sources of ferulate metabolizing enzymes that are found in the art. Thus the method is not limited by the source of the enzyme used to metabolize ferulic acid. Within the scope of the present invention, alteration of the microbial encoded gene to ensure optimal expression in plant cells is contemplated. Said methods are well known in the art.

As an example of these enzymes, a ferulic acid decarboxylase from *B. pumulis* is used. The gene for this enzyme has been isolated and sequenced (Zago et al., Applied and Environmental Microbiology 61:4484–4486, 1995). The gene sequence can be modified to more closely resemble a plant gene while maintaining the predicted amino acid sequence. The enzyme is capable of producing vinylguaiacol from ferulic acid by decarboxylation. Accordingly, in one example of the method a valuable compound (vinylguaiacoli VG) is produced by the activity of an introduced gene capable of acting on ferulic acid. The enzyme does not require additional co-factors and has an apparent molecular weight of approximately 22 Kda.

In another specific embodiment of the present invention the ferulate decarboxylase enzyme is placed under the control of a tissue selective promoter, leading to a plant comprising tissues specifically altered in ferulic acid metabolism.

The alteration of ferulic acid provides for a reduction in ferulic acid content and further an alteration in various products of the phenylpropanoid pathway.

The present invention also contemplates the production of plant tissue, in particular plant seed, that has utility for feed or food applications. Both the direct feeding of seed and the use of modified meal from processed seed is within the scope of the present invention. The reduction of phenolic content in plant seeds is desirable in feed applications and the genetically modified seed with altered phenolic content, in particular lower anti-nutritional phenolic content has great utility in the feed industry.

In addition to direct feeding of whole or partially disrupted seed, there are many methods used to produce seed meal. Of particular importance in cruciferous seeds is the production of meal during extraction of oil from cruciferous oilseeds. In general, oil is extracted from oilseeds using either a solvent or non-solvent process. The cake or expelled solids produced by this process is used for meal formulations and usually contains the majority of the phenolic content of the cruciferous seed. A method to produce meal with lower phenolic content provides a novel composition not currently found in meal derived from cruciferous seeds.

The present invention contemplates utilizing the genetically modified seed produced according to the method to obtain a meal product with altered phenolic content.

The described method offers many advantages for the alteration ofa plant phenotype. Additionally the method permits the production of various compounds with known industrial utility. The described method finds utility in any plant species or plant tissue.

The described method offers many advantages over the published art related to manipulation of the phenylpropanoid pathway. The method does not rely on mutations such as the SIN1 mutation that is manifested throughout the plant and is associated with UV sensitivity. The method does not utilize genetic mechanisms designed to block gene expression such as antisense RNA or co-suppression that require the cloning of plant genes from the phenylpropanoid pathway. The method does not specifically modify any gene native to the plant. Accordingly the various functions of the pathway such as production of flavonoids, production of UV protectants, involvement in disease response and other biochemical functions of the pathway are not detrimentally altered. By the use of tissue selective promoters, phenolic content can be altered in any tissue while the other tissues of the plant remain unchanged.

The described method finds utility in many plant species but finds particular utility in cruciferous plants. As a result of the method, an additional benefit is provided by the production of a stress protectant or valuable industrial compound as a result of the introduced enzyme activity. It is obvious that any number of steps within the phenylpropanoid pathway can be targeted by the method and other biochemical pathways may also be modified with a similar approach.

The present invention also finds utility in modifying other secondary metabolic pathways. For example, in one embodiment of the present invention, there are provided methods and DNA constructs for production of plants with altered sugar alcohol metabolism, in particular alteration of phytate content in seed cells. Phytate is derived from the sugar alcohol myo-inositol that also serves as a precursor or intermediate for the formation of other compounds including: stachyose, raffinose, sucrosyl glycosides, uronides and pentoses, phosphoinositides and glycophosphoceramides. The invention further provides methods and DNA compositions to reduce phytate content in cruciferous seeds. The invention also provides plant seeds with reduced phytic acid content suitable for feed applications, plant seed with reduced phytic acid content suitable for preparation of modified meal and plant cells with modified inositol metabolism.

The present invention provides methods and DNA constructs for production of plants with altered phytate content in seed cells. The invention further provides methods and DNA compositions to reduce phytate content in monocots, dicots, oilseeds and cruciferous seeds. The invention also provides plant seeds with reduced phytic acid content suitable for feed applications, plant seed with reduced phytic acid content suitable for preparation of modified meal and plant cells with modified inositol metabolism.

The present invention contemplates the expression of genes encoding enzymes that act on a sugar alcohol precursor to phytic acid biosynthesis, myo-inositol, causing the metabolic diversion of this precursor into "dead-end" or poorly metabolized compounds that can harmlessly accumulate in the plant cell. In this fashion, a reduction of phytic acid biosynthesis is achieved. Other sugar alcohols can be targeted by the methods described in the present invention. The enzyme used to target myo-inositol can be of microbial, animal or plant origin. The enzyme can be naturally occurring or be derived by mutation of a known enzyme to alter its substrate specificity hence producing a novel enzyme activity.

The enzyme used to act upon myo-inositol preferably produces compounds that are harmless to the plant cell and hence can accumulate to high levels without deleterious effects on the plant cell. One or more enzymes may be employed within the scope of the present invention, and more than one distinct activity may be employed to reduce the level of myo-inositol.

The enzymes used within the scope of the present invention are those capable of modifying myo-inositol by isomerization, conjugation, phosphorylation, hydroxylation, methylation or any other similar biochemical activity or may comprise enzymes capable of eliminating myo-inositol or other sugar alcohols.

The enzymes used in the context of the present invention may be derived from a number of sources or by a variety of methods. For example, the skilled artisan can identify an enzyme with known activity on chemically similar substrates. Accordingly the enzyme can be identified, the gene isolated and used within the context of the present invention. The enzymes used within the scope of the present invention can be modified using methods commonly known in the art.

The method further relies on the use of transformation to introduce the gene encoding the enzyme into plant cells. Transformation of the plant cell can be accomplished by a variety of means. Methods that have general utility include Agrobacterium based systems, using either binary and cointegrate plasmids of both *A. tumifaciens* and *A. rhyzogenes*. (e.g., U.S. Pat. Nos. 4,940,838, 5,464,763), the biolistic approach (e.g., U.S. Pat. Nos. 4,945,050, 5,015,580, 5,149,655), microinjection, (e.g., U.S. Pat. No. 4,743,548), direct DNA uptake by protoplasts, (e.g., U.S. Pat. Nos. 5,231,619, 5,453,367) or needle-like whiskers (e.g., U.S. Pat. No. 5,302,523). Any method to genetically transform a plant cell may be used within the context of the present invention.

The method also relies on the recovery and use of the plant cells or tissue with the altered properties, particularly plant seed tissue used for feed.

Thus plant cells with altered sugar alcohol metabolism are obtained. Numerous comrpounds are derived from sugar alcohols, but of primary importance is the compound phytic acid or phytate. Methods to reduce phytate in certain plant cells finds great utility in for feed applications.

The genes encoding the enzymes capable of acting on myo-inositol can be natural, synthetic or a combination thereof. The skilled practitioner will readily appreciate that the coding sequence of the gene may be modified to allow for high levels of expression in plant cells. This can be accomplished by altering the sequences of the codons to more correctly resemble the codon usage normally found in the plant cell where the gene will be expressed. Furthermore it is obvious that specific restriction sites may be engineered to allow for convenient manipulation of the coding sequence. It is also contemplated that addition of various sequences such as translational enhancers, introns, etc. may be used to ensure adequate expression of the coding sequence. All of these manipulations are common in the art and will be readily appreciated by the skilled worker.

It is also evident that a tissue-selective promoter can be employed to limit the expression of the enzyme capable of modifying myo-inositol to those tissues wherein phytic acid is made, such as seed tissue. Suitable seed selective promoters include the napin promoter from *Brassica napus,* the phaseolin promoter from Phaseolis, or any other promoter that is seed-selective.

In particular, the use of a myo-inositol O-methyl transferase such as that available from *Mesembryanthemum crystallinum* is contemplated within the scope of the present invention.

The present invention contemplates use of the genetically modified seed produced from the expression of enzymes capable of acting upon myo-inositol, said enzyme being under control of a seed selective promoter. Accordingly levels of phytic acid are reduced. Upon processing of the seed, a meal product is derived with lowered phytic acid content. Accordingly, a feed preparation with reduced phytic acid content is also obtained as a result of the method.

The present invention provides a means to produce cruciferous seeds with reduced phytic acid content. In particular the use of a myo-inositol O-methyl transferase such as that from *Mesembryanthemum crystallinum* to reduce the levels of phytic acid in cruciferous crops is contemplated within the scope of the present invention. The skilled artisan will readily appreciate that the production of meal with reduced phytic acid content from cruciferous seeds can be accomplished as a result of the present invention.

It is known that the presence of phytic acid in seed meals in detrimental to fish raised in aquaculture. However, some seed meals, such as canola seed meal, have a protein composition which is suitable for fish nutrition. The high concentration of phytic acid in canola meal restricts the amount that can be used in a fish diet. Therefore reduced phytic acid meal produced from cruciferous seeds has great utility in aquaculture.

Accordingly the present invention finds utility for the prcduction of seed with modified phytic acid content and seed meal with reduced phytic acid content. The modified seed and meal has utility in a number of feed applications including poultry, swine, aquaculture, ruminant and non-ruminant animals. It is further evident by the foregoing description that any number of different enzymes can be used to modify myo-inositol within the scope of the present invention. It is also evident that various combinations of these enzymes using seed-selective promoters can be used to achieve a specific reduction of phytic acid.

The application of the invention to the sugar alcohol secondary pathway is not limited to the exemplified plant species. Indeed, any plant species that produces phytic acid can be modified by the method of the present invention. The method provides utility in any crop species since the enzyme used, O-methyl transferase is heterologous to all major crop species of commercial importance. Thus any crop species which is used for animal feed or produces seed that is used in part or in whole for animal feed can be modified by the present method to produce plants with reduced phytate content. Accordingly the method can be applied across any crop, including monocots (e.g. corn, rice, wheat, barley, rye) and dicots (e.g. soybean, cotton, alfalfa, Brassica, flax, sunflower, etc).

Modification of both phenylpropanoid and sugar alcohol metabolism is achieved by the present method, providing specific examples as to how the reduction of specific metabolic compounds, in particular anti-nutritional compounds, is achieved in a reliable and predictable fashion according to the method of the present invention.

It is evident to those skilled in the art that any secondary metabolic pathway can be altered within the scope of the present invention. The invention has been demonstrated in two unrelated secondary metabolic pathways and provides predictable and tangible results. The reduction of anti-nutritional agents in, for example, canola plant cells, corn plant cells, rice plant cells, and cotton plant cells is achieved under the broad teachings of the invention.

As a part of the method of the present invention, the skilled practitioner is directed to evaluate the production of the specific secondary metabolite. Hence the skilled artisan will readily appreciate that a basic understanding is required of the tissues wherein the secondary metabolite or compound used as a precursor thereto is synthesized in addition to the developmental time frame wherein it is made. Such information will provide guidance for the selection of a promoter to control the expression of the enzyme that acts upon the secondary metabolite or precursor thereto. In this fashion the skilled reader readily appreciates that the targeting of a secondary metabolite will require an enzyme capable of acting on a precursor to said secondary metabolite in the tissue wherein said secondary metabolite is made as well as during a developmental time frame wherein it is made. Thus the enzyme that acts upon the precursor to the said secondary metabolite should be expressed at or about the time of synthesis of said precursor.

The skilled worker is further directed to carry out a biochemical analysis of the tissue wherein the invention is to be practised. Said analysis may include determination of the levels of various compounds in the tissue throughout development, any compartmentalization or subcellular location of biosynthesis, the period in time during development when the compound is first synthesized or no longer synthesized and any other relevant biochemical information. By carrying out this analysis the skilled artisan will be able to select a promoter which provides suitable levels of expression to introduce the desired change in secondary metabolite content in the plant tissue. It is appreciated that even small alterations in the levels of compounds used as precursors may provide the desired effect.

For example, as a part of the phytic acid embodiment of the present invention, the skilled practitioner will readily appreciate that a basic understanding of the tissues wherein phytic acid is synthesized in addition to the developmental time frame wherein phytic acid is made will provide guidance for the selection of a promoter to control the expression of the enzyme that acts upon myo-inositol. In this fashion the skilled reader readily appreciates that the targeting of myo-inositol will require the enzyme capable of acting on myo-inositol in the tissue wherein phytic acid is made as well as a developmental time frame wherein phytic acid is made. Thus the enzyme that acts upon myo-inositol should be expressed at or about the time of synthesis of phytic acid. The level of expression of the enzyme can be modified to achieve a specific level of reduction of phytic acid. This level of reduction can range from a small percent to nearly the complete elimination of phytic acid. The skilled artisan will readily appreciate that reduction of phytic acid, especially in certain crop species high in phytic acid may require higher expression levels of the gene that modifies myo-inositol than in those crop species where phytic acid is present in lower levels. Manipulation of expression levels by various means is well known in the art. This can include the addition of DNA sequences that enhance translation, strong promoters that provide high levels of transcription or addition of DNA sequences, such as matrix attachment or scaffold attachment regions that appear to provide reliable levels of high transcriptionto transgenes.

This embodiment of present invention also contemplates the production of plant tissue, in particular plant seed that has utility for feed applications. Both the direct feeding of seed and the use of modified meal from processed seed is within the scope of the present invention. The reduction of phytic acid content in plant seeds is desirable in feed applications and the genetically modified seed with altered phytic acid content has great utility in the feed industry.

In some applications, whole grain can be fed to animals or the grain is minimally processed, but not fractionated. For example, grain corn is often used for feed with minimal processing. However, some corn grain is processed and the resultant processing products, such as corn gluten meal are also fed to animals. Both types of corn feed can benefit from reduced phytic acid levels, particularly as it relates to environmental degradation due to excess phosphorous excreted from animals. Other grains used for feed such as wheat, barley and oats can also benefit from the present invention. Thus the present invention finds utility across a wide range of economically important crop species. The gene demonstrated in the present invention to alter myo-inositol levels will be found to work in any crop species since myo-inositol is found in all crop species and is the only known precursor for phytic acid biosynthesis. Thus the utility of the methyl-transferase gene used to alter myo-inositol has been clearly demonstrated. The skilled artisan may readily appreciate that the coding sequence of the coding region or the specific DNA sequence of the promoter or untranslated leader sequence, terminator, etc., may be modified to ensure optimal expression in the plant cell of the particular plant species. This is all within the skill of the ordinary artisan. Thus it is fully anticipated that the present invention can be practiced in any plant species capable of being genetically transformed, including those plant species where the grain is directly used for feed application or those plant species where the grain is processed before being used for feed applications.

Accordingly a whole seed feed preparation with reduced phytic acid content is produced as a result of the method.

In addition to direct feeding of whole or partially disrupted seed, there are many methods used to produce seed meal. Wet milling of corn is used to produce, among other products, corn gluten meal. In addition to processed corn feed products, whole corn grain with reduced phytic acid can be produced according to the method of the present invention. The present invention also finds utility in the production of corn gluten meal with reduced phytic acid.

In addition to major feed crops such as corn, oilseed crops provide a large amount of plant meal used for feed. Of particular importance in oilseeds is the production of meal during extraction of oil. In general, oil is extracted from oilseeds using either a solvent or non-solvent process. The "cake" or expelled solids produced by this process is used for meal formulations and usually contains the majority of the phytic acid content of the seed.

The most common processing for oilseeds involve the extraction of the oil and the recovery of the cake or residual components of the seed following oil extraction. The present invention finds utility in this process and the resultant meal products can be more valuable that conventionally produced meal due to the reduced phytic acid.

Hence a method to produce meal with lower phytic acid content provides a novel composition not currently found in meal derived from oilseeds. Major oilseed crops that will benefit from the present invention include cruciferous oilseed crops such as Brassica napus, Brassica rapa, Brassica juncea, Brassica nigra, Sinapis alba, Crambe, Eruca sativa, and other crucifer oilseeds that may be commercially important and be used for meal. Non-cruciferous oilseeds that are often used in meal applications include soybean, cotton, corn, safflower, sunflower and peanut.

The present invention contemplates use of the genetically modified oilseed produced from the expression of enzymes capable of acting upon myo-inositol, said enzyme being under control of a seed selective promoter. Accordingly levels of phytic acid are reduced. Upon processing of the oilseed a meal product is derived with lowered phytic acid content.

The following examples serve to illustrate the method and in no way limit the scope of the invention.

EXAMPLE 1

General Methods Employed for the Identification of Phenylpropanoid Pathway Products: Determination of Sinapine Content, a Terminal Product of the Phenylpopanoid Pathway in Cruciferous Seeds It is apparent that the skilled artisan can adapt all of the illustrated methods for determination of products of the phenylpropanoid pathway by reference to numerous publications in analytical chemistry. In the first method exemplified, a simple assay for the identification of sinapine in a plant tissue, namely seed tissue from cruciferous plants was adapted from published methods (Chapple, C. C. S., T. Vogt, B. E. Ellis and C. R. Somerville, 1992, Plant Cell 4:1413–1424). A thin layer chromatography (TLC) protocol was standardized for estimation of the phenylpropanoid pathway product sinapine. This method employed separation of plant extracts and a known amount of sinapine spotted on silica plates (for example, Whatman 60A SilicaG). Sinapine can be purified by published methods (for example, D. Strack, 1977, Z. Pflanzenphysiol. 84: 139–145). Separation was by movement of a solvent mixture of n-butanol, acetic acid and water at a proportion of 10:2:3, respectively, to approximately 10 cm from the origin. Seed extracts were prepared by soaking overnight pre-weighed sample in a tightly closed tube containing 100–500 microliters of methanol solution (98% methanol, 2% acetic acid) followed by addition of an equal volume of methanol as added before and grinding. The supernatant was obtained after centrifugation ca. 12,000×g. The supernatant was extracted with a chloroform:water (CW; 400 microliters: 100 microliters) mix and it was centrifuged as above and the lipid phase was removed and the aqueous phase was air dried or dried under vacuum. The samples were dissolved in water and spotted on TLC plates. A defined amount of the sample as determined from empirical attempts was spotted on TLC plates prior to exposing to ascending solvent. Dry weight measurements where used were obtained by drying and then weighing a known amount of fresh samples.

The TLC plate was then viewed under UV light and sinapine was visualized as a brilliant spot. A previously purified sample of sinapine was used as a standard, alone and also as an artificial mix with a seed extract to ensure that the purified sinapine migrated with the sinapine in the seed extract when present with the components of seed extracts. When radioactively labelled sinapine was monitored, the TLC plates were scanned in an Ambis4000 (Scanalytics) scanner that quantitatively images radioactive emissions.

Subsequently, high pressure liquid chromatography (HPLC) was used to verify the sinapine content. Methanol extracts of plant material as above but without chloroform-water extraction were subjected to HPLC analysis in a Varian HPLC instrument fitted with a Nucleosil C18AB column. The injection volume was typically 10 microliters and the mobile phase wits a mix of Solvent A (2% acetic acid in water) and Solvent B (2% acetic acid in acetonitrile). A typical run condition would involve in the mobile phase: Solvent A varied from 90% to 80% over 17 minutes, followed by a further drop to 10% over 1 minute. The column was held at 10% Solvent A for four minutes then flushed and equilibrated with 90% Solvent A. These conditions can be varied to enhance separation of eluted substances. For example, Solvent A can be changed from 90% from the initial time to 80% over 15 minutes to 70% over 15 minutes and then to 10% over 2 minutes followed by another 2 minutes at 10% and equilibration with 90%. A diode array detector was used to monitor UW absorbance. UV absorbance at 330 narometer setting was used for sample analysis. A standard curve with purified sinapine was constructed and used for quantitation of sinapine in plant extracts. It is obvious to a skilled artisan that the HPLC conditions (for example, the proportions and gradient of solvents, different types of solvents) might be varied. It is desirable to determine the conditions that suit the equipment and the complexity of the sample that is applied. The published literature teaches a variety of HPLC methods to analyse phenolic compounds including sinapine.

Radioactive tracer studies were used to obtain a more accurate representation of the onset of sinapine synthesis and for determination of the proportion of newly synthesized sinapine in various parts of a seed. The radioactive tracer method can also be used to determine the competence of the individual seed components (e.g. cotyledons, embryo, seed coat) to synthesize sinapine from an exogenous supply of choline. Radiolabelled products may then be analysed for sinapine, for example, by the TLC protocol followed by scanmirLg by Ambis4000.

The HPLC protocol was employed for quantitative analysis of total sinapine content in seeds and seed components. TLC was used for qualitative analysis of the sinapine content at various stages of seed development, and the radioactive tracer along with TLC followed by counting of the radioactive spots was used for determination of the onset and distribution of sinapine in seeds and seed tissue such as cotyledons, axes and seedcoat.

The radioactive tracer method for establishing de novo synthesis of sinapine from choline employed whole pods (siliques), rather than isolated seeds, in order to provide experimental conditions as representative as possible of in vivo conditions. Siliques from various stages of development were obtained from plants grown under controlled conditions, typically 20° C. daytime temperature, 15° C. night temperatures, on a 16/8 hour day/night cycle. The pedicel portion of the silique was immersed in a solution containing $^{14}$C-labelled choline purchased from New England Nuclear (Stock specific activity of 2.0 GBq/mmol; concentration, 7.4 MBq/ml which is the same as 0.2 mCi/ml; choline, 3.7 micromol/ml). Siliques with their pedicel immersedin a tube containing 1.8 ml of an aqueous medium such as half-strength Murashige-Skoog medium and 1 mM non-radioactive choline and 1.8 to 9 microliters of the radioactive choline stock were incubated in a plant growth chamber for 24 to 72 h with a day/night cycle of 16 hr light/8 hr dark at a temperature of 20° C. The light conditions were 51 microEinsteins/sq.m per second and the seeds removed from these pods were used in TLC analysis. These samples were extracted in methanol solution followed by chloroform-water (CW) extraction as described above.

Where older seeds were analysed, in addition to the above method, infiltration of seeds separated from siliques was done. Twenty seeds were infiltrated with in 500 microliter of the radioactive choline medium described above under a light vacuum for 15 minutes at room temperature of ca. 23° C. The radioactive medium was then removed and replaced with 500 microliters of non-radioactive medium of above composition, less $^{14}$C-choline and incubated at 23° C. for 24 hrs. The seeds were then extracted as above.

The plant material can also be extracted by mixture of chloroform:methanol:formic acid (CMF) in a proportion of 5:12:3, respectively. Typically, 2 microliter of CMF per mg of sample is added, the sample is ground and left at room temperature (21–23° C.) overnight (16 hours) followed by centrifugation at ca. 12,000×g for 5 min. The supernatant is collected and the pellet is mixed thoroughly with another volume of CMF as added before, left for 20 min. and centrifuged as above. The supernatants are pooled, a chloroform-water (CW) extraction was performed as described before and the aqueous fraction was analysed as before.

EXAMPLE 2

Identification of the Location of the Synthesis of a Product of the Phenylpropanoid Pathway in a Specific Tissue In this example, the developmental timing of synthesis of a product of the phenylpropanoid pathway was determined. This particular example illustrates sinapine synthesis and accumulation within cruciferous seed tissue. In this example, developing seeds of *Brassica napus* were used. TLC analysis of extracts of siliques obtained from hand-pollinated flowers was performed to establish the time of onset of sinapine accumulation. Samples were taken 7, 14, 16, 18, 20, 22, 24, 26, 28, 30, 32, and 34 days after pollination (DAP) and after seed maturity. Seed extracts were prepared according to the methods described in Example 1 and the sinapine content visualized by TLC analysis. Sinapine was evident from 18 DAP to seed maturity, and maturing seeds were shown to contain the greatest amount of sinapine, suggesting that there was a net accumulation in developing seeds.

The pod wall fraction from which the seeds were removed did not contain sinapine, and sinapine was absent in younger seeds from samples at 7- 14- and 16-DAP. This analysis indicated the onset of sinapine accumulation was approximately 18 DAP, however, since this method employs UV fluorescence detection, the presence of very small amounts, if any, in younger seeds would not be detectable. FIG. 3 shows an example of a TLC analysis of samples up to 28 DAP and the second plate shows an example up to seed maturity. As the above results were not quantitative, HPLC analysis of whole seed extracts, obtained with a methanol solution as described in Example 1, was performed. The results presented in FIG. 4 confirm the onset of sinapine synthesis from 20 DAP increasing rapidly and continually to maturity. The amount of sinapine in mature seeds was ca. 0.8% on the basis of seed dry weight and since oil would account for about 45% of the seed, this would translate to ca. 1.5% of de-fatted seed meal.

EXAMPLE 3

Determination of the Temporal and Spatial Aspects of the Synthesis of a Product in the Phenylpropanoid Pathway—Sinapine Synthesis with Reference to Seed Development Based on the information obtained in Example 2, it was further demonstrated that sinapine is synthesized by developing seeds. It was also evident that sinapine degradation was minimal during seed development. In order to confirm this analysis, developing seeds were incubated with $^{14}$C-choline, a precursor used for the synthesis of sinapine from sinapoyl-glucose, a terminal step in the phenylpropanoid pathway in plants. The presence of the radioactive precursor resulted in the production of labelled sinapine. Thus it is possible to quantify the biosynthesis of sinapine by this method. As shown in FIG. 5, sinapine synthesis (incorporation of $^{14}$C-choline into sinapine) was undetectable at 10 DAP, and first appeared at 14 DAP. Thus sinapine synthesis (i.e. the production of the final product sinapine from the precursors sinapoyl-glucose and choline) takes place from 14 DAP to near mature seeds. Accordingly the onset of sinapine accumulation in seed occurs after 14 DAP, and developing seeds continue to synthesize and accumulate sinapine to maturity.

Although 18 DAP appears to be the time at which sinapine accumulation becomes visible in non-radioactive analysis, the radioactive assay is more sensitive and allows the detection of even small amounts of biosynthesis to be detected. Hence, as shown by the radioactive assay, sinapine synthesis first begins at a low rate at 14 DAP. Infiltration studies show that the capacity to synthesize sinapine is present in older, near-mature seeds as well (FIG. 6).

In addition to determining the developmental time frame of accumulation of products of the phenylpropanoid pathway, the skilled artisan is further directed to determine the tissue specificity of biosynthesis of the product of the phenylpropanoid pathway. In this portion of the example, the sinapine accumulation in cotyledons, axes and seedcoat was measured. Radioactive tracer analysis was performed with whole siliques from 18 to 42 DAP. The pedicel of excised siliques was immersed in a solution containing $^{14}$C-choline for 24 to 72 h and the three seed components were dissected and analysed for sinapine. The results summarized in FIG. 7 showed that cotyledons contained the maximum amount of sinapine (on a per seed basis) followed by the axes and seedcoat. Sinapine extracts from the cotyledons and axes of seeds from 25 DAP to maturity showed that, on a dry weight basis, the axes contained about 50% of sinapine of the cotyledons (FIG. 8). However, as cotyledons are relatively greater in mass in comparison to axes (ca. six times the weight of axes at maturity) their sinapine content contributes up to 90% of the total sinapine found in the seed (FIG. 9).

EXAMPLE 4

Genetic Transformation of a Plant with a Gene Encoding an Enzyme Capable of Acting on a Precursor of the Phenylpropanoid Pathway In this example, an enzyme, choline oxidase (COX) which acts upon the precursor used for sinapine synthesis is expressed in a plant cell. The enzyme choline oxidase is inserted into a plant transformation vector under the control of a seed-selective promoter. Choline is a precursor for the production of sinapine from sinapoyl-glucose, hence reduction of the choline pool reduces the production of sinapine.

Genetic transformation of *Brassica napus*, a cruciferous plant species, with a seed selective choline oxidase (COX) construct. The DNA sequence of the choline oxidase gene is shown in FIG. 10, while the predicted amino acid sequence is shown in FIG. 11. To provide seed specific expression, a napin promoter sequence (Kohno-Murase, J., M. Murase, H. Ichikawa, and J. Imamura, 1994, Plant Molecular Biology, 26:115–1124) was used. This final plasmid, pHS731, was constructed by a series of cloning and subcloning according to standard protocols described in such manuals as Maniatis, T., Frittsch, B. F., and Sambrook, J. (1982; Molecular Cloning: A Laboratory Manual, Cold Spring Harbor, N.Y.). The vector backbone is from RD400 (Datla, R. S. S., Hammerlindl, J. K., Panchuk, B., Pelcher, L. E., and Keller, W., 1992, Gene 211:383–384) which as been modified to include, instead of the NosP-NptII plant selection marker of RD400, a fusion gene between gus and npt (Gus::npt). The Gus-npt has been described previously (Datla, R. S. S., Hammerlindl, J. K., Pelcher, L. E., Crosby, W. L., and G. Selvaraj, 1991, Gene 101: 239–246). It was cloned as 2.6 Kb fragment, containing the Nos terminator (polyA signal) at the end of the npt sequence, from pGKK14 (Datla et al, 1991) into an intermediary plasmid that has lost the entire T-DNA of RD400. A partially duplicated CaMV35S promoter along with the Alfalfa Mosaic Virus leader from pBI525 (Datla, R. S. S., F. Bekkaoui, J. K. Hammerlindl, G. Pilate, D. I. Dunstan and W. L. Crosby, 1993, Plant Science 94:139–149) was cloned as a HindIII-BamHI fragment at the 5' end of the Gus:npt sequence. The sites for HindIII, BamHI and an adjacent XbaI sites were removed by filling the ends with Klenow fragment of Polymerase I to give pHS722. A functional lac-alpha region containing the multiple cloning sites from pTZ19R (Mead, D. A., E. Szczesna-Skorupa, and B. Kemper, 1986, Protein Engineering 1:67–74) was obtained as 0.26 Kb fragment by polymerase chain reaction. This fragment was digested with MunI and EcoRI and introduced into an EcoRI site of pHS722 to give pHS723. The nucleotide sequence of a portion of the T-DNA of the vector was determined and the unique sites in the multiple cloning sites were identified by restriction analysis. pHS725 is a derivative originating from pHS723 and containing the open frame of choline oxidase originally from pKR11 (see Rozwadowski et al., 1991) via a series of intermediary vectors that provided convenient sites or such features as Cauliflower Mosaic Virus Poly A Signal. The pHS725 vector provides in the pHS723 background COX open reading frame with a PolyA signal of CaMV at the 3' end. The 5' portion of the open reading frame containing CaMV35S promoter was replaced with a napin promoter from an intermediary plasmid to give pHS731. The intermediary plasmid comprised a pUC19 derivative containing a 1.1 Kb napin promoter as a HindIII-NapinP-BamHI cassette, received from J. Kohno-Murase (Kohno-Murase et al., 1994) which was ligated as a HindIII-BamHI insert into HindIII-BamHI window of plasmid RD400 (Datla et al., 1992). The resulting plasmid was pHS974. The BamHI-BADH open reading frame-PolyA-KpnI cassette was isolated as a 2.1 Kb fragment from pRKJ6A (pRKJ6A is described in detail in R. K. Jain, 1995, Genetic Engineering of Osmolyte Biosynthesis in Plants: Manipulation of Betaine Aldehyde Dehydrogenase Gene Expression Tobacco, Ph.D. Thesis, University of Saskatchewan, Saskatoon, Canada), and ligated to the BamHI-Kpn I window of pHS974 resulting in pHS981. pHS981 was used in the derivation of pHS731. FIG. 12 shows the resulting plasmid pHS731 that contains with a Right and Left border napin promoter-Cox open reading frame-CaMV polyA signal. The nucleotide sequence of the napin promoter-Cox open reading frame-CaMV polyA signal segment has been determined from the components. Additional sequence confirmation is also possible because pHS723's ancestry includes all of pBIN19 (Bevan, M., 1984, Nucleic Acids Research 12: 8711–8721), including the right and left border and all of the region outside of it. The complete nucleotide sequence of pBIN19 has been published. Thus the COX gene construct described above can easily be retrieved for cloning into other vectors. The plasmid vector pHS731 in *E. coli* DH5 has been deposited on Jan. 22, 1997 with the American Type Culture Collection (ATCC), 12301 Parklawn Drive, Rockville Md., USA 20852, under accession number ATCC Designation 98300.

Based upon published information (DeLisle, A. J., and Crouch, M. L., 1989, Plant Physiology 91:617–623; Hoglund, A.-S., T. Rodin, E. Larsson, and L. Rask, 1992, Plant Physiology, 98:509–515) and our results with a napin promoter, napin gene expression was expected to span the middle portion of the temporal development of *B. napus* seeds.

The vector pHS731 was inserted into Agrobacterium stain MP90 by standard triparental mating followed by Agrobacterium-mediated transformation of Brassica. Transformation was essentially carried out as described by Moloney et al., 1989, Plant Cell Reports 8:238–242.

*Agrobacterium tumifaciens* strain GV3101/pMP90 (Koncz C. & Schell, J., 1986, Mol. Gen. Genet. 204:383–396) harboring the binary vector pHS731 was used for transformation studies. A stationary phase bacterial culture in LB broth (Difco, USA) (100 ml) was harvested by centrifugation and resuspended in 10 ml fresh LB broth with 1% DMSO (dimethyl sulfoxicle) (Sigma, USA) as a cryoprotectant. Aliquots of 200 $\mu$l were stored at 10–20° C. until used for transformation wherein a bacterial aliquot was added to 2 ml Brain Heart Infusion Broth (Difco, USA) containing 2% sucrose, 50 $\mu$M acetosyringone, pH 5. 6 and incubated overnight at 28° C. Bacterial cell density was approximately $1 \times 10^9$ cells per ml.

Cotyledonary explants were exposed to Agrobacterium containing the plant transformation vector according to the method of Moloney et al, 1989, Plant Cell Rep. 8:238–242. The cut surface of the petiole of the explants was briefly submerged into the bacterial culture. The explants were inserted into co-cultivation medium such that the cut surface was in contact with the medium. Ten explants were placed in each 100×15 mm Petri plate. Co-cultivation plates were sealed with Stretch'n Seal™ plastic wrap. Plates were incubated for three days in a growth cabinet with temperature and photoperiod conditions, as above, with respect to the seed germination step. The explants were then transferred to selection medium.

After 3 to 4 weeks in the selection medium, regenerating green shoots (putative transformants) were excised and transferred to fresh selection medium for continued growth. When shoots attained a length of 1.5–2.0 cm they were transferred to rooting medium. Putative transgenic shoots were screened for expression of the gus gene essentially as described by Jefferson, R. A., 1987, Plant Mol. Biol. Rep. 5:387–405. The presence of blue staining was regarded as evidence of transformation.

Confirmation of transformation was established by NPTII and PAT assays, Southern blots, PCR (Polymerase Chain Reaction) and progeny analysis. Transgenic seeds of *Brassica napus*, cv. Westar containing the vector pHS731 referred to as 202622 have been deposited on Jan. 22, 1997 with the American Type Culture Collection, (ATCC), 12301 Parklawn Drive, Rockville Md., USA 20852, under accession number ATCC Designation 97854.

Expression of a choline oxidase gene in *Brassica napus* seeds was then determined. Several independent transgenic lines were regenerated. COX activity was demonstrated by using a coupled enzymatic reaction. COX produces betaine aldehyde from choline and this betaine aldehyde can be assayed easily by NAD-dependent oxidation of it by a BADH. NAD reduction is monitored by change in absorbance at 340 nm. In order to standardize the assay, variable amounts of commercially available Cox (e.g., Sigma) and a constant amount of *E. coli* BADH (50 Units; 1 U=1 nmol of NAD reduced per min. per mg protein) preparation from a BADH-overexpressing bacterial strain is used to standardize the reaction conditions and to establish a standard curve such that COX but not BADH is limiting. The assay is then performed with plant extracts from transgenic lines and controls. BADH can be enriched or purified by published methods (e.g., Falkenberg, P. and Strom, A. R., 1990, Biochemica Biophysica Acta 1034:253–259).

Plant extracts were obtained as follows. Plant leaves of approximately 100 mg are frozen liquid nitrogen, ground with an ice-chilled extraction buffer at two volumes for the weight of the sample. The samples were centrifuged at ca. 10,000×g and the supernatant was centrifuged again. The centrifugation was repeated until no particulate matter was visible. With seeds, ca. 20 seeds, per sample, after the first centrifugation 20 mg of activated charcoal was added and the remainder of the procedure was followed. The extraction buffer, pH 8.0 adjusted by KOH, contains, per 100 ml, 1.92 g of HEPES, 0.2 ml of 0.5M EDTA, 10 ml of glycerol and deionized water to make it up to 100 ml. Prior to the assay, DTT from a stock of 1M was added to a final concentration of 25 mM and a complete protease inhibitor cocktail (Boehringer-Mannheim, Catalog: 1697-498) from a 10× stock in HEPES buffer was added. The enzyme assay buffer (BADH buffer) contains 50 mM HEPES-KOH, pH8.0, 1 mM EDTA, and freshly added DTT to 1 mM final concentration. The coupled assay was performed in a reaction containing 50 microliters of BADH buffer, 50 microliters of an NAD stock of 10 mM, 50 microliters of plant sample, 30 microliters or equivalent to give 50 U of BADH, and deionized water to make up the volume to 450 microliters. The reaction mix was mixed and after monitoring for 20 min. For background changes in absorbance at 340 nm, 50 microliters of choline chloride was added and spectrophotometric reading was continued for 10 to 20 minutes. For a standard curve, a plant sample was omitted, and various amounts of purified COX were added instead. Units were calculated using a programmable, recording spectrophotometer of the type Beckman DU65. A skilled artisan can modify the protocols to suit availability of equipment using biochemical data available in the literature for extinction coefficient for NAD. NAD reduction itself is a standard assay performed for dehydrogenases.

EXAMPLE 5

Analysis of Transgenic Seeds for Reduced Phenolic Content

In this example, seeds were analysed for sinapine content. The seeds from transgenic plants recovered in Example 4 were grown to obtain selfed progeny, and these progeny lines were analyzed for segregation or lack thereof of a transgene encoding beta glucuronidase (GUS) activity. This gene (see Datla, R. S. S., Hammerlindl, J. K., Pelcher, L. E., Crosby, W. L., and G. Selvaraj, 1991, Gene 101: 239–246) is present within the right and left borders of the T-DNA of the vector pHS731 and thus serves as a convenient marker in genetic analysis of segregation. Lack of genetic segregation indicated homozygous nature of the plant from which the progeny originated. Those lines that showed segregation were hemizygous and the segregants lacking GUS activity were retained as controls that did not contain COX gene. Thus, there were pools of homozygous lines containing COX and their counterparts not containing the transgene. These lines were analyzed for their sinapine content by an HPLC protocol. The results shown in FIG. 13 clearly show that transgenic segregants have significantly reduced sinapine levels in contrast to their non-transgenic counterparts. The non-transgenic segregants offer the best control because they arise from the same primary transgenic plant. These results demonstrate the utility of the described method. It is obvious to a skilled artisan that various levels of reduction may be accomplished by changing the levels, timing and location of gene expression, and also looking for beneficial variants among individual transgenic lines that show desirable results due to a variety of reasons that include position effects and copy number.

EXAMPLE 6

Production of an Stress Protectant Product by Diversion of a Precursor within the Phenylpropanoid Pathway In this example, the stress protectant betaine was produced by the combined activity of COX and BADH, both under the control of a seed-selective promoter. As a first part of this example, transgenic *Brassica napus* carrying the BADH gene under the control of a seed-selective promoter were produced. Analysis of these plants for BADH expression was carried out.

Expression of a betaine aldehyde dehydrogenase gene in *Brassica napus* seeds. An *E. coli* BADH gene (betB) is isolated and manipulated for seed-specific expression by linkage to a *B. napus* napin promoter (Boyd et al., Gene 103:45–52 (1990)). Plasmid RD400 (Datla, R. S. S., Hammerlindl, J. K., Panchuk, B., Pelcher, L. E., and Keller, W., 1992, Gene 211:383–384) was used as the vector from which the final derivative pHS974 containing within the right and left T-DNA borders the open reading frame of betB from its ATG site under the expression control of a napin promoter and a cauliflower mosaic virus PolyA signal was obtained. The Napin-betB-PolyA cassette (ca. 3.3 Kbp) comprised, in the indicated order: HindIII site, Napin promoter, BamHI site, betB ORF, EcoRI site-PolyA signal of cauliflower mosaic virus DNA, KpnI site, and EcoRI site. The napin promoter was from Kohno-Murase et al. (Plant Molecular Biology, 26:115–1124, 1994) and the PolyA signal was originally from plasmid pJIT117 (Guerineau, F., Woolston, S., Brooks, L., and Mullineaux, 1988, Nucleic Acids Research 16:11380). The final plasmid pHS981 of ca. 15 Kbp is shown in FIG. 14. This was introduced into *Agrobacterium tumefaciens* GV3101[pMP90] (Koncz, C., and Schell, J., 1986, Molecular and General Genetics 204: 383–396) and the resultant strain was used for genetic transformation of *Brassica napus*.

Several transgenic lines were obtained and the seeds at various developmental stages were assayed for BADH activity. BADH activity was found to peak around 35 DAP, and mature seeds retained residual activity. Specific activity as a function of developmental stage demonstrated that the onset of BADH activity is concomitant with sinapine synthesis.

The lines expressing the BADH gene were crossed with the lines carrying the COX gene described in Example 4. Plants containing the COX gene and plants containing both the BADH and COX genes were analyzed for sinapine content and total phenolic content. These results are shown in FIG. 15 (sinapine content) and FIG. 16 (total phenolic content). The seeds analyzed were harvested from plants cultivated under field conditions in the summer of 1999. As shown in FIG. 15, the combined activity of COX and BADH lead to a further reduction of sinapine accumulation over the activity of COX alone. As shown in FIG. 16, there is a reduction in total phenolic content in transgenic plants relative to control.

EXAMPLE 7

Nucleotide Sequence of a Synthetic Ferulic Acid Decarboxylase Gene

In this example, the published sequence of ferulic acid decarboxylase from *Bacillus pumilus* (Zago et al., Applied and Environmental Microbiology 61:4484–4486, 1995) was used for the construction of a gene optimized for expression in plant cells. The ferulic acid decarboxylase open reading frame was synthesized by ligating synthetic oligonucleotides based on the published sequence. The oligonucleotides were synthesized based largely on the codon preference of highly expressed genes of *Brassica napus*.

The synthetic oligonucleotides were approximately 60 nucleotides long. The design of the oligonucleotide duplexes included at the 5' end a BamHI-cohesive end (5' GATC-) and an EcoRI cohesive terminus (3'-TTAA-5') at the 3' end. The individual duplexes were assembled and a full-length open reading frame with 5' BamHI and 3' EcoRI sites was formed. The ligation reactions were according to standard protocols. The ligation products were in turn ligated into a cloning vector.

Upon ligation of the above synthetic gene into the BamHI-EcoRI cleaved pBluescript SK– (Statagene), clones with a 0.5 kb insert were identified by screening of miniprep plasmid DNA from *E. coli* clones. The potential candidates were screened, and the nucleotide sequence of two of the clones were determined. It was found that each of the clones had a point mutation and these two point mutations were spaced apart in the two clones chosen. The spacing of the mutations allowed for re-construction of an intact gene from combining two non-mutated portions of the gene from these clones. This clone is referred to as pGS97b1. The nucleotide sequence of this synthetic gene is shown in FIG. 17. The predicted amino acid sequence is shown in FIG. 18.

The functionality of the synthetic gene was ascertained by a simple test. Ferulic acid decarboxylase converts ferulic acid to 4-vinylguaiacol (4-VG). 4-VG has a distinct odor of cloves and 4-VG is believed to be the single most important compound that imparts the natural aroma of cloves. *Escherichia coli* strain with pGS97b1 when grown in the presence of 1 mM ferulic acid in the growth medium gave a distinct clove odor, whereas the culture without ferulic acid or a culture of a strain with the vector alone did not produce the odor. HPLC analysis of cultures fed with ferulic acid confirmed the disappearance of ferulic acid. Based on the above results it was concluded that a functional gene is cloned in pGS97b1.

EXAMPLE 8

Genetic Transformation of a Plant with a Gene Encoding Ferulic Acid Decarboxylase Under the Control of a Consitutive Promoter In this example, an enzyme, ferulic acid decarboxylase cloned in pGS97b1 was inserted into a plant transformation vector RD400 (Datla, R. S. S., Haumerlindl, J. K., Panchuk, B., Pelcher, L. E., and Keller, W., 1992, Gene 211:383–384) which has been modified to include instead of the NosP-NptII plant selection marker of RD400 a fusion gene between gus and npt (Gus:npt). The Gus-npt has been described previously (Datla, R. S. S., Hammerlindl, J. K., Pelcher, L. E., Crosby, W. L., and G. Selvaraj, 1991, Gene 101: 239–246). The ferulic acid decarboxylase gene was placed under the control of the 35S promoter and the plasmid was used to transform tobacco plants according to standard protocols.

The restriction map of the vector is shown in FIG. 19. The vector pG897b3 as shown in FIG. 19 is similar to pHS731 except as follows. On the same vector backbone of pHS731, the HindIII-napin P-BamHI cassette has been replaced with a cauliflower mosaic virus 35S promoter-alfalfa mosaic virus leader cassette (described in R. S. S. Datla, F. Bekkaoui, J. K. Hammerlindl, G. Pilate, D. I. Dunstan and W. L. Crosby. Improved high-level constitutive foreign gene expression in plants using an AMV RNA4 untranslated leader sequence, Plant Science 94: 139–149, 1993). This promoter portion is abbreviated as 35S in FIG. 19. Following the 35S is the open reading frame of ferulate decarboxylase bound by BamHI at the 5'end and EcoRI at the 3' end instead of the COX open reading frame of pHS731.

Transgenic plants were recovered which express the ferulic acid decarboxylase gene. Plants were analyzed for phenolic content and the production of vinylguaiacol.

Independent transgenic plants of tobacco which carry the ferulic acid decarboxylase gene were found to contain a immunoreactive polypeptide of expected size in western blot analysis with polyclonal antibodies raised against ferulic acid decarboxylase. Non-transformed plants did not have an immunoreactive peptide. This provides proof for transgenic expression of ferulic acid decarboxylase protein in these tranagenic plants.

EXAMPLE 9

Genetic Transformation of a Plant with a Gene Encoding Ferulic Acid Decarboxylase Under the Control of a Tissue Selective Promoter In this example, an enzyme, ferulic acid decarboxylase, cloned in pGS97b1 was inserted into a plant transformation vector RD400. The ferulic acid decarboxylase gene was placed under the control of the seed specific napin promoter from *B. napus* and the plasmid was used to transform tobacco plants according to standard protocols. The restriction map of the vector is shown in FIG. 20. The vector pGS97b2 as shown in FIG. 20 is similar to pGS97b3, except that on the same vector backbone, the HindIII-35S-BamHI cassette has been replaced with the HindIII-napin promoter-BamHI cassette shown in FIG. 12 for pHS731. Transgenic plants were recovered which express the ferulic acid decarboxylase gene. Plant seeds were analyzed for phenolic content and the production of vinylguaiacol.

EXAMPLE 10

Determination of Tissue Specificity and Developmental Pattern of Phytic Acid Accumulation in Developing Seeds of a Cruciferous Plant, *Brassica napus*, Biosynthesis of Phytic Acid In this example, information regarding the biosynthetic pathway of phytic acid was determined in Brassica seed. Since phytic acid is the hexaphosphate derivative of myo-inositol (phytic acid is referred to as $IP_6$), the proportions of individual phosphorylated derivatives of myo-inositol components (e.g. $IP_1$, $IP_2$, $IP_3$, $IP_4$ and $IP_5$) of total phosphorylated inositol derivatives were determined. Pure phytic acid, partially degraded by autoclaving to produce the various phosphorylated derivatives, was used as a standard for HPLC analysis conducted according to Vernon and Bohnert (1992. The EMBO Journal 11:2077–2085) and Vernon D M, Tarczynski M C and Jensen R G and Bohnert H J, (1993. The Plant Journal 4: 199–205).

The various forms of phosphorylated inositol (e.g. $IP_1$, $IP_2$, $IP_3$, $IP_4$ and $IP_5$) and phytic acid were easily distinguishable by this analysis. Only one peak was found when inositol phosphate samples, extracted from Brassica developing seeds, were analyzed which corresponded to $IP_6$, (i.e. phytic acid). This result demonstrated that $IP_6$ is the predominant inositol phosphate form in developing seeds and other phosphorylated inositol intermediate forms could not be detectable by HPLC by the described methods. Accordingly the biosynthesis of phytic acid from myo-inositol is believed to occur in a rapid and essentially quantitative fashion.

Developmental bisoynthesis of phytic acid.

In this portion of the example, the developmental timing of phytic acid accumulation was determined. The methods to determine the phytic acid content of seeds is as follows: Seeds are ground in mortar in the presence of liquid nitrogen and the powder is transferred into 15-ml sterile tube containing 5 ml of 0.5M HCl. After removal of lipids with hexane extraction, the remaining phase (aqueous phase with tissue residues) is sonicated for 90 seconds at level 3 with an ultrasonic liquid processor (Model XL2020, Heat Systems, Inc., Farmingdale, N.Y., USA). Following centrifugation the liquid is transferred to a fresh tube for phytic acid analysis by HPLC. This method was applied to seeds at various developmental stages.

Phytic acid accumulation during seed development is shown in FIG. 21. Although phytic acid is first detectable in seeds at very early stages (i.e. 12 days after pollination), the content did not increase significantly until 22 days after pollination. During a 10-day period following its first appearance, phytic acid reaches a maximum level of approximately 240 ug/seed. Phytic acid content expressed in terms of dry weight of mature seed is approximately 3.2%.

These results indicate that phytic acid reduction through interference with phytic acid biosynthesis requires a promoter that is capable of expression from approximately 12 DAP to near seed maturity.

Further analysis indicated that phytic acid is mainly deposited in embryo tissue rather than in seed coat (FIG. 22). Cotyledons contain almost 90% of the seed phytic acid and 10% is present in the embryo axis. These findings further suggest that the various embryo tissues are the most preferred target tissues for phytic acid reduction by genetic modification of phytic acid biosynthesis.

EXAMPLE 11

Determination of Myo-inositol Metabolism in Developing Seed Tissue

This example illustrates the portion of the myo-inositol pool which is utilized for phytic acid biosynthesis. Although myo-inositol is the precursor for phytic acid synthesis in plants, it also is used in other anabolic pathways for production of phosphatidyinositol and cell wall components. This example illustrates the portion of the total myo-inositol pool that is used for phytic acid biosynthesis in developing seeds. In vivo-labeling of Brassica seeds using $^3$H-myo-inositol was used to track inositol distribution in different fractions extracted with different solvents. The technique used for in vivo pulse labeling of developing seeds with $^3$H-myo-inositol was as follows. Siliques at different developmental stages were removed and the cut end was immediately placed into 10 ml sterile culture medium containing 5 uCi $^3$H-myo-inositol in 50-ml tubes and cultured at standard growth conditions (20° C. for 16 hours under light, 15° C. for 8 hours without light) for two days. The seeds were harvested for extraction of lipids, phytic acids, trifluoroacetic acid (TFA)-soluble cell wall components and cell wall debris. The radioactivity was determined in each fraction by liquid scintillation.

Four types of extractions from pulse-labeled seeds were carried out to separate water-soluble cell components (for phytic acid analysis), hexane-soluble (for lipid analysis), trifluoroacetic acid (TFA)-soluble cell wall components and cell debris. FIG. 23 lists the average radioactivity in each fraction at different stages of seed development. The data indicates that more than 20% of the total label in seeds is found in the lipid fraction at 25–30 days after pollination (DAP). Radioactivity in cell wall fractions (TFA-soluble cell wall and sell debris) accounts for approximately 5% of the total label incorporated during seed development. The radioactivity in the water-soluble fraction was further analyzed by HPLC for identification of the phytic acid portion. It was found that approximately 10% of label in the water-soluble extract is recovered in the phytic acid peak and around 30% of the label is in sample injection peak, which is free myo-inositol. The other labeled material present in the water-soluble extract was recovered in pre- and post-phytic acid peaks, representing unidentified compounds.

The percentage of metabolized label found in phytic acid, lipid, TFA-soluble cell wall and cell debris fractions is shown in FIG. 3. Approximately 30% of the label from $^3$H-myo-inositol-derived metabolites is found in phytic acid at 20 to 30 DAP. Concomitantly, about 60% of the label was present in lipids (inositol-containing phospholipids) and less than 10% in cell wall fraction.

Therefore the portion of the total myo-inositol pool that is utilized for phytic acid biosynthesis is approximately 30% at a period of seed development where phytic acid biosynthesis appears to be at a maximum.

EXAMPLE 12

Cloning of a Gene Encoding an Enzyme Capable of Acting Upon Myo-inositol

In this example, a gene capable of acting upon myo-inositol was isolated. The gene was the inositol O-methyltransferase gene from the common ice plant. Reverse transcriptase cloning was used to isolate the gene as described below. Standard DNA manipulation were carried out according to Maniatis et al, Molecular Cloning, A Laboratory Manual, Cold Spring Harbor Laboratory, Cold Spring Harbor, N.Y.

Total RNA was extracted from 500 mM NaCl treated leaf tissues of ice plant and poly (A)+ RNA was further purified. This mRNA was used for reverse transcription by Superscript II Reverse Trancriptase (Promega,Madison, Wis.) under the following conditions: Three micrograms of mRNA dissolved in 20 microliters of water was used as a template. The RNA was denatured by heating at 65° C. for 5 minutes then chilled on ice. To the mixture was added 3 microliters of oligo-dT (500 micrograms/ml), 8 microliters of 5×reverse transcriptase buffer, 4 microliters of 0.1M DTT, 2 microliters of 10 mM dNTPs. The mixture was warmed to 42° C. then 3 microliters (60 units) of Supertranscript II Reverse transcriptase was added. The reaction was carried out for one hour at 42° C. After this period of time, 1 microliter of Rnase H (1.5 Units/microliter) was added and the reaction was carried out for 30 minutes at 37° C. The resulted cDNA was used as template for PCR by Vent polymerase under the following conditions: The PCR reaction was carried out in a 100 microliter volume with cycles comprising 94° C. for one minute, 55° C. for one minute, 72° C. for one minute with a 2 second extension for each cycle in a total of 30 cycles. The primers used in this reaction were based on the published IMT DNA sequence (GenBank accession number M87340). The forward primer used was Sequence I.D. No. 6:

5'TTTTTGGATCCATGACTACTTACA CAATGGCAACTACA3' which comprises a BamH I site at the 5' end (underlined). The backward primer used was Sequence I.D. No. 7:

5'TTTTTTTTGCGGCCGCATAAAGGCAAATCATACACTG3' which comprises a Not I site at the 5' end (underlined).

The amplified DNA fragment was digested with BamH I and Not I, and then subcloned into pSPORT 1 (BRL, Bethesda, Md.). The Bam HI, Not I digested PCR fragment was cloned into the corresponding sites of the pSPORT vector to derive pSportIMT. FIG. 24 (Sequence I.D. No. 5) shows the sequence of the amplified DNA fragment, which is identical to the published IMT DNA sequence except for a two base difference in the 3' untranslated region. The predicted protein sequence is identical to the published information available from GeneBank.

EXAMPLE 13

Construction of Plant Transformation Vectors with a Gene Encoding an Enzyme Capable of Acting Upon Myo-inositol: Use of the Ice Plant Myo-inositol O-methyl Transferase Gene This example illustrates the construction of a plant transformation vector containing a gene capable of acting on myo-inositol under the control of a promoter active in plant cells. The exemplified plant transformation vector comprises the myo-inositol O-methyl transferase gene under the control of a promoter active in seed cells, the 35S promoter. Construction of the vector was as follows: pSportIMT was digested with Bam HI and Eco RI to release the IMT gene. The IMT gene fragment was cloned into the corresponding sites of pBluescript SK(−), (Strategene, La Jolla, Calif.) and the resultant plasmid is referred to as pBlueIMT. The pBlueIMT was digested with Spe I and cloned into the vector pBI 221 (CloneTech) previously cut with Xba I. A plasmid that contained the IMT gene in the correct orientation relative to the 35S promoter in pBI 221 was chosen and digested with Hind III and Eco RI. The 35S-IMT-Nos terminator fragment was transferred into pRD 400 resulting in the plant transformation vector p35SIMT.

The resultant construct, p35SIMT, contains a 35S promoter-IMT-GUS-Nos terminator cassette in pRD400 and is shown in FIG. 25.

EXAMPLE 14

Construction of Plant Transformation Vectors with a Gene Encoding an Enzyme Capable of Acting Upon Myo-inositol Under the Control of a Seed-selective Promoter In this example a gene encoding an enzyme capable of acting upon myo-inositol under the control of a seed-selective promoter was constructed in a plant transformation vector. The gene used was the myo-inositol O-methyltransferase gene and the promoter was the seed selective napin promoter. The vector is referred to as pNIMT.

The vector pNIMT was constructed as follows: a Spe I-digested IMT DNA fragment (Example 4) was ligated into pDHI at an Xba I site, resulting in a napin promoter-IMT-Nos terminator cassette. This expression cassette was further transferred into pRD400. The resultant vector is shown in FIG. 26.

EXAMPLE 15

Transformation of *Brassica napus* (Westar) with p35SIMT

The vector p35SIMT was inserted into Agrobacterium stain MP90 by standard triparental mating followed by Agrobacterium-mediated transformation of Brassica. Transformation was carried out as described in Example 4. Plants transformed with p35SIMT were obtained and analyzed for phytate content.

EXAMPLE 16

Molecular Analysis of Transgenic Plants $F_0$ transgenic plants comprising the CaMV 35S-IMT expression cassette were analyzed by PCR, Southern and northern blots as well as IMT enzyme assay. Preliminary PCR analysis indicated that all the transgenic plants contained the IMT gene (FIG. 27). Southern hybridization showed the IMT gene was integrated into the Brassica genome with various copy numbers. Total RNA was extracted from developing seeds for northern hybridization analysis as shown in FIG. 28.

EXAMPLE 17

Phytic Acid Analysis in Transgenic Plants

Phytic acid content was analyzed in the mature seeds harvested from $F_0$ transgenic plants. Extraction of the seeds was carried out as described in Example 10. The collected data indicates that on average more than a 15% phytic acid reduction is found in the transgenic plants. FIGS. 29 and 30 show a summary of the data. The collected data indicates that on average moe than 15% phytic acid reduction is found in the transgenic plants produced with the pSIMT vector. $F_1$ seeds are mixtures of transgenic and nontransgenic seeds due to segregation, hence the actual reduction of phytic acid is substantially higher on a per transformed seed basis. F2 and F3 seeds are homozygous lines containing the pSIMT vector. It is evident that under field conditions, homozygous lines carrying the pSIMT vector show and average of 30% reduction in phytic acid levels in the seeds. In addition to the phytic acid analysis, Southern blot analysis was carried out to determine copy number of the inserted genes. Even in plants with a single inserted copy of the gene, significant reduction (34%) of phytic acid is seen (e.g. plant number TP #11). Thus the expression of an enzyme activity capable of modifying myo-inositol in tissues responsible for phytic acid biosynthesis clearly leads to a reduction in phytic acid in seed. It is also clear that the trait of low phytic acid can be transferred sexually since it was heritable thus the method of use can also include the transfer of the trait by conventional breeding techniques once the low phytic acid trait is established.

EXAMPLE 18

Transformation of *Brassica napus* with pNIMT

The vector p35SNIMT was inserted into Agrobacterium stain MP90 by standard triparental mating, followed by Agrobacterium-mediated transformation of Brassica. Transformation was carried out as described in Example 4.

Plants transformed with p35NIMT were obtained and analyzed for reduced phytic acid content as in Example 17. FIG. 31 shows a table of data collected from F1 and F2 transgenic seeds carrying the pNIMT vector grown under field conditions. In the F1 plants the pNIMT insert is segregating thus the seeds analyzed were a mixture of tranagenic and non-transgenic segregants. In the F2 generation, most of the lines were homozygous or nearly homozygous populations. In the F2 analysis, close to a 40% reduction in seed phytic acid content was observed from plants grown under field conditions. Thus the expression of an enzyme capable of reducing the availability of myo-inositol for phytic acid biosynthesis in a seed selective matter leads to a significant reduction in the levels of phytic acid.

EXAMPLE 19

Formation and Accumulation of UDP-galactose Is Prevented by Utilising an Enzyme Activity Heterologous to Plant Cells The enzyme UDP-galactose 4-epimerase (galE) is involved in one of the major steps of galactose metabolism in living systems. It catalyzes the conversion of UDP-galactose into UDP-glucose. The gene for the enzyme is available from human, yeast and bacteria.

The objective of this example is to overexpress this enzyme in specific tissues of the target plant with a view to increasing the pool of UDP-glucose at the expense of that of UDP-galactose. The predicted outcome would be reduced biosynthesis of galactinol, which is the precursor of the anti-nutritional sucrose glycosides (RFO glycosides e.g. raffinose, stachyose, etc.). Achieving this goal will, in addition to reducing the accumulation rate of the undesirable RFO glycosides, lead to enhanced availability of UDP-glucose and sucrose concurrently. The latter will be expected to participate in, and enhance other metabolic pathways where sucrose is needed either for producing other metabolites that are essential for the plant or as carbon source for enhanced plant productivity (e.g. proteins, lipids, overall yield, etc.).

This is an example to illustrate the utility of a bacterial enzyme in higher plants to cause metabolic conversion of one essential substrate into another, whereby the resulting new substrate will be readily utilized by the plant in a variety of important metabolic interconversions.

EXAMPLE 20

Alteration of Levels of Sugar Derivatives by Using the Enzyme Phosphoglucomutase (pgm)

The enzyme phosphoglucomutase (pgm) catalyzes the interconversion of glucose (Glc)-1- and Glc-6-phosphate in the synthesis and consumption of sucrose. The enzyme plays a pivotal role in the synthesis and utilization of sucrose, starch and glycogen, and is present in all organisms. The gene for this enzyme is available from a variety of eukaryotic as well as bacterial sources (e.g. Agrobacterium).

G-1-P and G-6-P are essential substrates in a number of primary carbohydrate metabolic pathways in all living systems. Specifically, G-1-P is the primary substrate for the production of UDP-glucose, which is the major substrate in sucrose biosynthesis. G-6-P, on the other hand, is a major starting material for a number of sugar interconversions, one of which is the synthesis of myo-inositol-1-P. The latter is a major substrate and co-factor in the synthesis of phytic acid and RFOs respectively.

The objective of this example is to show that by overexpressing the bacterial PGM gene in a target plant the relative ratio of G-1-P to G-6-P may be manipulated in favor of one or the other of the two phosphorylated forms of glucose (tissue dependent). By correctly targeting this activity, e.g. in developing seeds for example (sink tissues), an increase in the G-1-P level would be expected, which would be in demand for the production of UDP- or ADP-glucose, and subsequently sucrose and other storage substances such as proteins, lipids or starch. On the other hand the effect of lowering the level of G-6-P would translate into lower levels of the anti-nutritional factors mentioned above.

EXAMPLE 21

Production and Regeneration of Transgenic Maize Cells

Type II callus cultures are initiated from immature zygotic embryos of the genotype Hi-II. (Armstrong et al, (1991) Maize Genet. Coop. Newslett., 65: 92–93). Immature embryos are isolated about 14 days post pollination from greenhouse-grown ears from crosses between Hi-II parent A and Hi-II parent B or F2 embryos derived from a self- or sib-pollination of a Hi-II plant. Immature embryos (1.5 to 3.5 mm) are cultured on initiation medium consisting of N6 salts and vitamins (Chu et al, (1978) The N6 medium and its application to anther culture of cereal crops. Proc. Symp. Plant Tissue Culture, Peking Press, 43–56), 1.0 mg/L 2,4-D, 25 mM L-proline, 100 mg/L casein hydrolysate, 10 mg/L AgNO$_3$, 2.5 g/L GELRITE (Schweizerhall, South Plainfield, N.J.), and 20 g/L sucrose, with a pH of 5.8. After four to six weeks, callus is subcultured onto maintenance medium (initiation medium in which AgNO$_3$ is omitted and L-proline is reduced to 6 mM). Selection for Type II callus is done for ca. 12–16 weeks.

For blasting, or introducing foreign DNA into the plant cells (transformation via microparticle bombardment), 140 μg of plasmid DNA (for example, 35S-PAT/maize globulin promoter/IMT) is precipitated onto 60 mg of alcohol-rinsed, spherical gold particles (1.5–3.0 μm diameter, Aldrich Chemical Co., Inc., Milwaukee, Wis.) by adding 74 μL of 2.5M CaCl$_2$ H$_2$O and 30 μL of 0.1M spermidine (free base) to 300 μL of plasmid DNA and H$_2$O. The solution is immediately vortexed and the DNA-coated gold particles are allowed to settle. The resulting clear supernatant is removed and the gold particles are resuspended in 1 ml of absolute ethanol. This suspension is diluted with absolute ethanol to obtain 15 mg DNA-coated gold/mL.

The plasmid DNA used preferably contains a selectable marker, such as the bar or pat gene, conferring resistance to phosphinothricin or the herbicide glufosinate ammonium and a genetic construct capable of altering secondary metabolism, such as the coding region of the IMT gene described in FIG. 24 or the coding region of the ferulic acid decarboxylase gene described in FIG. 17, under the control of a suitable seed selective promoter such as the maize globulin 1 promoter or the maize zein promoter. Alternatively, a constitutive promoter such as a ubiqitin promoter from maize or a rice actin promoter may be employed to express the IMT or ferulic acid decarboxylase.

Approximately 600 mg of embryogenic callus tissue is spread over the surface of Type II callus maintenance medium lacking casein hydrolysate and L-proline, but supplemented with 0.2 M sorbitol and 0.2 M mannitol as an osmoticum. The callus is maintained for 4 h as a pre-treatment and then transferred to culture dishes containing blasting medium (osmotic media solidified with 20 g/L TC agar (PhytoTechnology Laboratories, LLC, Shawnee Mission, Kans.) instead of 7 g/L GELRITE. Helium gas (blasting) is used to accelerate suspended DNA-coated gold particles towards and into the prepared tissue targets. The device used is described in U.S. Pat. No. 5,141,131 which is incorporated herein by reference. Tissues are covered with a stainless steel screen (104 μm openings) and placed under a partial vacuum of 25 inches of Hg in the device chamber. The DNA-coated gold particles are further diluted 1:1 with absolute ethanol prior to blasting and are accelerated at the callus targets four times using a helium pressure of 1500 psi, with each blast delivering 20 μL of the DNA/gold suspension. Immediately post-blasting, the tissue is transferred to osmotic media for a 16–24 h recovery period. Afterwards, the tissue is divided into small pieces and transferred to selection medium (maintenance medium lacking casein hydrolysate and L-proline but containing 30 mg/L BASTA® (AgrEvo, Berlin, Germany). Every four weeks for 3 months, tissue pieces are non-selectively transferred to fresh selection medium. After 7 weeks and up to 22 weeks, callus sectors found proliferating against a background of growth-inhibited tissue are removed and isolated. The resulting BASTA®-resistant tissue is subcultured biweekly onto fresh selection medium. Following appropriate analysis, positive transgenic lines are identified and transferred to regeneration media.

Regeneration is initiated by transferring callus tissue to cytokinin-based induction medium, which consists of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA®, and 2.5 g/L GELRITE at pH 5.7. The cultures are placed in low light (125 ft-candles) for one week followed by one week in high light (325 ft-candles). Following a two week induction period, tissue is non-selectively transferred to hormone-free regeneration medium, which is identical to the induction medium except that it lacks 2,4-D and BAP, and is kept in high light. Small (1.5–3 cm) plantlets are removed and placed in 150×25 mm culture tubes containing SH medium (SH salts and vitamins (Schenk and Hildebrandt, (1972) Can. J. Bot. 50:199–204), 10 g/L sucrose, 100 mg/L myo-inositol, 5 mL/L FeEDTA, and 2.5 g/L GELRITE, pH 5.8).

Larger plantlets are transferred to 12 cm pots containing approximately 0.25 kg of METRO-MIX 360 (The Scotts Co. Marysville, Ohio) in the greenhouse as soon as they exhibit growth and develop a sufficient root system. The plantlets are grown with a 16 h photoperiod supplemented by a combination of high pressure sodium and metal halide lamps, and are watered as needed with a combination of three independent Peters Excel fertilizer formulations (Grace-Sierra Horticultural Products Company, Milpitas, Calif.). At the 6–8 leaf stage, plants are transplanted to five gallon pots containing approximately 4 kg METRO-MIX 360, and grown to mature fertile transgenic maize. The seed set by these plants contain the genes inserted into the immature embryos and when grown into plants will express the proteins encoded by the inserted DNA.

EXAMPLE 22

Production of Rice Transgenics

For initiation of embryogenic callus, mature seeds of a Japonica cultivar, Taipei 309 are dehusked and surface-sterilized in 70% ethanol for 2–5 min. followed by a 30–45 min soak in 50% commercial bleach (2.6% sodium hypochlorite) with a few drops of 'Liquinox' soap. The seeds are then rinsed 3 times in sterile distilled water and placed on filter paper before transferring to 'callus induction'medium (i.e., NB). The NB medium consists of N6 macro elements (Chu, 1978, The N6 medium and its application to anther culture of cereal crops. Proc. Symp. Plant Tissue Culture, Peking Press,. p43–56), B5 micro elements and vitamins (Gamborg et al., 1969, Nutrient requirements of suspension cultures of soybean root cells. Exp. Cell Res. 50: 151–158), 300 mg/L casein hydrolysate, 500 mg/L L-proline, 500 mg/L L-glutamine, 30 g/L sucrose, 2 mg/L 2,4-dichloro-phenoxyacetic acid (2,4-D), and 2.5 g/L gelrite (Schweizerhall, NJ) with the pH adjusted to 5.8. The mature seed cultured on callus 'induction' media are incubated in the dark at 28° C. After 3 weeks of culture, the emerging primary callus induced from the scutellar region of a mature embryo is transferred to fresh NB medium for further maintenance.

Biolistic transformation of the plant tissue is used to introduce the foreign DNA. About 140 μg of plasmid DNA is precipitated onto 60 mg of 1.0 micron (Bio-Rad) gold particles as described in Example 21. Plasmid containing the maize ubiquitin promoter driving the hpt (hygromycin phosphotransferase) and the maize ubiquitin 1, maize globulin 1, or zein promoter driving the IMT gene is used. About 140 μg of plasmid DNA is precipitated onto 60 mg of 1.0 micron (Bio-Rad) gold particles as described herein.

For helium blasting, actively growing embryogenic callus cultures, 2–4 mm in size, are subjected to a high osmoticum treatment. This treatment includes placing of callus on NB medium with 0.2 M mannitol and 0.2 M sorbitol (Vain et al., 1993, Osmoticum treatment enhances particle bombardment-mediated transient and stable transformation of maize. Plant Cell Rep. 12: 84–88) for 4 h before helium blasting. Following osmoticum treatment, callus cultures are transferred to 'blasting' medium (NB+2% agar) and covered with a stainless steel screen (230 micron). The callus cultures are blasted at 2,000 psi helium pressures twice per target. After blasting, callus is transferred back to the media with high osmoticum overnight before placing on selection medium, which consists NB medium with 30 mg/L hygromycin. After 2 weeks, the cultures are transferred to fresh selection medium with a higher concentration of selection agent, i.e., NB+50 mg/L hygromycin (Li et al., 1993, An improved rice transformation system using the Biolistic method. Plant Cell Rep. 12: 250–255).

Compact, white-yellow, embryogenic callus cultures, recovered on NB+50 mg/L hygromycin, are regenerated by transferring to 'pre-regeneration' (PR) medium+50 mg/L hygromycin. The PR medium consists of NB medium with 2 mg/L benzyl aminopurine (BAP), 1 mg/L naphthalene acetic acid (NAA), and 5 mg/L abscisic acid (ABA). After 2 weeks of culture in the dark, the callus is transferred to 'regeneration' (RN) medium. The composition of RN medium is NB medium with 3 mg/L BAP, and 0.5 mg/L NAA. The callus cultures on RN medium are incubated for 2 weeks at 28° C. under high fluorescent light (325-ft-candles). After plantlets start forming the plantlets with a 2 cm shoot are transferred to magenta boxes containing 1/2 MS medium (Murashige and Skoog, 1962, A revised medium for rapid growth and bioassays with tobacco tissue cultures. Physiol. Plant.15:473–497) with 1/2 B5 vitamins, 10 g/L sucrose, 0.05 mg/L NAA, 50 mg/L hygromycin and 2.5 g/L gelrite adjusted to pH 5.8. Large plants 8–15 cm with well-developed root systems, are transferred to soil (1 metromix: 1 top soil) and raised in the greenhouse (29/24° C. day/night cycle, 50–60% humidity, 12 h photoperiod). The rice plants grow into fertile rice transgenic crop. The seed set by these plants contain the genes inserted into the rice callus and when grown into plants will express the proteins encoded by the inserted DNA.

What is claimed is:

1. A method for improving a nutritional profile of a plant, comprising the steps of:
    transforming a plant cell of said plant with an expression cassette comprising a nucleic acid sequence encoding a choline metabolizing enzyme operably linked to a seed specific promoter, wherein the enzyme reduces choline availability in transformed seeds said plant selected from the group consisting of corn, canola, wheat, barley, oats, alfalfa, soybeans and sorghum; and
    recovering a genetically altered plant from said plant cell, said genetically altered plant characterized by an improved nutritional profile relative to a wild-type of said plant.

2. The method according to claim 1 wherein said choline metabolizing enzyme is choline oxidase.

3. The method according to claim 2, wherein said expression cassette further comprises a nucleic acid sequence that encodes a betaine aldehyde dehydrogenase capable of converting betaine aldehyde to betaine.

4. The method according to claim 1, wherein said seed selective promoter is a phaseolin promoter or a napin promoter.

5. The method according to claim 1, comprising the further step of:
    growing said genetically altered plant under conditions that permit the formation of seed, and recovering said seed.

6. A genetically altered plant or a descendant thereof, comprising a recombinant nucleic acid molecule stably incorporated into the genome of said plant, said recombinant nucleic acid molecule comprising:
    (a) a seed-specific promoter; and
    (b) a nucleic acid sequence operably linked to said seed-specific promoter, said nucleic acid sequence encoding a choline metabolizing enzyme wherein the enzyme reduces choline availability in transformed seeds;
    said plant being selected from the group consisting of corn, canola, wheat, barley, oats, alfalfa, soybeans and sorghum; and
    said genetically altered plant being characterized by an improved nutritional profile relative to a wild-type of said plant;
    or a cell, seed or component of said genetically altered plant or descendant thereof.

7. The genetically altered plant or descendant thereof according to claim 6, wherein said choline metabolizing enzyme is choline oxidase.

8. The genetically altered plant or descendant thereof according to claim 7, wherein said recombinant nucleic acid molecule further comprises a nucleic acid sequence that encodes a betaine aldehyde dehydrogenase capable of converting betaine aldehyde to betaine.

9. The genetically altered plant or descendant thereof according to claim 6, wherein said seed selective promoter is a phaseolin promoter or a napin promoter.

10. The genetically altered plant or descendant thereof according to claim 6, having reduced sinapine content relative to a wild-type of said plant.

11. The genetically altered plant or descendant thereof according to claim 6, having altered lignin content relative to a wild-type of said plant.

12. An animal feed derived at least in part from the genetically modified plant or descendant thereof according to claim 6, or from a cell, seed or component thereof.

* * * * *

SEQUENCE LISTING

<160> NUMBER OF SEQ ID NOS: 7

<210> SEQ ID NO 1
<211> LENGTH: 483
<212> TYPE: DNA
<213> ORGANISM: Arthrobacter pascens

<400> SEQUENCE: 1

```
atggaccaat tcgtgggtct ccacatgatc tacacatacg agaacggttg ggagtacgaa      60
atctacatca agaacgacca cacaatcgac taccgtatcc acagtggtat ggtgggtggt     120
aggtgggtga gggaccaaga ggtgaacatc gtgaagctca caaagggtgt gtacaaggtg     180
agctggacag agccaacagg tacagacgtg agcctcaact tcatgccaga ggagaagagg     240
atgcacggtg tgatcttctt cccaaagtgg gtgcacgaga ggccagacat cacagtgtgc     300
taccaaaacg actacatcga cctcatgaag gagagcaggg agaagtacga gacatacccca    360 aagtacgtgg tgccagagtt cgctgacatc acatacatcc accacgctgg agtgaacgac     420
gagacaatca tcgctgaggc tccatacgag ggtatgacag acgagatcag ggctggtagg     480
aag                                                                   483
```

<210> SEQ ID NO 2
<211> LENGTH: 161
<212> TYPE: PRT
<213> ORGANISM: Bacillus pumilus

<400> SEQUENCE: 2

```
Met Asp Gln Phe Val Gly Leu His Met Ile Tyr Thr Tyr Glu Asn Gly
 1               5                  10                  15

Trp Glu Tyr Glu Ile Tyr Ile Lys Asn Asp His Thr Ile Asp Tyr Arg
            20                  25                  30

Ile His Ser Gly Met Val Gly Arg Trp Val Arg Asp Gln Glu Val
        35                  40                  45

Asn Ile Val Lys Leu Thr Lys Gly Val Tyr Lys Val Ser Trp Thr Glu
    50                  55                  60

Pro Thr Gly Thr Asp Val Ser Leu Asn Phe Met Pro Glu Glu Lys Arg
65                  70                  75                  80

Met His Gly Val Ile Phe Phe Pro Lys Trp Val His Glu Arg Pro Asp
                85                  90                  95

Ile Thr Val Cys Tyr Gln Asn Asp Tyr Ile Asp Leu Met Lys Glu Ser
```

```
                    100                 105                 110
Arg Glu Lys Tyr Glu Thr Tyr Pro Lys Tyr Val Val Pro Glu Phe Ala
            115                 120                 125

Asp Ile Thr Tyr Ile His His Ala Gly Val Asn Asp Glu Thr Ile Ile
    130                 135                 140

Ala Glu Ala Pro Tyr Glu Gly Met Thr Asp Glu Ile Arg Ala Gly Arg
145                 150                 155                 160

Lys

<210> SEQ ID NO 3
<211> LENGTH: 546
<212> TYPE: PRT
<213> ORGANISM: Arthrobacter pascens

<400> SEQUENCE: 3

Met His Ile Asp Asn Val Glu Asn Leu Asn Asp Arg Glu Phe Asp Tyr
  1               5                  10                  15

Ile Ile Ile Gly Gly Gly Ser Ala Gly Ala Ala Val Ala Ala Arg Leu
                 20                  25                  30

Ser Glu Glu Pro Thr Val Ser Val Ala Leu Val Glu Ala Gly Pro Asp
         35                  40                  45

Asp Arg Gly Val Pro Glu Val Leu Gln Leu Asp Arg Trp Met Glu Leu
 50                  55                  60

Leu Glu Ser Gly Tyr Asp Trp Asp Tyr Pro Ile Glu Pro Gln Glu Asn
 65                  70                  75                  80

Gly Asn Ser Phe Met Arg His Ala Arg Ala Lys Ile Met Gly Gly Cys
                 85                  90                  95

Ser Ser His Asn Ser Cys Ile Ala Phe Trp Ala Pro Arg Glu Asp Leu
            100                 105                 110

Asp Glu Trp Glu Ser Lys Tyr Gly Ala Thr Gly Trp Asn Ala Glu Ser
            115                 120                 125

Ala Trp Pro Leu Tyr Gln Arg Leu Glu Thr Asn Glu Asp Ala Gly Pro
    130                 135                 140

Asp Ala Pro His His Gly Asp Ser Gly Pro Val His Leu Met Asn Val
145                 150                 155                 160

Pro Pro Ala Asp Pro Ala Gly Val Ala Leu Leu Asp Ala Cys Glu Gln
                165                 170                 175

Ala Gly Ile Pro Arg Ala Lys Phe Asn Thr Gly Thr Thr Val Ile Asn
            180                 185                 190

Gly Ala Asn Phe Phe Gln Ile Thr Arg Arg Ala Asp Gly Thr Arg Ser
            195                 200                 205

Ser Ser Ser Val Ser Tyr Ile His Pro Ile Ile Glu Arg Gly Asn Phe
    210                 215                 220

Thr Leu Leu Thr Gly Leu Arg Ala Arg Gln Leu Val Phe Asp Ala Asp
225                 230                 235                 240

Lys Arg Cys Thr Gly Val Asp Val Val Asp Ser Ala Phe Gly Arg Thr
                245                 250                 255

His Arg Leu Ser Ala Arg Cys Glu Val Ile Leu Ser Thr Gly Ala Ile
            260                 265                 270

Asp Ser Pro Lys Leu Leu Met Leu Ser Gly Ile Gly Pro Ala Ala His
            275                 280                 285

Leu Ala Glu His Gly Val Glu Val Leu Asp Ser Pro Gly Val Gly
    290                 295                 300

Glu His Leu Gln Asp His Pro Glu Gly Val Val Gln Phe Glu Ala Lys
```

```
305                 310                 315                 320
Gln Gln Met Val Gln Thr Ser Thr Gln Trp Trp Glu Ile Gly Ile Phe
                325                 330                 335
Thr Pro Thr Glu Asn Gly Leu Asp Arg Pro Asp Leu Met Met His Tyr
                340                 345                 350
Gly Ser Val Pro Phe Asp Met Asn Thr Leu Arg Tyr Gly Tyr Pro Thr
                355                 360                 365
Thr Glu Asn Gly Phe Ser Leu Thr Pro Asn Val Thr His Ala Arg Ser
            370                 375                 380
Arg Gly Thr Val Arg Leu Arg Ser Arg Asp Phe Arg Asp Lys Pro Ala
385                 390                 395                 400
Val Asp Pro Arg Tyr Phe Thr Asp Pro Glu Gly His Asp Met Arg Val
                405                 410                 415
Met Val Ala Gly Ile Arg Lys Ala Arg Glu Ile Ala Ala Gln Pro Ala
                420                 425                 430
Met Ala Glu Trp Thr Gly Arg Glu Leu Ser Pro Gly Thr Glu Ala Gln
                435                 440                 445
Thr Asp Glu Glu Leu Gln Asp Tyr Ile Arg Lys Thr His Asn Thr Val
            450                 455                 460
Tyr His Pro Val Gly Thr Val Arg Met Gly Pro Ala Asp Asp Met
465                 470                 475                 480
Ser Pro Leu Asp Pro Glu Leu Arg Val Lys Gly Val Thr Gly Leu Arg
                485                 490                 495
Val Ala Asp Ala Ser Val Met Pro Glu His Val Thr Val Asn Pro Asn
                500                 505                 510
Ile Thr Val Met Met Ile Gly Glu Arg Cys Ala Asp Leu Ile Arg Ala
                515                 520                 525
Ser Arg Thr Gly Glu Thr Thr Thr Ala Glu Ala Glu Leu Ser Ala Ser
            530                 535                 540
Leu Ala
545

<210> SEQ ID NO 4
<211> LENGTH: 1641
<212> TYPE: DNA
<213> ORGANISM: Arthrobacter pascens

<400> SEQUENCE: 4
atgcacatcg acaacgtcga aaacctcaac gaccgcgagt cgactacat catcatcggc      60
ggcggttccg ccggagcggc agtcgccgcc cgcctgagcg aggagcccac cgtgtccgtg    120
gcgctggtgg aggccggccc ggacgaccgc ggcgttcccg aggtactgca gctcgaccgc    180
tggatggagc tgctggaatc cggctacgac tgggactacc cgatcgaacc gcaggagaac    240
ggcaactcct tcatgcgcca cgcccgcgcg aagatcatgg tggctgctc cagccacaac    300
tcctgcatcg ccttctgggc cccgcgcgaa gacctggacg agtgggagtc caagtacggc    360
gccaccggct ggaacgctga gtccgcctgg ccgctgtacc agcggctgga ccaacgag      420
gacgccggcc cggacgcgcc gcaccacggc gactcaggcc cggtgcacct gatgaacgtg    480
ccccggcgca accccgccgg cgtcgcactc ctggacgcct cgaacaggc aggcattccg    540
cgcgcgaagt tcaacaccgg caccaccgtg atcaatggcg ccaactttttt ccagatcaca    600
cgccgcgcgg acggcaccgc ttcctccagc tcggtctcct acatccaccc gatcatcgag    660
cgcgggaact tcaccctgct gaccggggttg cgcgcccggc aactggtgtt cgacgcggac    720
```

-continued

| | |
|---|---|
| aagcgctgca ccggcgtcga cgttgtggac tcggcgttcg gccggactca ccggctctcc | 780 |
| gcgcgttgcg aggtcatcct gtccaccggc gccattgact cgcctaagct gctcatgctc | 840 |
| tccggcatcg gccccgccgc gcacctcgcc gagcacggcg tcgaggtcct ggtcgactcc | 900 |
| cccggtgtcg gcgagcacct gcaggaccac cccgaaggcg tcgtccagtt cgaggccaag | 960 |
| cagcagatgt gcagacttc gacgcagtgg tgggagatcg gcatcttcac ccccaccgag | 1020 |
| aacggcctgg accgcccgga cctgatgatg cactacggct ccgtcccgtt cgacatgaac | 1080 |
| accctgcggt acggctaccc caccacggag aacggcttca gcctcacgcc gaacgtcacg | 1140 |
| cacgcccgct cccgcggcac cgtccggctg cgcagccgcg acttccgcga caagcccgcc | 1200 |
| gtcgacccgc ggtacttcac tgatccggag gccacgaca tgcgcgtcat ggtggccggc | 1260 |
| atccgcaagg cccgtgaaat cgccgcccag cctgccatgg ccgaatggac cggccgcgag | 1320 |
| ctctcgcccg gcaccgaggc gcagaccgac gaggaactgc aggactacat ccgcaagacg | 1380 |
| cacaacaccg tttaccaccc cgtcggcacc gtccgcatgg accagccga cgacgacatg | 1440 |
| tcgccgctcg accccgagct gcgggtgaag ggcgtgaccg gctgcgcgt cgccgatgcc | 1500 |
| tctgtcatgc ctgaacacgt cacggtcaat cccaacatca ccgtcatgat gatcggcgaa | 1560 |
| cgctgcgccg acctcatccg cgccagccgg accggcgaaa caacgacggc ggaggcggag | 1620 |
| ctcagcgcgt ccctcgcctg a | 1641 |

<210> SEQ ID NO 5
<211> LENGTH: 1494
<212> TYPE: DNA
<213> ORGANISM: Mesembryanthemum crystallinum

<400> SEQUENCE: 5

| | |
|---|---|
| aaaaaaaaaa ttttacttct ctgttttacc aaaagagaa aaaaaatga ctacttacac | 60 |
| caatggcaac tacacacaac caaaaaccct agacaaagat gaacaattag ctggtttggc | 120 |
| agtgacatta gcaaatgcag ctgcttttcc aatgatcctg aaatcagcct ttgagctaaa | 180 |
| aatccttgac atattctcaa aagcagggga aggcgtgttt gtatcgactt ctgagatcgc | 240 |
| tagccaaatc ggggcaaaga accctaatgc cccggtgttg ttggaccgga tgctccggct | 300 |
| cctggctagc cactctgtgt taacatgcaa gctccaaaag ggtgagggtg gttctcaaag | 360 |
| ggtgtatggt ccagctcccc tttgcaacta tcttgctagt aatgatggtc aaggctctct | 420 |
| tggcccttg cttgttttgc atcatgacaa ggtcatgatg gagagttggt ttcacttgaa | 480 |
| tgattacata ctagaaggag gtgttccatt caagcgcgct catgggatga tccaattcga | 540 |
| ctacactggg actgatgaaa ggttcaatca tgtgttcaac caagggatgg cacaccacac | 600 |
| tatcctggtc atgaagaagc tccttgacaa ctacaatggg tttaatgatg tcaaggtcct | 660 |
| agttgatgtg ggtggtaaca ttggtgtcaa tgtgagcatg atcgtcgcta agcatactca | 720 |
| cattaagggc atcaactatg acttgcctca tgtcattgct gatgctcctt cttaccccgg | 780 |
| tgtggagcat gttggtggta acatgtttga gagcatacca caagcagatg ccatttcat | 840 |
| gaagtgggtg ttgcatgatt ggagcgacga gcattgcgtg aagatactca acaagtgcta | 900 |
| tgagagcctg gcaaagggag ggaagatcat ccttgtggaa tcgcttatac cagtaatccc | 960 |
| agaagacaac ctcgaatcac acatggtgtt tagccttgat tgccacactt tggtgcacaa | 1020 |
| ccaaggtgga aaagagagat caaggaggga ttttgaagcc ttagcttcca agactggctt | 1080 |
| ctctacagtt gatgtcattt gctgtgccta tgacacttgg gtcatggagc tctacaagaa | 1140 |
| gtgattcaag ctctaaatgc tgtgttgttg tcattgttgc tagcccaagt agctagctag | 1200 |

-continued

```
ctggttaaaa tttctcctac ctagcatttg ttttatggct aagttgagga gattcatgta      1260
ttgtaaatgt tgtgtttggg tttgggtttg tatttgtatt tgtgttttgt tgttgtgtct      1320
ttgtagctaa gttgatatcc tgctcatcta ggctggctgc attttttttg tggctgcctg      1380
acaatgtagc atttgtggtt ttctttcaat aaagcatcta ttgtacctct gttatcagtg      1440
tatgatttgc ctttattttt aataacttaa tttttttttt cttgtttata tcca            1494

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 6
tttttggatc catgactact tacacaatgg caactaca                                38

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 7
ttttttttgc ggccgcataa aggcaaatca tacactg                                 37
```